United States Patent
Bagley et al.

(10) Patent No.: US 8,802,690 B2
(45) Date of Patent: *Aug. 12, 2014

(54) N1-PYRAZOLOSPIROKETONE ACETYL-COA CARBOXYLASE INHIBITORS

(71) Applicant: Pfizer Inc., New York, NY (US)

(72) Inventors: Scott William Bagley, Mystic, CT (US); David Andrew Griffith, Sudbury, MA (US); Daniel Wei-Shung Kung, Salem, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/939,450

(22) Filed: Jul. 11, 2013

(65) Prior Publication Data

US 2013/0296319 A1  Nov. 7, 2013

Related U.S. Application Data

(63) Continuation of application No. 13/644,415, filed on Oct. 4, 2012, now Pat. No. 8,507,681, which is a continuation of application No. 12/941,133, filed on Nov. 8, 2010, now Pat. No. 8,288,405.

(60) Provisional application No. 61/259,823, filed on Nov. 10, 2009.

(51) Int. Cl.
  C07D 487/10    (2006.01)
  A61K 31/438    (2006.01)

(52) U.S. Cl.
  USPC .......................................... 514/278; 546/20

(58) Field of Classification Search
  USPC ............................................ 546/20; 514/278
  See application file for complete search history.

(56) References Cited

U.S. PATENT DOCUMENTS

| | | | | |
|---|---|---|---|---|
| 8,288,405 B2 * | 10/2012 | Bagley et al. | ............... | 514/278 |
| 8,318,762 B2 * | 11/2012 | Corbett et al. | ............... | 514/278 |
| 8,507,681 B2 * | 8/2013 | Bagley et al. | ............... | 546/17 |
| 2008/0171761 A1 | 7/2008 | Iino et al. | | |
| 2009/0253725 A1 | 10/2009 | Chang et al. | | |
| 2010/0009982 A1 | 1/2010 | Anderson et al. | | |
| 2011/0028390 A1 | 2/2011 | Corbett et al. | | |

FOREIGN PATENT DOCUMENTS

| | | |
|---|---|---|
| EP | 1911753 | 4/2008 |
| EP | 2123652 | 11/2009 |
| JP | 2005119987 | 5/2005 |
| WO | 03072197 | 9/2003 |
| WO | 2004002986 | 1/2004 |
| WO | 2004092179 | 10/2004 |
| WO | 2005113069 | 12/2005 |
| WO | 2007011809 | 1/2007 |
| WO | 2007011811 | 1/2007 |
| WO | 2007061676 | 5/2007 |
| WO | 2007095603 | 8/2007 |
| WO | 2008065508 | 6/2008 |
| WO | 2008088689 | 7/2008 |
| WO | 2008102749 | 8/2008 |
| WO | 2008125945 | 10/2008 |
| WO | 2009144554 | 12/2009 |
| WO | 2009144555 | 12/2009 |
| WO | 2010002010 | 1/2010 |
| WO | 2011058473 | 5/2011 |
| WO | 2011058474 | 5/2011 |
| WO | 2012042433 | 4/2012 |

OTHER PUBLICATIONS

Bioisosterism: A Rational Approach in Drug Design, Patani George et al, 1996.*
Savage, et al., "Reversal of diet-induced hepatic steatosis and hepatic insulin resistance by antisense oligonucleotide inhibitors of acetyl-CoA carboxylases 1 and 2", The Journal of Clinical Investigation, vol. 116(3), pp. 817-824 (2006).
Oh, et al., "Glucose and fat metabolism in adipose tissue of acetyl-CoA carboxylase 2 knockout mice", PNAS, vol. 102 (5), pp. 1384-1389 (2005).
Abu-Elheiga, et al., "Acetyl-CoA carboxylase 2 mutant mice are protected against obesity and diabetes induced by high-fat/high-carbohydrate diets", PNAS, vol. 100(18), pp. 10207-10212 (2003).
Choi, et al., "Continuous fat oxidation in acetyl-CoA carboxylase 2 knockout mice increases total energy expenditure, reduces fat mass, and improves insulin sensitivity", PNAS, vol. 104(42), pp. 16480-16485 (2007).
Database WPI Week 200537; Derwent Publications Ltd. No. 2005-359210 (XP002471702).
Bagley, et al., "Synthesis of 7-oxo-dihydrospiro[indazole-5,4'-piperidine] Acetyl-CoA Carboxylase Inhibitors", The Journal of Organic Chemistry, vol. 77(3), pp. 1497-1506 (2012).

* cited by examiner

*Primary Examiner* — Rita Desai
(74) *Attorney, Agent, or Firm* — James T. Wasicak

(57) ABSTRACT

The invention provides a compound of Formula (I)

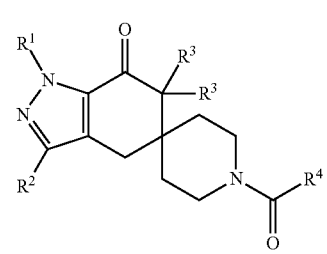

or a pharmaceutically acceptable salt of the compound, wherein $R^1$, $R^2$, $R^3$ and $R^4$ are as described herein; pharmaceutical compositions thereof; and the use thereof in treating diseases, conditions or disorders modulated by the inhibition of an acetyl-CoA carboxylase enzyme(s) in an animal.

4 Claims, 4 Drawing Sheets

FIGURE 1

SEQ. ID NO. 1:

MAHHHHHHDEVDDEPSPLAQPLELNQHSRFIIGSVSEDNSEDEISNLVKLDLLEKEGSLSPA
SVGSDTLSDLGISSLQDGLALHIRSSMSGLHLVKQGRDRKKIDSQRDFTVASPAEFVTRFGG
NKVIEKVLIANNGIAAVKCMRSIRRWSYEMFRNERAIRFVVMVTPEDLKANAEYIKMADHYVP
VPGGPNNNNYANVELILDIAKRIPVQAVWAGWGHASENPKLPELLLKNGIAFMGPPSQAMW
ALGDKIASSIVAQTAGIPTLPWSGSGLRVDWQENDFSKRILNVPQELYEKGYVKDVDDGLQA
AEEVGYPVMIKASEGGGGKGIRKVNNADDFPNLFRQVQAEVPGSPIFVMRLAKQSRHLEVQI
LADQYGNAISLFGRDCSVQRRHQKIIEEAPATIATPAVFEHMEQCAVKLAKMVGYVSAGTVE
YLYSQDGSFYFLELNPRLQVEHPCTEMVADVNLPAAQLQIAMGIPLYRIKDIRMMYGVSPWG
DSPIDFEDSAHVPCPRGHVIAARITSENPDEGFKPSSGTVQELNFRSNKNVWGYFSVAAAG
GLHEFADSQFGH
CFSWGENREEAISNMVVALKELSIRGDFRTTVEYLIKLLETESFQMNRIDTGWLDRLIAEKVQ
AERPDTMLGVVCGALHVADVSLRNSVSNFLHSLERGQVLPAHTLLNTVDVELIYEGVKYVLK
VTRQSPNSYVVIMNGSCVEVDVHRLSDGGLLLSYDGSSYTTYMKEEVDRYRITIGNKTCVFE
KENDPSVMRSPSAGKLIQYIVEDGGHVFAGQCYAEIEVMKMVMTLTAVESGCIHYVKRPGA
ALDPGCVLAKMQLDNPSKVQQAELHTGSLPRIQSTALRGEKLHRVFHYVLDNLVNVMNGYC
LPDPFFSSKVKDWVERLMKTLRDPSLPLLELQDIMTSVSGRIPPNVEKSIKKEMAQYASNITS
VLCQFPSQQIANILDSHAATLNRKSEREVFFMNTQSIVQLVQRYRSGIRGHMKAVVMDLLRQ
YLRVETQFQNGHYDKCVFALREENKSDMNTVLNYIFSHAQVTKKNLLVTMLIDQLCGRDPTL
TDELLNILTELTQLSKTTNAKVALRARQVLIASHLPSYELRHNQVESIFLSAIDMYGHQFCIENL
QKLILSETSIFDVLPNFFYHSNQVVRMAALEVYVRRAYIAYELNSVQHRQLKDNTCVVEFQFM
LPTSHPNRGNIPTLNRMSFSSNLNHYGMTHVASVSDVLLDNSFTPPCQRMGGMVSFRTFED
FVRIFDEVMGCFSDSPPQSPTFPEAGHTSLYDEDKVPRDEPIHILNVAIKTDCDIEDDRLAAM
FREFTQQNKATLVDHGIRRLTFLVAQKDFRKQVNYEVDRRFHREFPKFFTFRARDKFEEDRI
YRHLEPALAFQLELNRMRNFDLTAIPCANHKMHLYLGAAKVEVGTEVTDYRFFVRAIIRHSDL
VTKEASFEYLQNEGERLLLEAMDELEVAFNNTNVRTDCNHIFLNFVPTVIMDPSKIEESVRSM
VMRYGSRLWKLRVLQAELKINIRLTPTGKAIPIRLFLTNESGYYLDISLYKEVTDSRTAQIMFQ
AYGDKQGPLHGMLINTPYVTKDLLQSKRFQAQSLGTTYIYDIPEMFRQSLIKLWESMSTQAFL
PSPPLPSDMLTYTELVLDDQGQLVHMNRLPGGNEIGMVAWKMTFKSPEYPEGRDIIVIGNDI
TYRIGSFGPQEDLLFLRASELARAEGIPRIYVSANSGARIGLAEEIRHMFHVAWVDPEDPYKG
YRYLYLTPQDYKRVSAL

FIGURE 1 (continued)

NSVHCEHVEDEGESRYKITDIIGKEEGIGPENLRGSGMIAGESSLAYNEIITISLVTCRAIGIGA
YLVRLGQRTIQVENSHLILTGAGALNKVLGREVYTSNNQLGGIQIMHNNGVTHCTVCDDFEG
VFTVLHWLSYMPKSVHSSVPLLNSKDPIDRIIEFVPTKTPYDPRWMLAGRPHPTQKGQWLS
GFFDYGSFSEIMQPWAQTVVVGRARLGGIPVGVVAVETRTVELSIPADPANLDSEAKIIQQA
GQVWFPDSAFKTYQAIKDFNREGLPLMVFANWRGFSGGMKDMYDQVLKFGAYIVDGLREC
CQPVLVYIPPQAELRGGSWVVIDSSINPRHMEMYADRESRGSVLEPEGTVEIKFRRKDLVKT
MRRVDPVYIHLAERLGTPELSTAERKELENKLKEREEFLIPIYHQVAVQFADLHDTPGRMQEK
GVISDILDWKTSRTFFYWRLRRLLLEDLVKKKIHNANPELTDGQIQAMLRRWFVEVEGTVKA
YVWDNNKDLAEWLEKQLTEEDGVHSVIEENIKCISRDYVLKQIRSLVQANPEVAMDSIIHMTQ
HISPTQRAEVIRILSTMDSPST

FIGURE 2

SEQ. ID NO. 2:

MVLLLCLSCLIFSCLTFSWLKIWGKMTDSKPITKSKSEANLIPSQEPFPASDNSGETPQR
NGEGHTLPKTPSQAEPASHKGPKDAGRRRNSLPPSHQKPPRNPLSSSDAAPSPELQA
NGTGTQGLEATDTNGLSSSARPQGQQAGSPSKEDKKQANIKRQLMTNFILGSFDDYSS
DEDSVAGSSRESTRKGSRASLGALSLEAYLTTGEAETRVPTMRPSMSGLHLVKRGRE
HKKLDLHRDFTVASPAEFVTRFGGDRVIEKVLIANNGIAAVKCMRSIRRWAYEMFRNER
AIRFVVMVTPEDLKANAEYIKMADHYVPVPGGPNNNNYANVELIVDIAKRIPVQAVWAG
WGHASENPKLPELLCKNGVAFLGPPSEAMWALGDKIASTVVAQTLQVPTLPWSGSGL
TVEWTEDDLQQGKRISVPEDVYDKGCVKDVDEGLEAAERIGFPLMIKASEGGGGKGIR
KAESAEDFPILFRQVQSEIPGSPIFLMKLAQHARHLEVQILADQYGNAVSLFGRDCSIQR
RHQKIVEEAPATIAPLAIFEFMEQCAIRLAKTVGYVSAGTVEYLYSQDGSFHFLELNPRL
QVEHPCTEMIADVNLPAAQLQIAMGVPLHRLKDIRLLYGESPWGVTPISFETPSNPPLA
RGHVIAARITSENPDEGFKPSSGTVQELNFRSSKNVWGYFSVAATGGLHEFADSQFGH
CFSWGENREEAISNMVVALKELSIRGDFRTTVEYLINLLETESFQNNDIDTGWLDYLIAE
KVQAEKPDIMLGVVCGALNVADAMFRTCMTDFLHSLERGQVLPADSLLNLVDVELIYG
GVKYILKVARQSLTMFVLIMNGCHIEIDAHRLNDGGLLLSYNGNSYTTYMKEEVDSYRITI
GNKTCVFEKENDPTVLRSPSAGKLTQYTVEDGGHVEAGSSYAEMEVMKMIMTLNVQE
RGRVKYIKRPGAVLEAGCVVARLELDDPSKVHPAEPFTGELPAQQTLPILGEKLHQVFH
SVLENLTNVMSGFCLPEPVFSIKLKEWVQKLMMTLRHPSLPLLELQEIMTSVAGRIPAPV
EKSVRRVMAQYASNITSVLCQFPSQQIATILDCHAATLQRKADREVFFINTQSIVQLVQR
YRSGIRGYMKTVVLDLLRRYLRVEHHFQQAHYDKCVINLREQFKPDMSQVLDCIFSHA
QVAKKNQLVIMLIDELCGPDPSLSDELISILNELTQLSKSEHCKVALRARQILIASHLPSYE
LRHNQVESIFLSAIDMYGHQFCPENLKKLILSETTIFDVLPTFFYHANKVVCMASLEVYVR
RGYIAYELNSLQHRQLPDGTCVVEFQFMLPSSHPNRMTVPISITNPDLLRHSTELFMDS
GFSPLCQRMGAMVAFRRFEDFTRNFDEVISCFANVPKDTPLFSEARTSLYSEDDCKSL
REEPIHILNVSIQCADHLEDEALVPILRTFVQSKKNILVDYGLRRITFLIAQEKEFPKFFTFR
ARDEFAEDRIYRHLEPALAFQLELNRMRNFDLTAVPCANHKMHLYLGAAKVKEGVEVT
DHRFFIRAIIRHSDLITKEASFEYLQNEGERLLLEAMDELEVAFNNTSVRTDCNHIFLNFV
PTVIMDPFKIEESVRYMVMRYGSRLWKLRVLQAEVKINIRQTTTGSAVPIRLFITNESGY
YLDISLYKEVTDSRSGNIMFHSFGNKQGPQHGMLINTPYVTKDLLQAKRFQAQTLGTTY

FIGURE 2 (continued)

```
IYDFPEMFRQALFKLWGSPDKYPKDILTYTELVLDSQGQLVEMNRLPGGNEVGMVAFK
MRFKTQEYPEGRDVIVIGNDITFRIGSFGPGEDLLYLRASEMARAEGIPKIYVAANSGARI
GMAEEIKHMFHVAWVDPEDPHKGFKYLYLTPQDYTRISSLNSVHCKHIEEGGESRYMIT
DIIGKDDGLGVENLRGSGMIAGESSLAYEEIVTISLVTCRAIGIGAYLVRLGQRVIQVENS
HIILTGASALNKVLGREVYTSNNQLGGVQIMHYNGVSHITVPDDFEGVYTILEWLSYMPK
DNHSPVPIITPTDPIDREIEFLPSRAPYDPRWMLAGRPHPTLKGTWQSGFFDHGSFKEI
MAPWAQTVVTGRARLGGIPVGVIAVETRTVEVAVPADPANLDSEAKIIQQAGQVWFPD
SAYKTAQAIKDFNREKLPLMIFANWRGFSGGMKDMYDQVLKFGAYIVDGLRQYKQPILI
YIPPYAELRGGSWVVIDATINPLCIEMYADKESRGGVLEPEGTVEIKFRKKDLIKSMRRID
PAYKKLMEQLGEPDLSDKDRKDLEGRLKAREDLLLPIYHQVAVQFADFHDTPGRMLEK
GVISDILEWKTARTFLYWRLRRLLLEDQVKQEILQASGELSHVHIQSMLRRWFVETEGA
VKAYLWDNNQVVVQWLEQHWQAGDGPRSTIRENITYLKHDSVLKTIRGLVEENPEVAV
DCVIYLSQHISPAERAQVVHLLSTMDSPAST
```

N1-PYRAZOLOSPIROKETONE ACETYL-COA CARBOXYLASE INHIBITORS

This application is a continuation of U.S. application Ser. No. 13/644,415 filed Oct. 4, 2012, which is a continuation of U.S. application Ser. No. 12/941,133 filed Nov. 8, 2010, now granted U.S. Pat. No. 8,288,405, which claims the benefit of priority from U.S. Provisional Application No. 61/259,823 filed Nov. 10, 2009, each of which are herein incorporated by reference.

FIELD OF THE INVENTION

This invention relates to substituted pyrazolospiroketone compounds that act as inhibitors of an acetyl-CoA carboxylase(s) and their use in treating diseases, conditions or disorders modulated by the inhibition of acetyl-CoA carboxylase enzyme(s).

BACKGROUND OF THE INVENTION

Acetyl-CoA carboxylases (ACC) are a family of enzymes found in most species and are associated with fatty acid synthesis and metabolism through catalyzing the production of malonyl-CoA from acetyl-CoA. In mammals, two isoforms of the ACC enzyme have been identified. ACC1, which is expressed at high levels in lipogenic tissues, such as fat and the liver, controls the first committed step in the biosynthesis of long-chain fatty acids. If acetyl-CoA is not carboxylated to form malonyl-CoA, it is metabolized through the Krebs cycle. ACC2, a minor component of hepatic ACC but the predominant isoform in heart and skeletal muscle, catalyzes the production of malonyl-CoA at the cytosolic surface of mitochondria, and regulates how much fatty acid is utilized in β-oxidation by inhibiting carnitine palmitoyl transferase. Thus, by increasing fatty acid utilization and by preventing increases in de novo fatty acid synthesis, chronic administration of an ACC inhibitor (ACC-I) may also deplete liver and adipose tissue triglyceride (TG) stores in obese subjects consuming a high or low-fat diet, leading to selective loss of body fat.

Studies conducted by Abu-Etheiga, et al., suggest that ACC2 plays an essential role in controlling fatty acid oxidation and, as such it would provide a target in therapy against obesity and obesity-related diseases, such as type-2 diabetes. See, Abu-Etheiga, L, et al., "Acetyl-CoA carboxylase 2 mutant mice are protected against obesity and diabetes induced by high-fat/high-carbohydrate diets" *PNAS* 100(18) 10207-10212 (2003). See also, Choi, C. S., et al., "Continuous fat oxidation in acetyl-CoA carboxylase 2 knockout mice increases total energy expenditure, reduces fat mass, and improves insulin sensitivity" *PNAS* 104(42) 16480-16485 (2007).

It is becoming increasingly clear that hepatic lipid accumulation causes hepatic insulin resistance and contributes to the pathogenesis of type 2 diabetes. Salvage, et al., demonstrated that ACC 1 and ACC2 are both involved in regulating fat oxidation in hepatocytes while ACC1, the dominant isoform in rat liver, is the sole regulator of fatty acid synthesis. Furthermore, in their model, combined reduction of both isoforms is required to significantly lower hepatic malonyl-CoA levels, increase fat oxidation in the fed state, reduce lipid accumulation, and improve insulin action in vivo. Thus, showing that hepatic ACC1 and ACC2 inhibitors may be useful in the treatment of nonalcoholic fatty liver disease (NAFLD) and hepatic insulin resistance. See, Savage, D. B., et al., "Reversal of diet-induced hepatic steatosis and hepatic insulin resistance by antisense oligonucleotide inhibitors of acetyl-CoA carboxylases 1 and 2" *J Clin Invest* doi: 10.1172/JC127300. See also, Oh, W., et al., "Glucose and fat metabolism in adipose tissue of acetyl-CoA carboxylase 2 knockout mice" *PNAS*, 102(5) 1384-1389 (2005).

Consequently, there is a need for medicaments containing ACC1 and/or ACC2 inhibitors to treat obesity and obesity-related diseases (such as, NAFLD and type-2 diabetes) by inhibiting fatty acid synthesis and by increasing fatty acid oxidation.

SUMMARY OF THE INVENTION

The present invention relates to compounds having the structure of Formula (I)

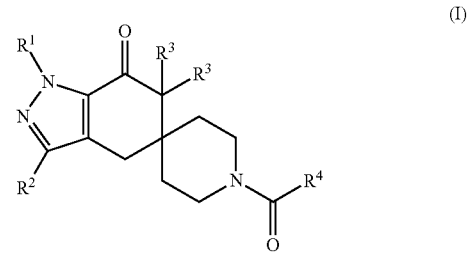

wherein $R^1$ is $(C_1-C_6)$alkyl, $(C_3-C_7)$cycloalkyl, tetrahydrofuranyl or oxetanyl; wherein said $(C_1-C_6)$alkyl is optionally substituted with 1 to 2 substituents independently selected from $(C_1-C_3)$alkoxy; hydroxy, halo, phenyl, tetrahydrofuranyl or oxetanyl;

$R^2$ is hydrogen, halo, $(C_1-C_3)$alkyl, cyano or $-C(=NH)(OCH_3)$;

$R^3$ are each independently hydrogen or $(C_1-C_3)$alkyl;

$R^4$ is $(C_6-C_{10})$aryl, 5 to 12 membered heteroaryl or 8 to 12 membered fused heterocyclicaryl; wherein said $(C_6-C_{10})$aryl, 5 to 12 membered heteroaryl or 8 to 12 membered fused heterocyclicaryl are each optionally substituted with one to three substituents independently selected from $(C_1-C_3)$alkyl, $(C_1-C_3)$alkoxy, halo, amino, $(C_1-C_3)$alkylamino, di$(C_1-C_3)$alkylamino, hydroxy, cyano, amido, phenyl, 5 to 6 membered heteroaryl or 5 to 6 membered heterocyclyl; or a pharmaceutically acceptable salt thereof.

A preferred embodiment of the present invention are compounds of Formula (I) wherein $R^4$ is $(C_6-C_{10})$ aryl selected from phenyl or naphthyl: a 5 to 12 membered heteroaryl selected from pyridinyl, pyrazolyl, pyrimidinyl, triazolyl, indolizinyl, indazolyl, pyrrolo[2,3-b]pyridinyl, pyrrolo[3,2-b]pyridinyl, pyrrolo[1,2-a]pyrazinyl, imidazo[1,2-a]pyridinyl, imidazo[1,5-a]pyridinyl, benzo[d]imidazolyl, pyrazolo[3,4-b]pyridinyl, pyrazolo[4,3-b]pyridinyl, pyrazolo[1,5-a]pyrimidinyl, benzo[d]imidazol-2-onyl, 1,6-naphthyridinyl, quinoxalinyl, quinolin-4-onyl or isoquinolin-1-onyl; or an 8 to 12 membered fused heterocyclicaryl selected from 3,4-dihydroquinolin-2-onyl or indolin-2-onyl; wherein each $R^4$ group is optionally substituted with one to four substituents independently selected from $(C_1-C_3)$alkyl, $(C_1-C_8)$alkoxy, halo, amino, $(C_1-C_3)$alkylamino, di$(C_1-C_3)$alkylamino, hydroxy, cyano, amido, phenyl, 5 to 6 membered heteroaryl or 5 to 6 membered heterocycyl; or a pharmaceutically acceptable salt thereof.

Another preferred embodiment of the present invention is the compound of Formula (I) wherein $R^1$ is $(C_1-C_6)$alkyl, $(C_3-C_7)$cycloalkyl, or tetrahydrofuranyl; and $R^2$ is hydrogen or methyl; or a pharmaceutically acceptable salt thereof. Yet another preferred embodiment of the present invention is the compound of formula (I) wherein $R^1$ is ethyl, isopropyl or t-butyl; and $R^4$ is phenyl, pyrazolyl, imidazolyl, triazolyl, pyridinyl, pyrimidinyl, indolyl, benzopyrazinyl, benzoimidazolyl, benzimidazolonyl, pyrrolopyridinyl, pyrrolopyrimidinyl, pyrazolopyridinyl, pyrazolopyrimidinyl, indazolyl, indolinonyl, naphthyridinyl, quinolinyl, quinolinonyl, dihydroquinolinonyl, oxo-dihydroquinolinonyl, isoquinolinyl, isoquinolinonyl, dihydroisoquinonyl or oxo-dihydroisoquinonyl, each optionally substituted with one to three substituents independently selected from fluoro, chloro, methyl, amino, methylamino, dimethylamino, amido, cyano, phenyl, imidazolyl, pyrazolyl, triazolyl, pyridinyl or morpholinyl; or a pharmaceutically acceptable salt thereof. A further preferred embodiment of the present invention is the compound of formula (I) wherein $R^1$ is isopropyl or t-butyl; $R^2$ is hydrogen; and each $R^3$ is hydrogen; or a pharmaceutically acceptable salt thereof. Yet another preferred embodiment of the present invention is the compound of formula (I) wherein $R^4$ is indazolyl, benzoimidazolyl, 1-oxo-1,2-dihydroisoquinolinyl, 1H-pyrrolo[3,2-b]pyridinyl, 2-oxo-2,3-dihydro-1H-benzo[d]imidazolyl, 1H-pyrazolylphenyl, 1H-pyrazolylpyridinyl, or 1H-imidazolylphenyl; each optionally substituted with one to two methyl, chloro or fluoro; or a pharmaceutically acceptable salt thereof.

Another preferred embodiment of the present invention is a compound selected from 1-isopropyl-1'-(1-oxo-1,2-dihydroisoquindine-6-carbonyl)-4,6-dihydrospiro[indazole-5,4'-piperidin]-7(1H)-one: 1-isopropyl-1'-(1H-pyrrolo[3,2-b]pyridine-6-carbonyl)-4,6-dihydrospiro[indazole-5,4'-piperidin]-7(1H-one; 1-(tert-butyl)-1'-(2-methyl-3H-benzo[d]imidazole-5-carbonyl)-4,6-dihydrospiro[indazole-5,4'-piperidin]-7(1H)-one; 1-(tert-butyl)-1'-(1H-pyrrolo[3,2-b]pyridine-6-carbonyl)-4,6-dihydrospiro[indazole-5,4'-piperidin]-7(1H)-one; 1-(tert-butyl)-1'-(1H-indazole-5-carbonyl)-4,6-dihydrospiro[indazole-5,4'-piperidin]-7(1H)-one; 1-(tert-butyl)-1'-(2-oxo-2,3-dihydro-1H-benzo[d]imidazole-5-carbonyl)-4,6-dihydrospiro[indazole-5,4'-piperidin]-7(1H)-one; 1-isopropyl-1'-(2-oxo-2,3-dihydro-1H-benzo[d]imidazole-5-carbonyl)-4,6-dihydrospiro[indazole-5,4'-piperidin]-7(1H)-one; 1'-(7-fluoro-1H-indazole-5-carbonyl)-isopropyl-4,6-dihydrospiro[indazole-5,4'-piperidin]-7(1H)-one; 1-isopropyl-1'-(1-methyl-2-oxo-2,3-dihydro-1H-benzo[d]imidazole-5-carbonyl)-4,6-dihydrospiro[indazole-5,4'-piperidin]-7(1H)-one; 1'-(7-chloro-2-methyl-3H-benzo[d]imidazole-5-carbonyl)-1-isopropyl-4,6-dihydrospiro[indazole-5,4'-piperidin]-7(1H one; 1'-(1H-indazole-6-carbonyl)-1-isopropyl-4,6-dihydrospiro[indazole-5,4'-piperidin]-7(1H)-one; 1-isopropyl-1'-(3-(1H-pyrazol-4-yl)benzoyl)-4,6-dihydrospiro[indazole-5,4'-piperidin]-7(1H-one; 1-isopropyl-1'-(2-methyl-1H-benzo[d]imidazole-5-carbonyl)-4,6-dihydrospiro[indazole-5,4'-piperidin]-7(1H)-one; 1'-(1H-indazole-5-carbonyl)-1-isopropyl-4,6-dihydrospiro[indazole-5,4'-piperidin]-7(1H)-one; 1'-(1H-indazole-5-carbonyl)-1-isopropyl-3-methyl-4,6-dihydrospiro[indazole-5,4'-piperidin]-7(1H)-one; 1-(tert-butyl)-1'-(2-(1H-pyrazol-3-yl)pyridine-4-carbonyl)-4,6-dihydrospiro[indazole-5,4'-piperidin]-7(1H)-one; 1-(tert-butyl)-1'-(3-(1H-pyrazol-3-yl)benzoyl)-4,6-dihydrospiro[indazole-5,4'-piperidin]-7(1H)-one; 1-isopropyl-1'-(1H-pyrrolo[3,2-b]pyridine-2-carbonyl)-4,6-dihydrospiro[indazole-5,4'-piperidin]-7(1H)-one; 1-(tert-butyl)-1'-(4-(1H-imidazol-2-yl)benzoyl)-4,6-dihydrospiro[indazole-5,4'-piperidin]-7(1H)-one; 1-(tert-butyl-1'-(3-(1H-imidazol-2-yl)benzoyl)-4,6-dihydrospiro[indazole-5,4'-piperidin]-7(1H)-one; or 1-(tert-butyl)-1'-(1H-indazole-6-carbonyl-4,6-dihydrospiro[indazole-5,4'-piperidin]-7(1H)-one; or a pharmaceutically acceptable salt thereof.

Another aspect of the present invention is a pharmaceutical composition comprising an amount of a compound of formula (I) as described in any of the embodiments; or a pharmaceutically acceptable salt thereof and a pharmaceutically acceptable excipient, diluent, or carrier. Preferably, the composition comprises a therapeutically effective amount of a compound of the present invention or a pharmaceutically acceptable salt thereof. The composition may also contain at least one additional pharmaceutical agent. Preferred agents include anti-diabetic agents and/or anti-obesity agents (described herein below).

In yet another aspect of the present invention is a method for treating a disease, condition, or disorder mediated by the inhibition of acetyl-CoA carboxylase enzyme(s) in a mammal that includes the step of administering to a mammal, preferably a human, in need of such treatment a therapeutically effective amount of a compound of the present invention or a pharmaceutically acceptable salt thereof, or a pharmaceutical composition thereof.

Diseases, disorders, or conditions mediated by inhibitors of acetyl-CoA carboxylases include Type II diabetes and diabetes-related diseases, such as nonalcoholic fatty liver disease (NAFLD), hepatic insulin resistance, hyperglycemia, metabolic syndrome, impaired glucose tolerance, diabetic neuropathy, diabetic nephropathy, diabetic retinopathy, obesity, dyslipidemia, hypertension, hyperinsulinemia, and insulin resistance syndrome. Preferred diseases, disorders, or conditions include Type II diabetes, nonalcoholic fatty liver disease (NAFLD), hepatic insulin resistance, hyperglycemia, impaired glucose tolerance, obesity, and insulin resistance syndrome. More preferred are Type II diabetes, nonalcoholic fatty liver disease (NAFLD), hepatic insulin resistance, hyperglycemia, and obesity. Most preferred is Type II diabetes.

A preferred embodiment is a method for treating, (e.g. delaying the progression or onset) of Type 2 diabetes and diabetes-related disorders in animals comprising the step of administering to an animal in need of such treatment a therapeutically effective amount of a compound of the present invention or a pharmaceutically acceptable salt thereof or a composition thereof.

Another preferred embodiment is a method for treating obesity and obesity-related disorders in animals comprising the step of administering to an animal in need of such treatment a therapeutically effective amount of a compound of the present invention or a pharmaceutically acceptable salt thereof or a composition thereof.

Yet another preferred embodiment is a method for treating nonalcoholic fatty liver disease (NAFLD) or hepatic insulin resistance in animals comprising the step of administering to an animal in need of such treatment a therapeutically effective amount of a compound of the present invention or a pharmaceutically acceptable salt thereof or a composition thereof.

Compounds of the present invention may be administered in combination with other pharmaceutical agents (in particular, anti-obesity and anti-diabetic agents described herein below). The combination therapy may be administered as (a) a single pharmaceutical composition which comprises a compound of the present invention or a pharmaceutically acceptable salt thereof, at least one additional pharmaceutical agent described herein and a pharmaceutically acceptable excipient, diluent, or carrier; or (b) two separate pharmaceutical compositions comprising (i) a first composition comprising a compound of the present invention or a pharmaceutically acceptable salt thereof and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

BRIEF DESCRIPTION OF THE DRAWINGS

FIG. 1 SEQ. ID NO. 1 provides a sequence of recombinant human ACC1 (SEQ. ID NO. 1) that can be employed in the Transcreener in vitro assay.

FIG. 2 SEQ. ID NO. 2 provides a sequence of recombinant human ACC2 (SEQ. ID NO. 2) that can be employed in the Transcreener in vitro assay.

DETAILED DESCRIPTION OF THE INVENTION

Definitions

The phrase "therapeutically effective amount" means an amount of a compound of the present invention or a pharmaceutically acceptable salt thereof that: (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated" or "modulating", or "modulate(s)", as used herein, unless otherwise indicated, refers to the inhibition of the Acetyl-CoA carboxylases (ACC) enzyme(s) with compounds of the present invention.

The terms "mediated" or "mediating" or "mediate(s)", as used herein, unless otherwise indicated, refers to the (i) treatment or prevention the particular disease, condition, or disorder, (ii) attenuation, amelioration, or elimination of one or more symptoms of the particular disease, condition, or disorder, or (iii) prevention or delay of the onset of one or more symptoms of the particular disease, condition, or disorder described herein, by inhibiting the Acetyl-CoA carboxylases (ACC) enzyme(s).

The term "compounds of the present invention" (unless specifically identified otherwise) refer to compounds of Formula (I) and any pharmaceutically acceptable salts of the compounds, as well as, all stereoisomers (including diastereoisomers and enantiomers), tautomers, conformational isomers, and isotopically labeled compounds. Hydrates and solvates of the compounds of the present invention are considered compositions of the present invention, wherein the compound is in association with water or solvent, respectively.

The terms "$(C_1-C_6)$alkyl" and "$(C_1-C_3)$alkyl" are alkyl groups of the specified number of carbons, from one to six or one to three carbons, respectively, which can be either straight chain or branched. For example, the term "$(C_1-C_3)$alkyl" has from one to three carbons and consists of methyl, ethyl, n-propyl and isopropyl.

The term "$(C_3-C_7)$cycloalkyl" means a cycloalkyl group with three to seven carbon atoms and consists of cyclopropyl, cyclobutyl, cyclopentyl, cyclohexyl and cycloheptyl. The term "halo" means fluoro, chloro, bromo or iodo. The term "$(C_6-C_{10})$aryl" means an aromatic carbocyclic group consisting of six to ten carbon atoms such as phenyl or naphthyl.

The term "5 to 12 membered heteroaryl" means a five to twelve membered aromatic group which contains at least one heteroatom selected from nitrogen, oxygen and sulfur. As used herein the point of attachment of the "5 to 12 membered heteroaryl" group is on a carbon atom of that group. The "5 to 12 membered heteroaryl" group can be either monocyclic or bicyclic. Preferred embodiments of monocyclic heteroaryls include, but are not limited to, pyrazolyl, imidazolyl, triazolyl, pyridinyl, and pyrimidinyl. Preferred embodiments of bicyclic heteroaryls include, but are not limited to, radicals of the following ring systems:

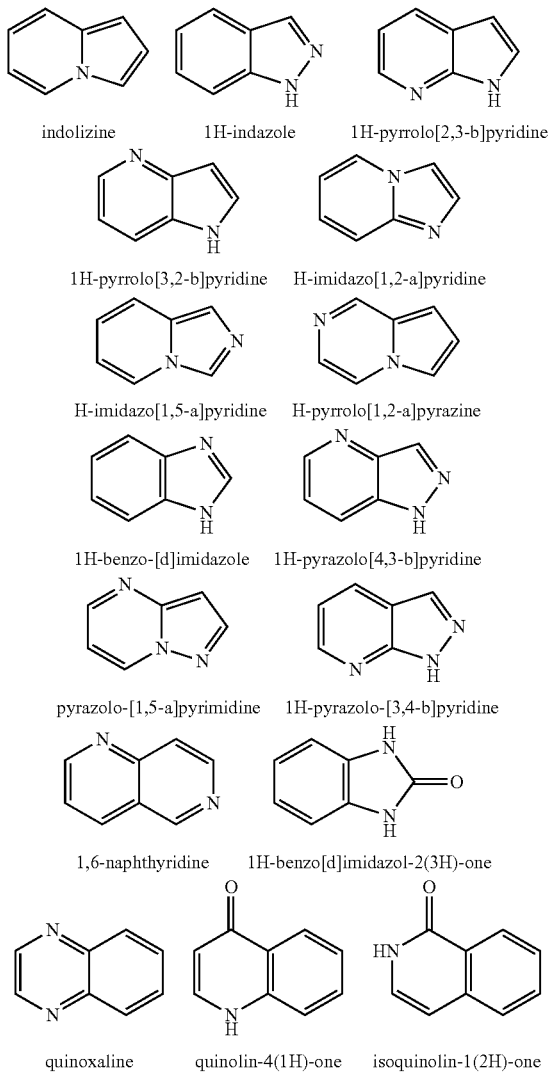

The term "8 to 12 membered fused heterocyclicaryl" means an 8 to 12 membered ring system in which a non-aromatic heterocyclic ring is fused to an aryl ring. As used herein the point of attachment of the "8 to 12 membered fused heterocyclicaryl" group is on a carbon atom of that group. A preferred embodiment includes radicals of ring systems such as:

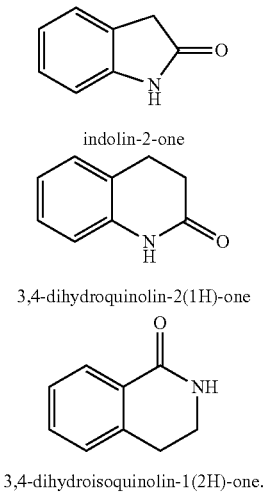

indolin-2-one 3,4-dihydroquinolin-2(1H)-one 3,4-dihydroisoquinolin-1(2H)-one.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). Similarly, a "hydroxy-protecting group" refers to a substituent of a hydroxy group that blocks or protects the hydroxy functionality. Suitable hydroxyl-protecting groups (O-Pg) include for example, allyl, acetyl, silyl, benzyl, para-methoxybenzyl, trityl, and the like. The need for such protection is readily determined by one skilled in the art. For a general description of protecting groups and their use, see T. W. Greene, *Protective Groups in Organic Synthesis*, John Wiley & Sons, New York, 1991.

The following reaction schemes, Reaction Scheme I through Reaction Scheme IV provide representative procedures that are used to prepare the compounds of Formula (I). It is to be understood that these reaction schemes are to be construed in a non-limiting manner and that reasonable variations of the depicted methods can be used to prepare the compounds of Formula (I).

Reaction Scheme I outlines the general procedures one could use to provide compounds of the present invention having Formula (Ia) which are compounds of Formula (I) in which $R^2$ and each $R^3$ are each hydrogen. The protected spiropiperidine derivative (VIIIa) may be formed by treating the appropriately protected piperidine aldehyde (Xa) with methyl vinyl ketone (IXa). The group Pg represents an appropriate amine protecting group and is preferably N-tert-butoxycarbonyl (BOC) or carbobenzyloxy (Cbz). This reaction can be carried out in the presence of ethanolic potassium hydroxide according to a procedure analogous to that described by Roy, S. et al., *Chem. Eur. J.* 2006, 12, 3777-3788 at 3786. Alternatively, the reaction can be carried out in the presence of para-toluenesulfonic acid (pTSA) in refluxing benzene to provide the desired product (VIIIa).

Reaction Scheme I

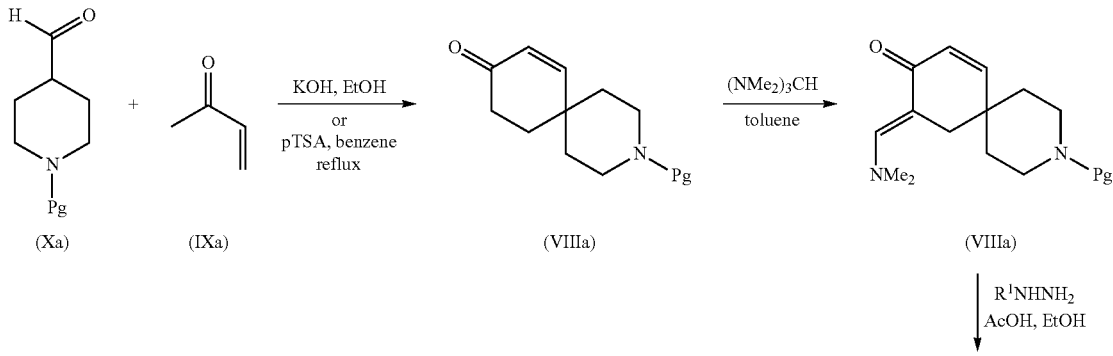

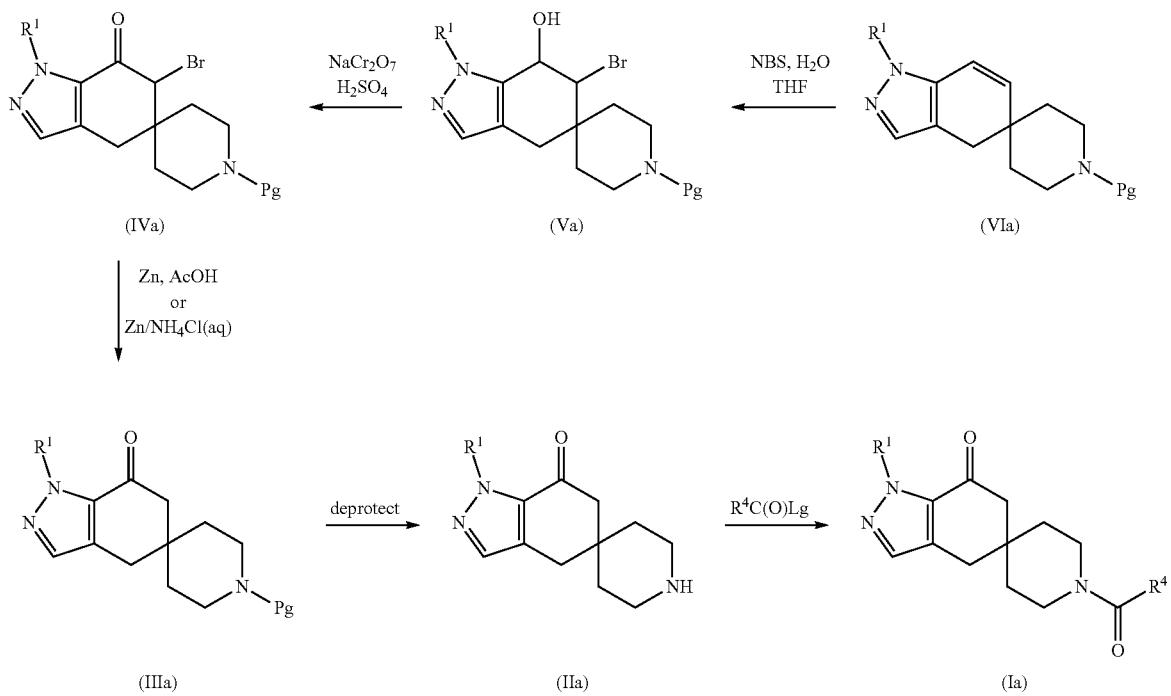

The spiropiperidine derivative (VIIIa) can then be reacted with tris-(N,N-dimethylamino)methane in refluxing toluene to provide the enamine functionalized spiropiperidine derivative (VIIa). Alternatively, the enamine (VIIa) may be prepared by reacting spiropiperidine (VIIIa) with N,N-dimethylformamide dimethyl acetal as solvent at reflux. This reaction may also be run in an alcoholic solvent such as 2-propanol, an aromatic hydrocarbon solvent such as toluene or a polar aprotic solvent such as N,N-dimethylformamide. Additionally, this reaction may be catalyzed by the addition of 4-toluenesulfonic acid, tris(dimethylamino)methane, or various bases such as lithium hydroxide, DBU and N,N-diisopropylethylamine. This transformation may also be performed with, or by reaction with, t-butoxy bis(dimethylamino)methane in toluene at reflux.

Compound (VIIa) is then reacted with an appropriate hydrazine derivative $R^1NHNH^2$ in the presence of acetic acid in refluxing ethanol or toluene to provide the desired cyclized compound of formula (VIa) (see Murali Dhar, T. G. et al. *Bioorg. Med. Chem. Lett.* 2007, 17, 5019-5024 at 5020). The compound of formula (VIa) can then be treated with N-bromosuccinimide (NBS) in the presence of water in THF to provide the corresponding bromo hydroxy derivative of formula (Va). The bromo hydroxy derivative (Va) is then oxidized with Jones reagent in a method analogous to that provided in Wolinsky, J. et al., *J. Org. Chem.* 1978, 43(5). 875-881 at 876, 879 to provide the α-bromo keto derivative of formula (IVa). Alternatively the oxidation of (Va) can be performed with catalytic tetrapropylammonium perruthenate and N-methylmorpholine N-oxide. The compound of formula (IVa) can then be debrominated using conventional methods such as treatment with zinc and acetic acid or, alternatively, zinc in the presence of aqueous ammonium chloride in tetrahydrofuran to provide the compound of formula (IIIa).

The compound of formula (IIIa) can then be deprotected to provide the free spiropiperidine derivative of formula (IIa) using standard methods which depend on which protecting group Pg has been employed. For example, when Pg represents tert-butyloxycarbonyl (BOC) standard strong acid deprotection conditions such as 4N hydrochloric acid in dioxane or trifluoroacetic acid in an appropriate solvent such as dichloromethane can be used to remove the BOC group. When Pg represents carbobenzyloxy (Cbz), hydrogenation over palladium on carbon in ethanol or treatment with a hydrogen source such as ammonium formate or 1-methyl-1,4-cyclohexadiene in the presence of palladium on carbon in ethanol or ethyl acetate can be employed to carry out the deprotection.

The spiropiperidine derivative of Formula (IIa) can then be acylated by employing standard methods to provide the compound of Formula (Ia). For example, the compound (Ia) may then be formed using a standard peptide coupling reaction with the desired carboxylic acid ($R^4CO_2H$). For example, the spiropiperidine intermediate (IIa) and carboxylic acid ($R^4CO_2H$) may be coupled by forming an activated carboxylic acid ester, such as by contacting the carboxylic acid ($R^4CO_2H$) with a peptide coupling reagent, such as O-(7-azabenzotriazol-1-yl)-N,N,N',N'-tetramethyluronium hexafluorophosphate (HATU) or 1-ethyl-3-(3-dimethylaminopropyl)carbodiimide hydrochloride (EDC HCl), in the presence or absence of an activating agent, such as hydroxybenzotriazole (HOBt) and in the presence of a suitable base, such as N,N-diisopropylethylamine (DIEA), triethylamine or N-methylmorpholine (NMM), in a suitable solvent such as THF and/or DMF, dimethylacetamide (DMA) or dichloromethane and then contacting the activated carboxylic acid ester with the spiropiperidine derivative (IIa) to form a compound of Formula (Ia).

Alternatively, compounds of Formula (Ia) can be formed by first converting the carboxylic acid ($R^4CO_2H$) to an acid chloride ($R^4COCl$), such as by reading with thionyl chloride, and then reacting the acid chloride with the spiropiperidine derivative (IIa) in the presence of an appropriate base such as triethylamine in an appropriate solvent such as dichloromethane to form a compound of Formula (Ia). Still another alternative method entails treating the carboxylic acid ($R^4CO_2H$) with 2-chloro-4,6-dimethoxytriazine in the presence of a suitable base, such as N-methylmorpholine in a suitable solvent such as THF and/or DMF. To the activated ester is added a solution of the spiropiperidine derivative (IIa) and base, such as N-methylmorpholine, in a suitable solvent, such as THF and/or DMF which then provides the compound of Formula (Ia).

Reaction Scheme II provides an alternative synthesis of compounds of Formula (Ia) starting from the intermediate of Formula (VIa). The compound of Formula (VIa) is treated with N-bromosuccinimide (NBS) in the presence of methanol in THF, or preferably in methanol, (Nishimura, T. et al. Org. Lett. 2008, 10(18), 4057-4060 at 4059) to provide the methoxy bromo spiropiperidine derivative of Formula (Vb). Base induced elimination of the compound of Formula (Vb) by treatment with a strong base such as potassium tert-butoxide in THF provides the compound of Formula (IVb) which is then treated with a strong acid such as 2N hydrochloric acid in THF to provide the compound of Formula (IIIa). The compound of Formula (IIa) can then be deprotected and acylated as described previously in Reaction Scheme I to provide compounds of Formula (Ia).

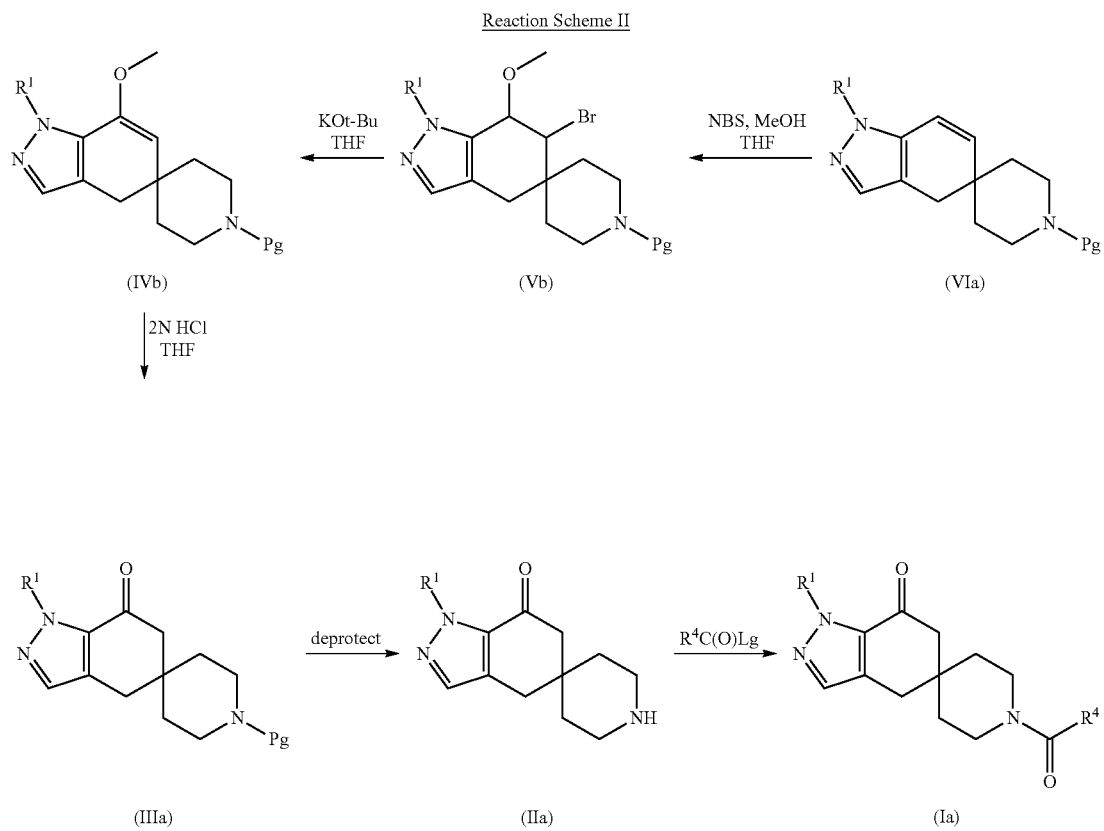

Reaction Scheme III provides a synthesis of compounds of Formula (Ib) which are compounds of Formula (I) in which $R^2$ is bromo and each $R^3$ is hydrogen. The compound of Formula (VIa) is reacted with approximately two equivalents of N-bromosuccinimide in the presence of methanol to provide the dibromo methoxy spiropiperidine derivative of Formula (Vc). The compound of Formula (Vc) is then subjected to elimination conditions by treatment with a strong base such as potassium tert-butoxide in an appropriate solvent to provide the compound of Formula (IVc). Treatment of the compound of formula (IVc) with strong acid such as 2N hydrochloric acid provides the compound of Formula (IIIb). Deprotection of the compound of Formula (IIIb) to provide the compound of Formula (IIb) followed by acylation to provide the compound of Formula (b) can be carried out as described previously for Reaction Scheme 1.

Reaction Scheme III

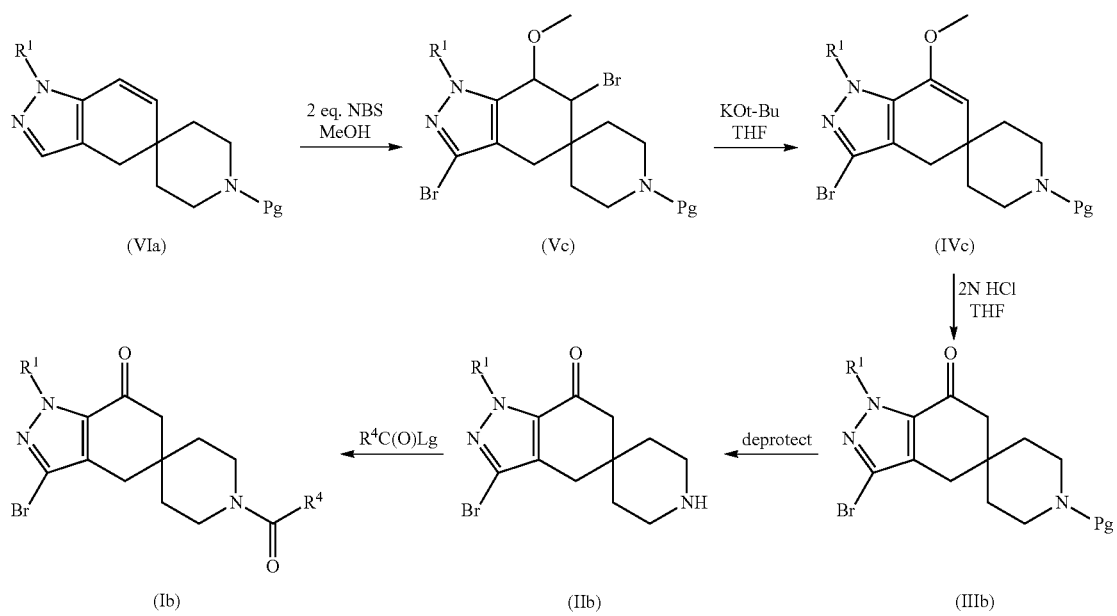

Reaction Scheme IV depicts the preparation of certain other compounds within Formula (I) from certain of the intermediates previously depicted. The first transformation in Reaction Scheme IV shows introduction of a methyl group at the $R^2$ position by reacting the bromo spiropiperidine derivative of Formula (IIIb) with trimethylboroxine in dimethylformamide in the presence of an appropriate palladium catalyst, such as palladium tetrakis triphenylphosphine in the presence of potassium carbonate and water to provide the compound of Formula (IIIc). Other alkyl groups can be introduced at the $R^2$ position in an analogous manner. The compound of Formula (IIIc) can then be deprotected and acylated as previously described. The second transformation in Reaction Scheme IV depicts the introduction of a cyano group at the $R^2$ position. The bromo spiropiperidine compound (IIIb) is reacted with zinc cyanide in the presence of zinc and an appropriate palladium catalyst to provide the compound of Formula (IIId) which can then be deprotected and acylated to provide a compound of Formula (Id). The third transformation in Reaction Scheme IV depicts introduction of an appropriate group at the $R^3$ position of the compound of Formula (IIIe). The compound of Formula (IIIe) is deprotonated with a strong base, such as lithium hexamethyldisilazide (LHMDS) under appropriate anhydrous conditions in an appropriate solvent, preferably at low temperature. The enolate thus formed is then reacted with an appropriate electrophile $R^3Lg$ wherein Lg represents an appropriate leaving group (such as a halide when $R^3Lg$ is an alkyl halide) to provide the compound of Formula (IIIf) wherein $R^3$ is an appropriate group such as an alkyl group. The deprotonation of the compound of Formula (IIIf) and reaction with another $R^3Lg$ can then be carried out again if desired. The compound of Formula (IIIf) can then be deprotected and acylated as previously described to provide the compound of Formula (Ie).

Reaction Scheme IV

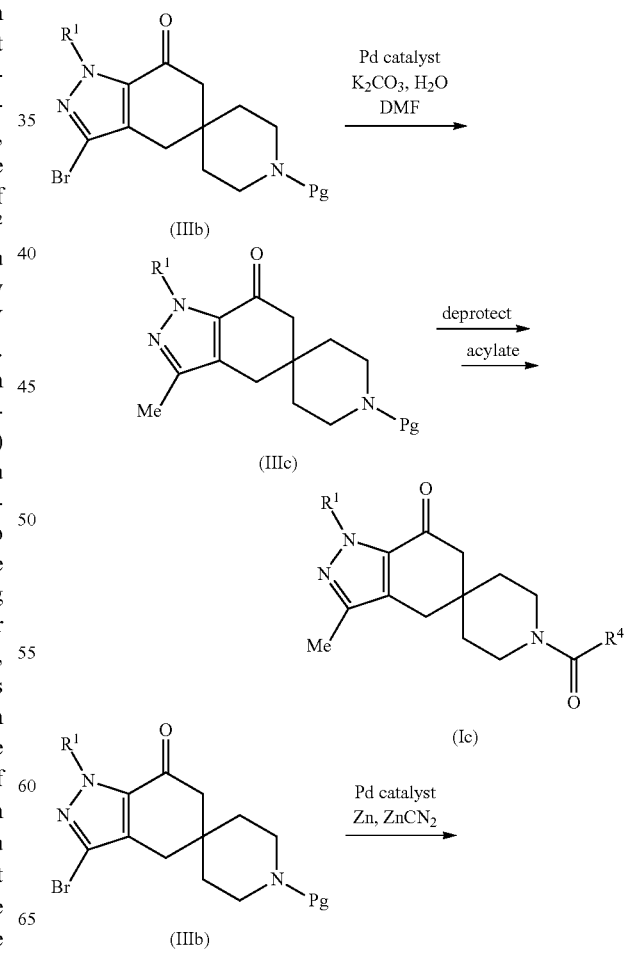

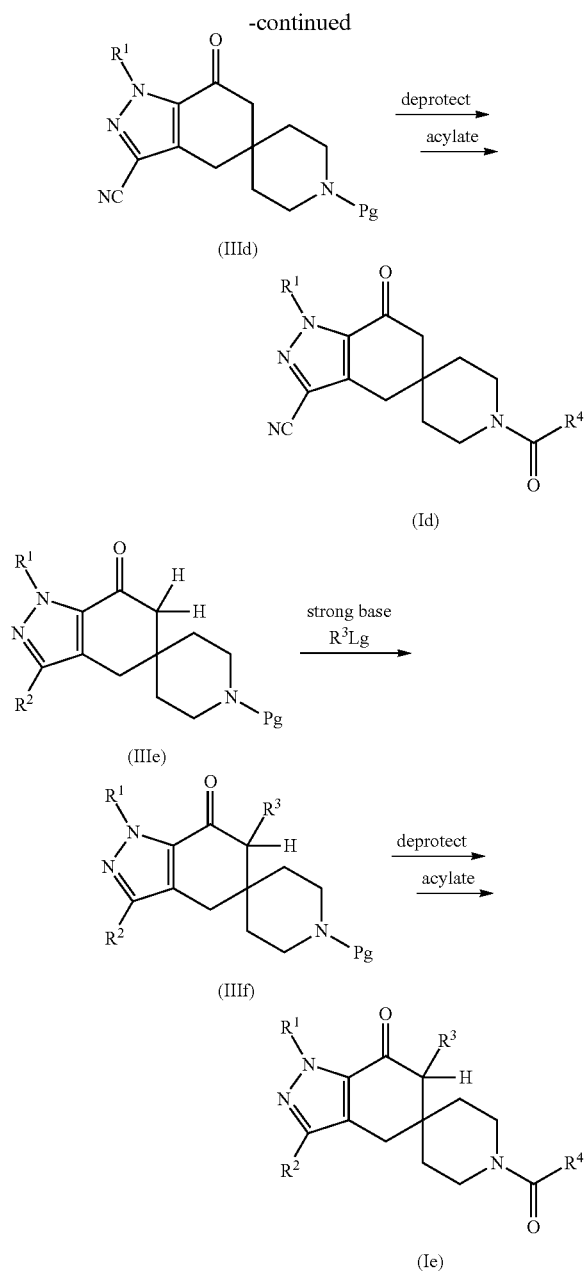

The compounds of the present invention may be isolated and used per se or in the form of their pharmaceutically acceptable salts. In accordance with the present invention, compounds with multiple basic nitrogen atoms can form salts with varying number of equivalents ("eq.") of acid. It will be understood by practitioners that all such salts are within the scope of the present invention.

Pharmaceutically acceptable salts, as used herein in relation to compounds of the present invention, include pharmaceutically acceptable inorganic and organic salts of the compound. These salts can be prepared in situ during the final isolation and purification of a to compound, or by separately reacting the compound thereof, with a suitable organic or inorganic acid and isolating the salt thus formed. Representative salts include, but are not limited to, the hydrobromide, hydrochloride, hydroiodide, sulfate, bisulfate, nitrate, acetate, trifluoroacetate, oxalate, besylate, palmitate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate and laurylsulphonate salts, and the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylammonium, dimethylammonium, trimethylammonium, triethylammonium, ethylammonium, and the like. For additional examples see, for example, Berge, et al., J. Pharm. Sci., 66, 1-19 (1977).

Compounds of the present invention may exist in more than one crystal form. Polymorphs of compounds of Formula (I) and salts thereof (including solvates and hydrates) form part of this invention and may be prepared by crystallization of a compound of the present invention under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of the present invention followed by gradual or fast cooling. The presence of polymorphs may be determined by solid probe nuclear magnetic resonance (NMR) spectroscopy, infrared (IR) spectroscopy, differential scanning calorimetry, powder X-ray diffraction or such other techniques.

This invention also includes isotopically-labeled compounds, which are identical to those described by Formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur and fluorine, such as $^2H$, $^3H$, $^{13}C$, $^{14}C$, $^{15}N$, $^{18}O$, $^{17}O$, $^{35}S$, $^{36}Cl$, $^{125}I$, $^{129}I$, and $^{18}F$ respectively. Certain isotopically-labeled compounds of the present invention, for example those into which radioactive isotopes such as $^3H$ and $^{14}C$ are incorporated, are useful in drug and/or substrate tissue distribution assays. Tritiated (i.e., $^3H$), and carbon-14 (i.e., $^{14}C$), isotopes are particularly preferred for their ease of preparation and detectability. Further, substitution with heavier isotopes such as deuterium (i.e., $^2H$), can afford certain therapeutic advantages resulting from greater metabolic stability, for example increased in vivo half-life or reduced dosage requirements and, hence, may be preferred in some circumstances. Isotopically labeled compounds of the present invention can generally be prepared by carrying out the procedures disclosed in the schemes and/or in the Examples below, by substituting a readily available isotopically labeled reagent for a non-isotopically labeled reagent.

The compounds of the present invention may contain stereogenic centers. These compounds may exist as mixtures of enantiomers or as pure enantiomers. When the compound includes a stereogenic center, the compound may be resolved into the pure enantiomers by methods known to those skilled in the art, for example by formation of diastereoisomeric salts which may be separated, for example, by crystallization; formation of stereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, the specific stereoisomers may be synthesized by using an optically active starting material, by asymmetric synthesis using optically active reagents, substrates, catalysts or solvents, or by converting one stereoisomer into the other by asymmetric transformation.

Compounds of the present invention may exist in different stable conformational forms which may be separable. Torsional asymmetry due to restricted rotation about an asymmetric single bond, for example because of steric hindrance or ring strain, may permit separation of different conformers. The compounds of the present invention further include each conformational isomer of compounds of Formula (I) and mixtures thereof.

Compounds of the present invention are useful for treating diseases, conditions and/or disorders modulated by the inhibition of the acetyl-CoA carboxylases enzyme(s) (in particular, ACC1 and ACC2). Another embodiment of the present invention is a pharmaceutical composition comprising a therapeutically effective amount of a compound of the present invention or a pharmaceutically acceptable salt thereof and a pharmaceutically acceptable excipient, diluent or carrier. The compounds of the present invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or a pharmaceutically acceptable salt thereof or a pharmaceutical composition thereof) or aid in the manufacturing of the pharmaceutical product (i.e., for use in medicine such as preparing a medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The dissolution rate of poorly water-soluble compounds may be enhanced by the use of a spray-dried dispersion, such as those described by Takeuchi, H., et al. in "Enhancement of the dissolution rate of a poorly water-soluble drug (tolbutanide) by a spray-drying solvent deposition method and disintegrants" *J. Pharm. Pharmacol.*, 39, 769-773 (1987); and EP0901786 B1 (US2002/009494), incorporated herein by reference. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of the present invention. The term "solvate" refers to a molecular complex of a compound represented by Formula (I) (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like. The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by the inhibition of the acetyl-CoA carboxylases enzyme(s) in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from the inhibition of acetyl-CoA carboxylases enzyme(s).

One aspect of the present invention is the treatment of obesity, and obesity-related disorders (e.g., overweight, weight gain, or weight maintenance). Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Another aspect of the present invention is for the treatment or delaying the progression or onset of diabetes or diabetes-related disorders including Type I (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, and diabetic complications (such as atherosclerosis, coronary heart disease, stroke, peripheral vascular disease, nephropathy, hypertension, neuropathy, and retinopathy).

In yet another aspect of the present invention is the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on Metabolic Syndrome, see, e.g., Zimmet, P. Z, et al., "The Metabolic Syndrome: Perhaps an Etiologic Mystery but Far From a Myth—Where Does the International Diabetes Federation Stand?," *Diabetes & Endocrinology*, 7(2), (2005); and Alberti, K. G., et al., "The Metabolic Syndrome—A New Worldwide Definition," *Lancet*, 366, 1059-62 (2005). Preferably, administration of the compounds of the present invention provides a statistically significant (p<0.05) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant (p<0.05) reduction in glucose serum levels.

In yet another aspect of the invention is the treatment of nonalcoholic fatty liver disease (NAFLD) and hepatic insulin resistance.

For a normal adult human having a body weight of about 100 kg, a dosage in the range of from about 0.001 mg to about 10 mg per kilogram body weight is typically sufficient preferably from about 0.01 mg/kg to about 5.0 mg/kg, more preferably from about 0.01 mg/kg to about 1 mg/kg. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of the present invention may also be used in conjunction with other pharmaceutical agent(s) for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable anti-obesity agents include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $\beta_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in US Publication 200610178501), opioid antagonists (e.g., naltrexone), oleoyl-estrone (CAS No. 180003-17-2), obinepitide (TM30338), pramlintide (Symlin), tesofensine (NS2330), leptin, liraglutide, bromocriptine, orlistat, exenatide (Byetta®), AOD-9604 (CAS No. 221231-10-3) and sibutramine. Preferably, compounds of the present invention and combination therapies are administered in conjunction with exercise and a sensible diet.

Suitable anti-diabetic agents include a sodium-glucose co-transporter (SGLT) inhibitor, a phosphodiesterase (PDE)-10 inhibitor, a diacylglycerol acyltransferase (DGAT) 1 or 2 inhibitor, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, migitol, voglibose, preadimicin-Q, and salbostatin), a PPARγ agonist (e.g., balaglitazone, ciglitazone, darglitazone, englitazone, isagitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) agonist (e.g., Byetta™, exendin-3 and exendin-4), a protein tyrosine phosphatase-1B (PTP-1B) inhibitor (e.g., trodusquemine, hyrtiosal extract, and compounds disclosed by Zhang, S., et al., *Drug Discovery Today*, 12(9/10), 373-381 (2007)), SIRT-1 inhibitor (e.g., reservatrol), a dipeptidyl peptidease IV (DPP-IV) inhibitor (e.g., sitagliptin, vildagliptin, alogliptin and saxagliptin), an insulin secreatagogue, a fatty acid oxidation inhibitor, an A2 antagonist, a c-jun amino-terminal kinase (JNK) inhibitor, insulin, an insulin mimetic, a glycogen phosphorylase inhibitor, a VPAC2 receptor agonist and a glucokinase activator. Preferred anti-diabetic agents are metformin, a glucagon-like peptide 1 (GLP-1) agonist (e.g, Byetta™) and DPP-IV inhibitors (e.g., sitagliptin, vildagliptin, alogliptin and saxagliptin).

All of the recited U.S. patents and publications, including all technical bulletins referenced in the Examples, are incorporated herein by reference in their entireties.

The Examples set forth herein below are for illustrative purposes only. The compositions, methods, and various parameters reflected herein are intended only to exemplify various aspects and embodiments of the invention, and are not intended to limit the scope of the claimed invention in any way.

EXAMPLES

The compounds and intermediates described below were generally named according to the IUPAC (International Union for Pure and Applied Chemistry) recommendations on Nomenclature of Organic Chemistry and the CAS Index rules. Unless noted otherwise, all reactants were obtained commercially.

Flash chromatography was performed according to the method described by Still et al., J. Org. Chem., 1978, 43, 2923.

All Biotage® purifications, discussed herein, were performed using either a 40M or 40S Biotage® column containing KP-SIL silica (40-63 µM, 60 Angstroms) (Biotage AB; Uppsala, Sweden).

All CombiFlash® purifications, discussed herein, were performed using a CombiFlash® Companion system (Teledyne Isco; Lincoln, Nebr.) utilizing packed RediSep® silica columns Mass Spectra were recorded on a Waters (Waters Corp.; Milford, Mass.) Micromass Platform II spectrometer. Unless otherwise specified, mass spectra were recorded on a Waters (Milford, Mass.) Micromass Platform II spectrometer.

Proton NMR chemical shifts are given in parts per million downfield from tetramethylsilane and were recorded on a Varian Unity 400 or 500 MHz (megaHertz) spectrometer (Varian Inc.; Palo Alto, Calif.). NMR chemical shifts are given in parts per million downfield from tetramethylsilane (for proton) or fluorotrichloromethane (for fluorine).

The preparations described below were used in the synthesis of compounds exemplified in the following examples.

Preparation of Starting Materials and Intermediates

Carboxylic Acid Starting Materials

The following commercially available carboxylic acids were used to prepare exemplified compounds of the present invention: 4-chloro-3-methylbenzoic acid (Alfa Aesar, Ward Hill, Mass.), 1H-pyrazolo[3,4-b]pyridine-5-carboxylic acid (Sphinx Scientific Laboratory Product List), 1-methyl-1H-indazole-6-carboxylic acid (PharmaBlock R & D Product List), 1H-benzimidazole-5-carboxylic acid (Affinitis Pharma LLC, New Haven, Conn.). 1H-indazole-5-carboxylic acid (Tyger Sdentific, Inc., Ewing, N.J.), 4-amino-2-methylpyrimidine-5-carboxylic acid (Tyger Scientific, Inc., Ewing, N.J.), 2-(methylamino)isonicotinic acid (Aurora Building Blocks), 1H-pyrrolo[3,2-b]pyridine-6-carboxylic acid (Matrix Scientific), 2-methyl-1H-benzimidazole-5-carboxylic acid (Apollo Scientific Intermediates for Research and Development), 7H-pyrrolo[2,3-b]pyridine-2-carboxylic acid (Ryan Scientific Product List), 1H-pyrrolo[2,3-b]pyridine-5-carboxylic acid (Matrix Scientific), 2-oxoindoline-5-carboxylic acid (Apollo Scientific Intermediates for Research and Development), 2-oxo-2,3-dihydro-1H-benzimidazole-5-carboxylic acid (AKos Building Blocks Product List), 2-oxo-1,2,3,4-tetrahydroquinoline-7-carboxylic acid (AKos Building Blocks Product List), 2-amino-1,6-naphthyridine-3-carboxylic acid (ACES Pharma Product List), 3-aminoquinoxaline-2-carboxylic acid (AsisChem Screening Library), 7-aminopyrazolo[1,5-a]pyrimidine-6-carboxylic acid (Ryan Scientific Product List), 1-methyl-2-oxo-2,3-dihydro-1H-benzimidazole-5-carboxylic acid (AKos Building Blocks Product List), 4-(1H-imidazol-2-yl)benzoic acid (Sphinx Scientific Laboratory Product List), 3-(1H-imidazol-4-yl)benzoic acid (Apollo Scientific Intermediates for Research and Development), 5-amino-2-phenyl-2H-1,2,3-triazole-4-carboxylic acid (Ryan Scientific Screening Library), 8-methyl-4-oxo-1,4-dihydroquinoline-2-carboxylic acid (Aurora Building Blocks), 2-carbamoylnicotinic acid (J & K Scientific Product List), 8-methylimidazo[1,2-a]pyridine-2-carboxylic acid (Aurora Building Blocks), 3-(1H-pyrazol-3-yl)benzoic acid (Maybridge, Cornwall, UK), 3-(1H-pyrazol-1-yl)benzoic acid (AKos Screening Library), 1H-pyrrolo-[2,3-b]pyridine-3-carboxylic acid (Aldrich), 6-morpholin-4-ylnicotinic acid (Ryan Scientific Product List), 7-methylimidazo[1,2-a]pyridine-2-carboxylic acid (Aurora Building Blocks), imidazo[1,2-a]pyridine-2-carboxylic acid (Aurora Building Blocks), 5-pyridin-3-yl-1H-pyrazole-3-carboxylic acid (AKos Screening Library), 6-methyl-2-(methylamino)nicotinic acid (Aurora Building Blocks), imidazo[1,5-a]pyridine-7-carboxylic acid (Bepharm Product List), 3H-imidazo[4,5-b]pyridine-6-carboxylic acid (Sphinx Scientific Laboratory Product List), 7-hydroxypyrazolo[1,5-a]pyrimidine-6-carboxylic acid (Butt Park Screening Library), indolizine-2-carboxylic acid (Ryan Scientific Product List), 2-pyridin-2-yl-1H-imidazole-5-carboxylic acid (Ambinter Stock Screening Collection), 3-(1H-imidazol-2-yl)benzoic acid (Greenchem Institute Product List), pyrrolo[1,2-c]pyrimidine-3-carboxylic acid (Milestone PharmTech Product List), 1H-pyrrolo[3,2-b]pyridine-2-carboxylic acid (Azasynth Building Blocks), 1H-pyrrolo[3,2-c]pyridine-2-carboxylic acid (Aurora Building Blocks), imidazo[1,2-a]pyridine-7-carboxylic acid (Bepharm Product List), 4-(1H-1,2,4-triazol-1-yl)benzoic acid (AKos Building Blocks Product List), 1-methyl-1H-benzimidazole-5-carboxylic acid (AKos Building Blocks Product List). 6-(1H-pyrazol-1-yl)nicotinic acid (Butt Park Screening Library), 1,6-naphthyridine-2-carboxylic acid (Bepharm Product List), 1H-imidazo[4,5-b]pyridine-5-carboxylic acid (Sphinx Scientific Laboratory Product List), 1-methyl-4-oxo-4,7-dihydro-1H-pyrazolo[3,4-b]pyridine-5-carboxylic acid (Aurora Screening Library), imidazo[1,2-a]pyridine-6-carboxylic acid (Apollo Scientific Intermediates for Research and Development), 1H-pyrrolo-[2,3-c]pyridine-2-carboxylic acid (Parkway Scientific Product List), 1H-indazole-6-carboxylic acid (Aldrich) quinoxaline-2-carboxylic acid (Aldrich), 3-acetamidobenzoic acid (Apollo Scientific Intermediates for Research and Development), 4-chloro-H-indazole-6-carboxylic acid (Sinova Product List). 2-morpholinopyrimidine-5-carboxylic acid (AKos Screening Library), 1H-imidazo[1,2-b]pyrazole-6-carboxylic acid (Aurora Building Blocks), 3-hydroxyquinoline-4-carboxylic acid (AKos Screening Library), 8-hydroxyquinoline-7-carboxylic acid (TCI Laboratory Chemicals) and 3-(1H-pyrazol-4-yl)benzoic acid (AKos Building Blocks Product List).

The following carboxylic acids (which were used to prepare compounds described in the Examples below) were prepared by previously published means: 3-hydroxy-6-s methylpicolinic acid (P. Korovchenko et al., *Catalysis Today* 2007, 121, 13-21); 4-hydroxy-1,3-dimethyl-1H-pyrazole-5-carboxylic acid (*Tet. Let.* 1971, 19, 1591); 3-amino-2,6-dimethylisonicotinic acid (Gulland, J. M., Robinson, R. *J. Chem. Soc., Trans.* 1925, 127. 1493-503); 5-hydroxyquinoline-6-carboxylic acid (Bogert, M. T.; Fisher, Harry L. *Orig. Com. 8th Intern. Cangr. Appl. Chem.* 1912, 6, 37-44; 5-hydroxyisoquinoline-6-carboxylic acid (can be prepared by hydrolysis of the corresponding methyl ester: Dyke, S. F.; White, A. W. C.; Hartley, D. *Tetrahedron* 1973, 29, 857-62); 3-methyl- 1-(pyridin-3-yl)-1H-pyrazole-5-carboxylic acid (can be prepared by analogous chemistry to *J. Het. Chem.* 1999, 36, 217).

The following carboxylic acid starting materials (which were used to prepare compounds described in the Examples below) were prepared as described below.

Acid Preparation 1:
4-chloro-1H-benzimidazole-6-carboxylic acid

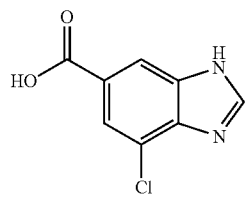 [SMILES: O=C(O)c1cc(Cl)c2nc[nH]c2c1]

To a mixture of 4-amino-3-nitrobenzoic acid (10 g, 56 mmol) in acetic acid (100 mL) at 0° C. was added sulfuryl chloride (8.98 g, 66 mmol). The reaction mixture was allowed to warm to ambient temperature and stirred overnight. The mixture was poured into ice water, filtered and air dried to give 4-amino-5-chloro-3-nitrobenzoic (7.35 g, 62%) as yellow solid. $^1$H NMR (400 MHz, DMSO-d) δ ppm 8.24 (s, 2H) 8.19 (s, 1H) 7.86 (s, 1H)

A suspension of 4-amino-5-chloro-3-nitrobenzoic (7.35 g, 34 mmol) in methanol (150 mL) was treated with concentrated sulphuric acid (40 mL). The suspension was heated to reflux overnight. The reaction solution was concentrated in vacuo to give a yellow solid which was taken up in ethyl acetate (200 mL) and water (30 mL). The solution was cooled to 0° C. and potassium carbonate was added (12.4 g) in water (30 mL). The layers were separated and the aqueous layer was extracted with ethyl acetate (200 mL). The combined organic layers were dried over magnesium sulphate and concentrated in vacuo to give methyl 4-amino-5-chloro-3-nitrobenzoate as a yellow solid (7.25 g, 93%). $^1$H NMR (400 MHz, DMSO-$d_6$) δ ppm 8.50 (d, J=2.15 Hz, 1H) 8.02 (d, J=1.95 Hz, 1H) 7.84 (br. s., 2H) 3.80 (s, 3H).

To a solution of methyl 4-amino-5-chloro-3-nitrobenzoate (4.29 g, 18.6 mmol) in ethanol (115 mL), water (250 mL) and tetrahydrofuran (200 mL) was added sodium hydrosulfite (80 g, 391 mmol). The reaction was stirred at ambient temperature for two hours. To the reaction was added water (55 mL). After stirring for an additional hour saturated aqueous sodium bicarbonate (140 mL) was added to the reaction. The reaction mixture was filtered and the filtrate was extracted twice with ethyl acetate (200 mL each). The organic extracts were combined and washed with saturated aqueous sodium bicarbonate (100 mL) followed by saturated aqueous sodium chloride (100 mL). The organic layer was concentrated in vacuo to a final volume of 100 mL and then allowed to sit at ambient temperature overnight to give a precipitate. The mixture was filtered and dried under a stream of nitrogen to give methyl 3,4-diamino-5-chlorobenzoate (973 mg, 26%). The filtrate was concentrated in vacuo to give methyl 3,4-diamino-5-chlorobenzoate (2.45 g, 66%). $^1$H NMR (400 MHz, DMSO-d) 5 ppm 7.11 (d, J=1.95 Hz, 1H) 7.08 (d, J=1.95 Hz, 1H) 5.44 (s, 2H) 5.08 (s, 2H) 3.70 (s, 3H).

3,4-diamino-5-chlorobenzoate (1.2 g. 6 mmol) was added to water (10 mL) and formic acid (826 mg, 18 mmol) and heated at reflux for 4 hours. The reaction was cooled to ambient temperature and aqueous potassium hydroxide was added (21 mL, 1M). The reaction solution was washed with ethyl acetate (2×25 mL each). The aqueous layer was acidified to pH=5 with aqueous hydrochloric acid (1N) to give a precipitate which was filtered, washed with water and dried under a stream of nitrogen to give the title compound (439 mg, 37%). $^1$H NMR (400 MHz, DMSO-d) δ ppm 8.45 (s, 1H) 8.10 (d, J=1.17 Hz, 1H) 7.77 (d, J=1.37 Hz, 1H).

Acid Preparation 2: 7-chloro-2-oxo-2,3-dihydro-1H-benzo[d]imidazole-5-carboxylic acid

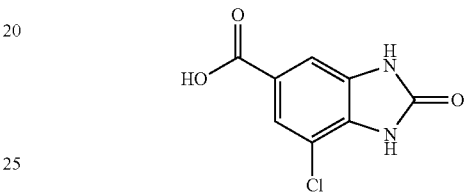

3,4-diamino-5-chlorobenzoate (from acid preparation 1, 100 mg, 0.50 mmol) and carbonyl diimidazole (89 mg, 0.55 mmol) were combined in tetrahydrofuran (2 mL) and stirred for 16 hours. The reaction solution was heated to 60° C. for 3 hours. To the reaction was added carbonyl diimidazole (81 mg, 0.50 mmol) and the reaction was continued at 60° C. for two hours. The reaction was allowed to cool to room temperature and stirred for 16 hours. A precipitate formed. The mixture was filtered. The filtrate was concentrated in vacuo and the residue was slurried in ethyl acetate. The slurry was filtered on the same filter as the original filtration. The collected solids were washed with a portion on ethyl acetate and then dried under a stream of nitrogen to give methyl 7-chloro-2-oxo-2,3-dihydro-1H-benzo[d]imidazole-5-carboxylate as a white solid (93 mg, 82%). $^1$H NMR (400 MHz. DMSO-$d_6$) δ ppm 11.60 (br. s., 1H) 11.16 (s, 1H) 7.55 (d, J=1.37 Hz, 1H) 7.38 (d, J=1.56 Hz, 1H) 3.80 (s, 3H).

Methyl 7-chloro-2oxo-2,3-dihydro-1H-benzo[d]imidazole-5-carboxylate (351 mg, 1.55 mmol), 1 M aqueous lithium hydroxide (0.774 mL, 1.55 mmol) and tetrahydrofuran (5 mL) were combined and heated to 50° C. for 2 hours. To the reaction was added 1 M aqueous lithium hydroxide (0.774 mL, 1.55 mmol) and methanol (10 mL) and the reaction was heated to reflux for 6 hours and then allowed to cool to ambient temperature overnight. The reaction solution was concentrated in vacuo to remove the tetrahydrofuran and methanol. The residual aqueous layer was extracted with ethyl acetate (2 mL). To the aqueous layer was added water (2 mL) ethyl acetate (2 mL) and 3 M aqueous hydrochloric acid. A precipitate formed. The mixture was filtered and the solids were washed with water and ethyl acetate. The solids were dried under a stream of nitrogen to give the title compound (296 mg, 90%). $^1$H NMR (400 MHz, DMSO-d) 5 ppm 11.54 (s, 1H) 11.12 (s, 1H) 7.54 (d, J=1.37 Hz, 1H) 7.38 (d, J=1.37 Hz, 1H).

Acid Preparation 3: 4-fluoro-1H-benzo[d]imidazole-6-carboxylic acid

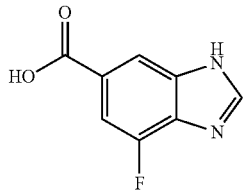 [SMILES: O=C(O)c1cc(F)c2nc[nH]c2c1]

To a 2.5-5 mL microwave tube, was added 6-bromo-4-fluoro-1H-benzo[d]imidazole (160 mg, 0.744 mmol) suspended in de-gassed 1,4 dioxane (1.5 mL). To this was added trans-di(u-acetato)bis[o-(di-o-tolylphino)benzyl]di-palladium (II) (26 mg, 0.043 mmol) and molybdenum hexacarbonyl (100 mg, 0.38 mmol), along with sodium carbonate (237 mg, 2.23 mmol) dissolved in de-gassed water (2 mL). The mixture was stirred for 20 seconds and then heated at 155° C. in the microwave for 10 minutes, keeping the pressure under 16 bar. The vessel was vented before handling and left to stand overnight at room temperature. Water (2 mL) and ethyl acetate (3 mL) were added to the reaction, and then the mixture was filtered through Celite®. The filtrate was partitioned with ethyl acetate and separated. The aqueous fraction was washed with ethyl acetate once more and the combined organic layers were set aside. Another portion of water (5 mL) was added to the aqueous layer and acidified with 0.5 M HCl to pH 3; a brown precipitate was formed. The mixture was allowed to stand in the refrigerator at 4° C. for 1 hour. The mixture was filtered and washed with water to give 4-fluoro-1H-benzo[d]imidazole-6-carboxylic acid as a grey solid, (63% yield). $^1$H NMR (500 MHz, DMSO-d$_6$) □ ppm 1299 (br. s., 1H) 8.47 (s, 1H) 8.02 (s, 1H) 7.52 (d, J=11.71 Hz, 1H).

Acid Preparation 4: 1-oxo-1,2-dihydroisoquinoline-6-carboxylic acid

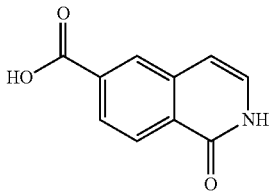 [SMILES: O=C(O)c1ccc2c(=O)[nH]ccc2c1]

To a mixture of (E)-3-(3-bromophenyl)acrylic acid (100 g, 0.44 mol) and triethylamine (0.48 mol) in toluene (1000 mL) was added diphenylphosphoryl azide (127.4 g, 0.45 mol) dropwise at 0-10° C. The mixture was stirred at room temperature overnight. Thin layer chromatography (petroleum ether/ethyl acetate=8:1) indicated completion of reaction. The resulting mixture was washed with 1 N sodium hydroxide (500 mL) and extracted with ethyl acetate (2000 mL×3). The organic layer was concentrated to give crude (E)-1-azido-3-(3-bromophenyl)prop-2-en-1-one, which was used in the next step directly.

A mixture of crude (E)-1-azido-3-(3-bromophenyl)prop-2-en-1-one (crude about 120 g) and toluene (200 mL) was refluxed for two hours. Thin layer chromatography (petroleum ether/ethyl acetate=8:1) indicated most of the starting material was consumed. The mixture was concentrated to give crude (E)-1-bromo-3-(2-isocyanatovinyl)benzene (100 g, 94%), which was used in the next step directly.

A solution of (E)-1-bromo-3-(2-isocyanatovinyl)benzene (100 g, 0.44 mol) in toluene (200 mL) was added dropwise to a mixture of tributylamine (100 mL) and oxydibenzene (500 mL) at 190° C. After the addition, the mixture was heated at 210° C. for another two hours. Thin layer chromatography (petroleum ether/ethyl acetate=1:1) indicated the reaction was complete. The mixture was cooled to room temperature, filtered, and the solid was washed with ethyl acetate (50 mL×3). The solid was dried under vacuum to give crude 6-bromoisoquinolin-1(2H)-one (30 g, 30%) as a light yellow solid, which was used in the next step directly.

A mixture of 6-bromoisoquinolin-1(2H)-one (30 g, 134 mmol), triethylamine (17.6 g, 174 mmol), palladium (II) chloride (0.24 g, 1.34 mmol) and (S)-(-)-2,2'-bis(diphenylphosphino)-1,1'-binaphthyl (0.84 g, 1.34 mmol) in methane (300 mL) was heated at 100° C. under 2 MPa of carbon monoxide and stirred for 12 hours. Thin layer chromatography (petroleum ether/ethyl acetate=1:1) indicated the reaction was complete. The reaction mixture was concentrated, the residue was washed with water, and the solid was filtered and dried in vacuum to give crude methyl 1-oxo-1,2-dihydroisoquinoline-6-carboxylate (23.8 g, 95%) as a yellow solid, which was used in the next step directly.

To a mixture of methyl 1-oxo-1,2-dihydroisoquinoline-6-carboxylate (25 g, 0.133 mol), tetrahydrofuran (200 mL) and water (200 mL) was added lithium hydroxide (16.8 g, 0.40 mol) at room temperature, and the mixture was stirred for four hours. Thin layer chromatography (petroleum ether/ethyl acetate=1:1) indicated the reaction was complete. The reaction mixture was extracted with ethyl acetate (100 mL×3) to remove impurities. The aqueous layer was acidified with 4 N aqueous HCl to pH 5 and filtered. The solid was dried in vacuum to give 1-oxo-1,2-dihydroisoquinine-6-carboxylic acid (11.3 g, 48%) as a light yellow solid. $^1$H NMR (400 MHz, DMSO-d$_6$) δ ppm 11.48 (s, 1H), 8.24 (d, 2H), 7.93 (d, 1H), 7.22 (d, 1H), 6.68 (d, 1H).

Acid Preparation 5: 1-oxo-1,2-dihydroisoquinoline-7-carboxylic acid

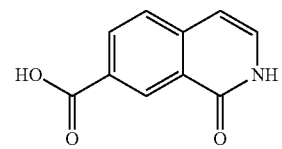 [SMILES: O=C(O)c1ccc2cc[nH]c(=O)c2c1]

1-oxo-1,2-dihydroisoquinoline-7-carboxylic acid was prepared in an analogous fashion to 1-oxo-1,2-dihydroisoquinoline-6-carboxylic acid, (acid preparation 4).

Acid Preparation 6: 5-(1H-imidazol-1-yl)picolinic acid

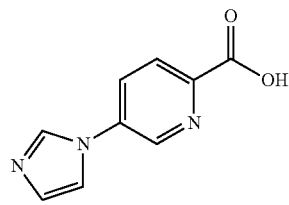 [SMILES: O=C(O)c1ccc(-n2ccnc2)cn1]

5-bromopicolinonitrile (2.0 g, 10.9 mmol), imidazole (818 mg, 12 mmol) potassium carbonate (1.66 g, 12 mmol) and dimethylformamide (40 mL) were combined and heated to 130° C. for 20 hours. The reaction solution was evaporated and the residue was partitioned between dichloromethane (150 mL) and water (100 mL). The phases were separated and the organic phase was washed with water (50 mL), dried over magnesium sulfate and evaporated to give a residue which was purified by flash chromatography eluting with 2-3% methanol in dichloromethane gradient to give 5-(1H-imidazol-1-yl)picolinoritrile (1.23 g, 66%).

5-(1H-imidazol-1-yl)picolinonitrile (136 mg, 0.80 mmol) was heated to reflux in 6N aqueous hydrochloric acid (10 mL) for 2 hours. The reaction mixture was evaporated and the residue was azeotroped with three portions of toluene to give a residue which was purified on an ion exchange column (AG-50 Biorad) eluting with a 0-10% pyridine in water gradient to give the title compound as a white solid (128 mg, 84%). $^1$H NMR (400 MHz, DMSO-$d_6$) δ ppm 9.10 (s, 1H), 8.50 (s, 1H), 8.26-8.33 (m, 1H), 8.13-8.20 (m, 1H), 7.96 (s, 1H), 7.16 (s, 1H).

Acid Preparation 7:
7-chloro-1H-indazole-5-carboxylic acid

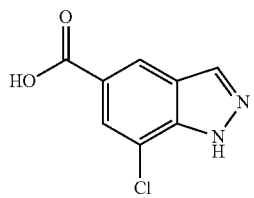 [SMILES: O=C(O)c1cc(Cl)c2[nH]ncc2c1]

To a mixture of 4-amino-5-methyl-benzonitrile (3.0 g, 18.0 mmol) in chloroform (50 mL) was added acetic anhydride (3.92 mL, 41.4 mmol). The mixture was heated at reflux for 5 hours and then cooled to room temperature. To the mixture was added potassium acetate (530 mg, 5.4 mmol) and isoamyl nitrite (5.28 mL, 39.6 mmol). The reaction was heated at reflux for 16 hours. The reaction mixture was coded to room temperature, extracted with saturated aqueous sodium bicarbonate, the organics were dried over sodium sulfate, and concentrated in vacuo to afford a brown oil. The oil was dissolved in methanol (25 mL) and concentrated hydrochloric acid (25 mL) was added. The reaction was stirred at room temperature for 22 hours and the methanol was concentrated in vacuo. The remaining aqueous layer was adjusted to a pH of 7 and the resultant precipitate was filtered to afford a brown solid which was purified by flash chromatography using 50% dichloromethane in heptane as eluent to afford 7-chloro-1H-indazole-5-carbonitrile as a solid (585 mg, 18%): −ESI MS (M−1) 176.0; $^1$H NMR (400 MHz, CDC$_3$) δ ppm 8.29 (br. s., 2H), 8.08 (s, 1H), 7.61 (s, 1H).

To a mixture of 7-chloro-1H-indazole-5-carbonitrile (1.36 g, 7.66 mmol) in ethanol (52.5 mL) was added water (17.5 mL) and potassium hydroxide (6.44 g. 115 mmol). The reaction mixture was heated at reflux for 16 hours. The reaction mixture was cooled to room temperature, extracted twice with ethyl ether, acidified the aqueous with 1N hydrochloric acid and the resultant precipitate was filtered to afford 7-chloro-1H-indazole-5-carboxylic acid as a brown solid (900 mg, 60%): −ESI MS (M−H) 1952.

Acid Preparation 8: 5-morpholinopicolinic acid

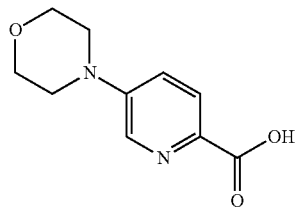 [SMILES: O=C(O)c1ccc(N2CCOCC2)cn1]

Diethyl malonate (151 g, 0.944 mol) was added dropwise under stirring to 60% sodium hydride in mineral oil (37.8 g, 0.944 mol) in dry tetrahydrofuran (1 L). After hydrogen evolution ceased, 2-chloro-5-nitropyridine (125 g, 0.787 mol) was added. The reaction mixture was refluxed for 2 hours and then the tetrahydrofuran was evaporated in vacuo to give crude diethyl (5-nitropyridin-2-yl)malonate, which was used at the next stage without purification.

Crude diethyl (5-nitropyridin-2-yl)malonate was added to boiling 65% nitric acid (1.5 L) under stirring. The reaction mixture was refluxed under stirring for 15 hours. The reaction mixture was concentrated in vacuo and the resulting solid was washed with chloroform to give 5-nitropyridine-2-carboxylic acid (yield 65%, 85.9 g).

5-Nitropyridine-2-carboxylic acid (100 g, 0.60 mol) was heated at reflux in methanol (1 L) and sulfuric acid (57 mL) for 5 hours. The reaction mixture was coded, reduced to half volume in vacuo, and the residue neutralized with a solution of sodium carbonate. The resulting precipitate was filtered to give methyl 5-nitropyridine-2-carboxylate (yield 89%, 98 g).

Methyl 5-nitropyridine-2-carboxylate (182 g, 1 mol) was refluxed in piperidine (250 mL) for 1 hour. The reaction mixture was concentrated in vacuo to give crude 5-nitro-2-(piperidin-1-ylcarbonyl)pyridine, which was used for the next stage without additional purification.

Crude 5-nitro-2-(piperidin-1-ylcarbonyl)pyridine was reduced by hydrogen under atmospheric pressure in the presence of 10% paladium on carbon (4 g) in acetic acid (500 mL). The catalyst was separated by filtration and the solvent evaporated in vacuum to give crude 6-(piperidin-1-ylcarbonyl)pyridin-3-amine, which was used for the next stage without additional purification.

A solution of sodium nitrite (69 g) in concentrated hydrochloric acid (1.5 L) was added to crude 6-(piperidin-1-ylcarbonyl)pyridin-3-amine at 0 C, and the mixture was stirred for 10 minutes. Urea (20 g) was added, and the mixture was stirred for 15 minutes. Sodium iodide (150 g) was added, and the product was separated by filtration and recrystallized from ethanol to give 5-iodo-2-(piperidin-1-ylcarbonyl)pyridine (yield 23% calculated for methyl 5-nitropyridine-2-carboxylate, 71 g).

A mixture of 5-iodo-2-(piperidin-1-ylcarbonyl)pyridine (71 g, 0.23 mol), palladium (II) acetate (1.03 g, 46 mmol), 2-(di-tert-butylphosphino)biphenyl (2.76 g, 92 mmol), morpholine (23.7 g, 0.28 mol), and sodium tert-butoxide (27.8 g, 0.28 mol) in toluene (400 mL) was stirred under argon at 95 C for 2 hours. The product was isolated by chromatography (silica gel, ethyl acetate) and recrystallized from ethanol to give 4-[6-(piperidin-1-ylcarbonyl)pyridin-3-yl]morpholine (yield 37%, 22 g).

25% KOH (100 mL) was added to 4-[6-(piperidin-1-ylcarbonyl)pyridin-3-yl]morphline (18.3 g), and the mixture was refluxed and then neutralized with HCl. The solution was evaporated in vacuum, and the product was extracted with hot isopropanol to give the title compound (yield 71%, 11.5 g). +ESI MS (M+H) 209.7; $^1$H NMR (400 MHz, DMSO-$d_6$) δ ppm 8.34 (br. s., 1H), 8.03 (d, 1H), 7.65 (dd, 1H), 3.75 (br. s., 4H), 3.40 (br. s., 4H).

Acid Preparation 9: 7-chloro-2-methyl-1H-benzo[d]imidazole-5-carboxylic acid

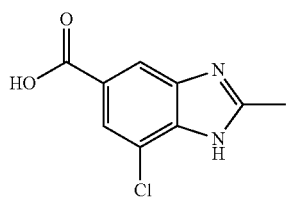

Add 2N hydrochloric acid (8 mL) to a solution of 3,4-diamino-5-chlorobenzoate (from acid preparation 1, 435 mg, 2.17 mmol) in ethanol (20 mL). Heat the mixture to reflux then acid acetylacetone (437 mg, 4.37 mmol) to the yellow solution. The yellow solution turned purple upon addition. Stir at reflux for 1 hour and the solution turned back to yellow. Stir at reflux for an additional 1 hour. Concentrate the solvent to a colorless residue. Add water (20 mL). Extract the suspension with ethyl acetate (20 mL). Basify the aqueous layer with 2N sodium hydroxide (~8 mL) to pH-10. Extract with ethyl acetate (3×15 mL). Wash combined organics from the basic extraction with brine (5 mL). Dry over magnesium sulfate, to filter, concentrate, and dry under high vacuum to yield methyl 7-chloro-2-methyl-1H-benzo[d]imidazole-5-carboxylate (290 mg, 59%) as a colorless solid. $^1$H NMR (400 MHz, CDCl$_3$) δ ppm 2.68 (s, 3H), 3.93 (s, 3H), 7.25 (s, 1H), 7.96 (s, 1H).

Add 2N sodium hydroxide (5 mL, 5 mmol) to a solution of methyl 7-chloro-2-methyl-1H-benzo[d]imidazole-5-carboxylate (280 mg, 1.25 mmol) in methanol (7.5 mL). Stir at 65° C. for 16 hours. The methanol was concentrated in vacuo and the remaining aqueous layer was extracted with ethyl acetate (10 mL). Acidify the aqueous layer to pH~4 with 1N hydrochloric acid (~5 mL). A colorless precipitate was filtered and dried under high vacuum to yield the title compound (189 mg, 72%). $^1$H NMR (400 MHz, CD$_3$OD) δ ppm 2.61 (s, 3H), 7.86 (d. J=1.37 Hz, 1H), 8.08 (d, J=1.17 Hz, 1H).

Acid Preparation 10: 7-chloro-2-methyl-1H-benzo[d]imidazole-5-carboxylic acid

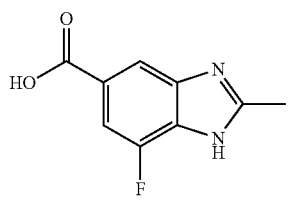

A round bottomed flask was charged with 5-bromo-3-fluorobenzene-1,2-diamine (400 mg. 2 mmol) and 30 mL ethanol. 5 N hydrochloric acid (8 mL, 40 mmol) was then added. This mixture was heated to reflux and 2,4-pentanedione was added. The reaction mixture turned deep purple in color then slowly turned back to tan. Reaction was allowed to proceed for 3 hours and then cooled and neutralized with saturated sodium bicarbonate solution. The reaction mixture was then extracted three times with dichloromethane. The combined organic layers were washed with brine, dried with magnesium sulfate, filtered and concentrated in vacuo. The crude mixture was triturated in diethyl ether then filtered to give 6-bromo-4-fluoro-2-methyl-1H-benzo[d]imidazole (375 mg, 82%) as a tan solid. $^1$H NMR (400 MHz, CDCl$_3$) δ ppm 7.44 (br. s., 1H), 7.10 (d, J=11.22 Hz, 1H), 2.63 (s, 3H).

A 5 mL microwave vial was charged 6-bromo-4-fluoro-2-methyl-1H-benzo[d]imidazole (187 mg, 0.815 mmol) and suspended in de-gassed dioxane (2 mL), trans-di-μ-acetatobis[2-(di-O-tolylphosphino)benzyl]dipalladium (II) (28 mg, 0.048 mmol) and molybdenumhexacarbonyl (110 mg, 0.417 mmol). Degassed 10% aqueous sodium carbonate (2.45 mL, 2.45 mmol) was then added. The reaction was then stirred for 20 seconds before being reacted in the microwave at 155° C. at very high absorption for 10 minutes. The vessel was then vented and left to stand overnight at room temperature. Water (2 mL) and ethyl acetate (3 mL) were then added and the mixture was filtered through Celite®. The layers were separated and the aqueous layer was washed with ethyl acetate (×2). The combined ethyl acetate layers were set aside. Water (5 mL) was added to the aqueous layer which was then acidified with 0.5 M hydrochloric acid to a pH of 3 then cooled to 4° C. A solid formed which was filtered and washed with water to give the title compound (61 mg, 37%) as a yellow solid. A second crop formed which was then filtered to give the title compound (100 mg, 63%). $^1$H NMR (500 MHz, CD$_3$OD) δ ppm 8.22 (d, J=0.98 Hz, 1H), 7.91 (d, J=10.49 Hz, 1H), 2.95 (s, 3H).

Acid Preparation 11: 1H-pyrazolo[4,3-b]pyridine-6-carboxylic acid

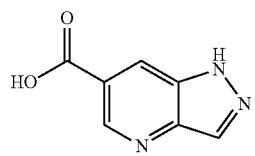 [SMILES: O=C(O)c1cnc2cn[nH]c2c1]

To a suspension of sodium hydride (5.08 g, 127 mmol) in dimethylformamide (75 mL) was added diethyl malonate (1926 mL, 127 mmol) at 0° C. The solution was then stirred at ambient temperature for 30 minutes and a solution of 5-bromo-2-chloro-3-nitropyridine (30 g, 127 mmol) in dimethylformamide (75 mL) was added dropwise. The dark brown mixture was then stirred at 100° C. for 2 hours before being cooled to ambient temperature and quenched with a saturated solution of ammonium chloride (500 mL) at 0° C. The mixture was extracted with ethyl acetate (3×500 mL) and the combined organics were dried over magnesium sulfate. The solvent was removed in vacuo to give a dark brown oil which was purified by flash column chromatography (10% ethyl acetate/hexane) to afford diethyl 2-(5-bromo-3-nitropyridin-2-yl)malonate as a brown solid (31.8 g, 88 mmol, 69%). $^1$HNMR (400 MHz, CDCl$_3$): δ ppm 8.86 (s, 1H), 8.61 (s, 1H), 5.44 (1H, s), 4.29 (q, 4H), 127 (t, 6H).

A mixture of the diethyl 2-(5-bromo-3-nitropyridin-2-yl)malonate (31.8 g, 88 mmol) in aqueous hydrochloric acid (6M, 1.4 L) was stirred at reflux for 18 hours. The reaction mixture was cooled to ambient temperature and added very slowly to a saturated aqueous solution of aqueous sodium bicarbonate (4 L) at 0° C. The mixture was then extracted with dichloromethane (7 L), dried over magnesium sulfate and the solvent removed in vacuo to give 5-bromo-2-methyl-3-nitropyridine as an orange oil (13.8 g, 63.9 mmol, 72%) which solidified upon standing. $^1$HNMR (300 MHz, CDCl$_3$): δ ppm 8.78 (s, 1H). 8.43 (s, 1H), 2.79 (s, 3H).

To a solution of 5-bromo-2-methyl-3-nitropyridine (13.8 g, 63.9 mmol) in industrial methylated spirit (330 mL) at 40° C. was added iron powder (20 g) (portionwise to avoid dumping) followed by concentrated aqueous hydrochloric acid (5 mL). The dark brown mixture was stirred vigorously at reflux for 2 hours and then cooled and filtered through Celite® (which was washed with 1 L of industrial methylated spirit). The solvent was then removed in vacuo and the residue taken up in ethyl acetate (200 mL) and washed with a saturated aqueous solution of sodium bicarbonate (200 mL), dried over magnesium sulfate and solvent removed in vacuo to give 5-bromo-2-methylpyridin-3-amine as an orange solid, (10.7 g, 57.5 mmol, 89.9%). $^1$HNMR (400 MHz, CDCl$_3$): δ ppm 7.91 (s, 1H), 7.00 (s, 1H), 3.75 (br.s, 2H), 2.25 (s, 3H).

To a solution of 5-bromo-2-methylpyridin-3-amine (10.7 g, 57.5 mmol) in dichloromethane (575 mL) was added acetic anhydride (12 mL, 126.5 mmol) at 0° C. followed by triethylamine (22 mL, 158 mmol). The mixture was allowed to warm to ambient temperature and stirred for 18 hours at which point a further equivalent of acetic anhydride (6 mL, 63 mmol) was added. The mixture was stirred at ambient temperature for a further 72 hours. The reaction mixture was quenched with a saturated aqueous solution of sodium bicarbonate (500 mL) and the organic phase washed with saturated aqueous sodium chloride (500 mL), dried over magnesium sulfate and concentrated in vacuo to give a brown solid. This solid was triturated with 30% ethyl acetate in hexanes to yield N-(5-bromo-2-methylpyridin-3-yl)acetamide as an off-white solid. (8.28 g, 36 mmol, 63%). $^1$HNMR (400 MHz, CD$_3$OD): δ ppm 8.31 (s, 1H), 8.18 (s, 1H), 2.43 (s, 3H), 2.18 (s, 3H).

To a solution of N-(5-bromo-2-methylpyridin-3-yl)acetamide (8.28 g, 36 mmol) in chloroform (550 mL) at ambient temperature was added potassium acetate (4.32 g, 43.6 mmol), acetic acid (2.5 mL, 43.6 mmol) and followed by acetic anhydride (6.86 mL, 72.6 mmol). The mixture was stirred at ambient temperature for 15 minutes before being heated to 40° C. Isoamylnitrite was then added dropwise. The reaction was then stirred at 60° C. for 48 hours. The reaction mixture was poured slowly into a saturated solution of sodium bicarbonate (500 mL) at 0° C. The organic phase was retained and the aqueous phase extracted with dichloromethane (500 mL). The combined organics were then concentrated to a brown oil which was dissolved in methanol (500 mL). Aqueous sodium hydroxide (2 M, 500 mL) was added at 0° C. and the mixture stirred at ambient temperature for 1 hour before the methanol was removed in vacuo. The aqueous mixture was then extracted with ethyl acetate (3×500 mL). The combined organics dried over magnesium sulfate, and the solvent removed in vacuo to give 6-bromo-1H-pyrazolo[4,3-b]pyridine as a light brown solid (5.5 g, 27.9 mmol, 77%). $^1$HNMR (400, CD$_3$OD): δ ppm 8.55 (s, 1H), 8.24 (s, 1H), 8.21 (s, 1H).

To a solution of 6-bromo-1H-pyrazolo[4,3-b]pyridine (5.5 g, 27.9 mmol) in methanol (125 mL) and acetonitrile (75 mL) was added triethylamine (22 mL, 156 mmol), 2,2'-bis(diphenylphosphino)-1,1'-binaphthyl (1.98 g, 3.07 mmol), palladium dichloride (1.23 g, 6.98 mmol). The mixture was placed under 20 bar of carbon monoxide, heated to 100° C., and stirred vigorously for 18 hours. The reaction mixture was cooled to ambient temperature and filtered through Celite® before the solvent was removed in vacuo to yield a brown oil. This crude oil was then purified by flash column chromatography (1:1, ethyl acetate:hexane) to give methyl 1H-pyrazolo[4,3-]pyridine-6-carboxylate as a pale yellow solid (4.52 g, 92% yield). $^1$HNMR (400, CDCl$_3$) δ ppm 10.56 (s, 1H), 9.23 (s, 1H), 8.35 (s, 1H), 8.40 (s, 1H), 4.01 (s, 3H).

To a solution of methyl 1H-pyrazolo[4,3-b]pyridine-6-carboxylate (3.52 g, 20 mmol) in methanol (250 mL) and water (190 mL) at 0° C. was added aqueous sodium hydroxide (2M, 64 mL, 128 mmol), dropwise. The suspension was then allowed to warm to ambient temperature and stirred for 18 hours. The methanol was then removed in vacuo and the aqueous mixture extracted with ethyl acetate (250 mL) before being acidified (to pH 5-6) with aqueous hydrochloric acid (2 M, 70 mL). The cream solid which had precipitated out was then filtered off and dried in a desiccator to yield the title compound (0.675 g, 4.16 mmol, 21% yield). $^1$HNMR (400 MHz, DMSO-d$_6$): δ ppm 8.97 (s, 1H), 8.45 (s, 1H), 8.39 (s, 1H).

Acid Preparation 12:
3-cyano-1H-indazole-5-carboxylic acid

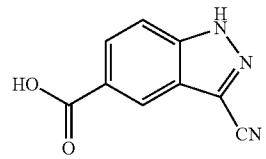 [SMILES: N#Cc1n[nH]c2ccc(C(=O)O)cc12]

A suspension of (2-nitrophenyl)-acetonitrile (30 g, 185 mmol) and 10% palladium on carbon (2 g) in acetic acid (450 mL) was hydrogenated in a Parr apparatus under 30 psi pressure at ambient temperature for 2 hours. The mixture was filtered through a Celite® pad and the filtrate was concentrated in vacuo. The obtained residue was dissolved in ethyl acetate (250 mL). The resulting solution was washed with water (2×100 mL) and saturated sodium chloride (50 mL), and then dried over anhydrous sodium sulfate and concentrated in vacuo to yield product. The crude material was purified by column chromatography (100-200 mesh silica gel) using 8% ethyl acetate in petroleum ether as eluent to afford (2-aminophenyl)acetonitrile (13.5 g, 55%) as a solid. $^1$HNMR (CDCl$_3$) δ ppm 7.3-7.1 (m, 2H), 6.9-6.7 (m, 2H), 3.7 (br, 2H), 3.5 (s, 2H).

To a cooled solution of (2-aminophenyl)acetonitrile (13 g, 98 mmol) in dimethylformamide (150 mL) at 0° C., was added N-bromosuccinimide (19.3 g, 108 mmol) in portions for 30 minutes and maintained at 0° C. for 1 hour. The mixture was diluted with ethyl acetate (300 mL) and washed with water (3×100 mL) and saturated sodium chloride (50 mL). The organic layer was dried over anhydrous sodium sulfate and concentrated in vacuo. The obtained crude product was purified by column chromatography (100-200 mesh silica gel) using 10% ethyl acetate in petroleum ether as eluent to afford (2-amino-5-bromophenyl)acetonitrile (11 g, 53%) as solid. $^1$HNMR (CDCl$_3$) δ 7.35 (s, 1H), 7.25 (d, 1H), 6.65 (d, 1H). 3.7 (br, 2H), 3.52 (s, 2H).

To a cooled solution of (2-amino-5-bromophenyl)acetonitrile (11 g, 52 mmol) in concentrated hydrochloric acid (110 mL) at −50° C., a solution of sodium nitrite (3.9 g, 57 mmol) in water (20 mL) was added slowly. After the addition, the mixture was stirred at −50° C. for 2 h. The mixture was neutralized with 33% ammonium hydroxide at 0° C. and extracted with ethyl acetate (3×100 mL). The combined organic layers were washed with saturated sodium chloride (100 mL), dried over anhydrous sodium sulfate and concentrated. The obtained crude product was purified by column chromatography (100-200 mesh silica gel) using 10% ethyl acetate in petroleum ether as eluent to afford 5-bromo-3-cyanoindazole (7 g, 60%) as a solid. $^1$HNMR (CDCl$_3$) δ ppm 10.7 (br, 1H), 8.1 (s, 1H), 7.64 (d. 1H), 7.5 (d, 1H).

A suspension of 5-bromo-3-cyanoindazole (3 g, 13.51 mmol), palladium dichloride 1,1'-bis(diphenylphosphino) ferrocene (1.76 g, 2.16 mmol), sodium acetate (3.32 g, 40.5 mmol), dimethylformamide (1 mL) in methanol (100 mL) was degassed, and kept under carbon monoxide (80 psi) pressure at 80° C. in a autoclave for 16 hours. The mixture was diluted with water (50 mL), filtered through Celite® bed and the filtrate was concentrated. The obtained residue was acidified with 10% citric acid solution and extracted with ethyl acetate (2×100 mL). The combined organic layers were washed with brine (50 mL), dried over anhydrous sodium sulfate and concentrated. The obtained crude product was purified by column chromatography (100-200 mesh silica gel) using 10% ethyl acetate in chloroform as eluent to afford methyl 3-cyano-1H-indazole-5-carboxylate (1.8 g, 68%) as a solid. $^1$HNMR (CDCl$_3$) δ ppm 10.8 (s, 1H), 8.7 (s, 1H), 8.22 (d, 1H), 7.64 (d, 1H), 4.0 (s, 3H).

To a solution of methyl 3-cyano-1H-indazole-5-carboxylate (2.5 g, 12 mmol) in ethanol (40 mL), a solution of lithium hydroxide (1.04 g. 24.9 mmol) in water (15 mL) was added and stirred at ambient temperature for 16 h. The mixture was concentrated and the obtained residue was dissolved in water (25 mL) and washed with ethyl acetate (20 mL). The aqueous layer was acidified with 10% citric acid solution, the obtained precipitate was filtered, washed with 50% ethyl acetate in petroleum ether (2×10 mL) and dried to afford the title compound (1.9 g, 82%) as a brown solid. $^1$HNMR (DMSO-d) δ ppm 13.8-12.4 (br, 2H), 8.44 (s, 1H), 8.1 (d, 1H), 7.82 (d, 1H).

Acid Preparation 13: 2-(1H-pyrazol-3-yl)isonicotinic acid

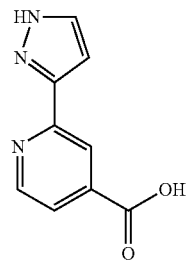 [SMILES: O=C(O)c1ccnc(-c2cc[nH]n2)c1]

To a stirred solution of 29.0 g (69 mmol) 2-bromo-4-methylpyridine in 150 mL concentrated sulfuric acid was added portionwise 67.9 g (231 mmol) potassium dichromate. The reaction mixture was cooled with an ice bath so that the temperature stayed between 20-50° C. After the addition was complete, stirring was continued at room temperature for a further 2 hours. The reaction mixture was then poured slowly onto 2 L ice-water and the mixture stirred for 1 hour at room temperature. The resulting crystals ware collected by filtration, washed with water until the washings were colorless, and dried in vacuo to afford 30.0 g (88%) of 2-bromoisonicotinic acid.

To an ice cooled solution of 2-bromoisonicotinic acid (73 g, 0.361 mol) in dichloromethane (500 mL) and methanol (35 g, 1.08 mol) was added 1-ethyl-3-[3-(dimethylamino)propyl] carbodiimide hydrochloride (67 g, 0.434 mol) by portions. The mixture was stirred at ambient temperature overnight. Then 120 g silica gel was added and the solvent evaporated. The residue was purified by flash chromatography, eluting with 5% ethyl acetate in petroleum ether to afford 58 g (75%) of methyl 2-bromoisonicotinate as a white solid.

Methyl 2-bromoisonicotinate (216 g, 1 mol), dry acetonitrile (1.7 L), ethynyl(trimethyl)silane (117 g, 1.2 mol), diisopropylamine (122 g, 1.2 mol), and dichlorobis(triphenylphosphine)palladium (36 g, 0.05 mol) were placed into a well dried three necked flask which was twice purged with a stream of nitrogen. The reaction mixture was stirred for 0.5 hours, coded to 10° C., and copper iodide (19 g, 0.1 mol) was added under a stream of nitrogen. At 20° C., the reaction mixture became thick and black and an exotherm was observed which was followed by formation of a precipitate. After the addition of copper iodide, the reaction mixture was stirred for further 2 hours at ambient temperature. The precipitated residue was separated by filtration and twice washed with diethyl ether (800 mL). The filtrate was washed with saturated ammonium chloride (2×300 mL) and brine (2×300 mL). After drying over sodium sulfate, the solvent was evaporated. The residue was purified using a silica gel column, eluting with hexane followed by 5% ethyl acetate in petroleum ether to yield 191 g (82%) of methyl 2-((trimethylsilyl) ethynyl)isonicotinate.

Concentrated sulfuric acid (60 mL, 1.1 mol) was added to a suspension of methyl 2-((trimethylsilyl)ethynyl)isonicotinate (127 g, 0.54 mol) in tetrahydrofuran (600 mL) and mercury acetate (51.5 g, 0.16 mol). The suspension was stirred for 3 hours at 50° C. and kept overnight. The reaction mixture was diluted with diethyl ether (1.5 L) and the sulfuric acid was neutralized with saturated sodium bicarbonate (150 g, 1.7 mol). A residue of mercury salts was separated by filtration. The ether solution was washed with water and dried over sodium sulfate. The solvent was removed to give methyl 2-acetylisonicotinate as an oil that was directly used in the next step.

To a 2 L three necked flask was added methyl 2-acetylisonicotinate (160 g, 0.894 mol), dimethylformamide-dimethylacetamide (350 mL) and toluene (350 mL). The mixture was refluxed for about 5 hours with a Dean-Stark trap to remove methanol produced. Additional dimethylformamide-dimethylacetamide and toluene was added to keep the reaction volume at about 800-900 mL. When liquid chromatography-mass spectrometry showed reaction completed, the solvent was removed to yield crude (Z)-methyl 2-(3-(dimethylamino)acryloyl)isonicotinate as a dark solid. The crude solid was directly used in the next step.

To a 2 L three-necked flask was added (Z)-methyl 2-(3-(dimethylamino)acyloyl) isonicotinate (0.894 mol), hydrazine hydrate (48.8 g), anhydrous ethanol (1 L). The suspension was stirred at 20° C. overnight. The solvent was removed in vacuo. The residue was taken up in concentrated hydrochloric acid (600 mL) and heated to reflux for 2 hours. The mixture was cooled to ambient temperature. The resultant precipitate was filtered, washed with water, ethanol and acetone and dried to give 78.6 g of the title compound as a brown solid. $^1$HNMR (DMSO-d$_6$/D$_2$O) δ ppm 8.80 (d, 1H), 8.50 (s, 1H), 7.91 (d, 1H), 7.87 (dd, 1H), 7.15 (d, 1H).

Acid Preparation 14: 3-methyl-2-oxo-2,3-dihydro-1H-benzo[d]imidazole-5-carboxylic acid

Add an aqueous solution of sodium hydrosulfite (17.4 g, 100 mmol in 80 mL of water) to methyl-3-(methylamino)-4-nitrobenzene carboxylate (855 mg, 4.75 mmol) in tetrahydrofuran (70 mL) and ethanol (30 mL) at 0° C. The orange solution turned to an orange suspension upon addition. Stir the mixture at room temperature for 2 hours. The orange suspension turned to a yellow suspension over this time. Add saturated sodium bicarbonate (100 mL) then the yellow suspension turned colorless. Extract the mixture with ethyl acetate (2×100 mL). Wash the combined organics with brine (30 mL). Dry over magnesium sulfate, filter, concentrate, and dry under high vacuum to yield methyl 4-amino-3-(methylamino)benzoate (586 mg, 68%) as a yellow oil. The resulting oil began to crystallize upon standing after 10 minutes. $^1$H NMR (400 MHz, CDCl$_3$) δ ppm 2.89 (s, 3H), 3.37-3.81 (m, 2H), 3.85 (s, 3H), 6.67 (d, J=8.01 Hz, 1H), 7.33 (d, J=1.37 Hz, 1H). 7.44 (dd, J=8.11, 1.66 Hz, 1H).

Add carbonyl diimidazole (567 mg, 3.50 mmol) to a solution of methyl 4-amino-3-(methylamino)benzoate (586 mg. 3.19 mmol) in tetrahydrofuran (20 mL) at room temperature. Stir the yellow solution at room temperature for 16 hours. Add carbonyl diimidazole (500 mg, 0.96). Stir at room temperature for 4 hours. Add ethyl acetate (75 mL). Wash with 10% citric acid (5 mL), 1N sodium hydroxide (5 mL), and brine (5 mL). Dry the organics over magnesium sulfate, filter, concentrate, and dry under high vacuum to yield a crude yellow solid (690 mg, 100%). Triturate this crude solid with ethyl acetate (10 mL). Filter the precipitate and dry under high vacuum to yield methyl 3-methyl-2-oxo-2,3-dihydro-1H-benzo[d]imidazole-5-carboxylate (422 mg, 64%). $^1$H NMR (400 MHz, CDCl$_3$) δ ppm 3.46 (s, 3H), 3.92 (s, 3H), 7.12 (d, J=8.21 Hz, 1H), 7.68 (s, 1H), 7.84 (dd, J=8.31, 1.47 Hz, 1H), 9.87-10.03 (m, 1H).

Add 1N sodium hydroxide (6.1 mL, 6.1 mmol) to a suspension of methyl 3-methyl-2-oxo-2,3-dihydro-1H-benzo[d]imidazole-5-carboxylate (420 mg, 2.04 mmol) in methanol (10 mL). The suspension turned to a solution upon addition of 1N sodium hydroxide. Stir at 65° C. for 16 hours. Cool to room temperature then concentrate to remove the methanol. Extract the aqueous with ethyl acetate (5 mL). Acidify the aqueous with 2N hydrogen chloride (3 mL) to pH~2. Concentrate the aqueous layer to a solid. Triturate the solid with water (3 mL). Filter the precipitate and dry under high vacuum to yield the title compound (234 mg, 59%) as a pale brown solid. $^1$H NMR (400 MHz, DMSO-d$_6$) δ ppm 3.28 (s, 3H). 7.01 (d, J=8.21 Hz, 1H), 7.57 (s, 1H), 7.63 (dd, J=8.11, 127 Hz, 1H), 11.19 (s, 1H), 12.60 (s, 1H).

Acid Preparation 15: 7-bromo-2-oxo-2,3-dihydro-1H-benzo[d]imidazole-5-carboxylic acid

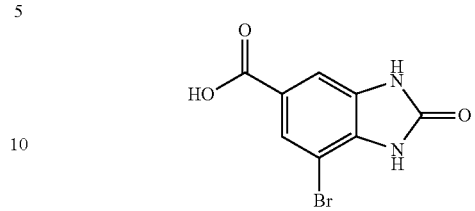

A suspension of methyl 4-amino-3-bromo-5-nitrobenzoate (10 g, 36.3 mmol) and tin(II) chloride (33 g, 14.5 mmol) in methanol (100 mL) was heated to 60° C. and maintained for 4 hours. The reaction mass was cooled to ambient temperature and concentrated to obtain a residue; the residue was basified using saturated aqueous sodium bicarbonate until pH was 11 and the aqueous layer was extracted with dichloromethane (3×200 mL). The combined organic layers were washed with aqueous saturated sodium chloride (200 mL), dried over anhydrous sodium sulfate and concentrated to obtain methyl 3,4-diamino-5-bromobenzoate as an off-white solid (5 g, 58%). $^1$HNMR (CDCl$_3$): δ ppm 7.74 (s, 1H), 7.35 (s, 1H), 4.18 (broad s, 2H), 3.85 (s, 3H) and 3.38-3.56 (broad s, 2H).

A solution of 3,4-diamino-5-bromobenzoate (1 g, 4.0 mmol) and triethylamine (0.4 g, 4.0 nm mL) in dichloromethane (6 mL) was cooled to 0° C. A solution of triphosgene (1.2 g, 4.08 mmol) in dichloromethane (15 mL) was added to this solution. The reaction mixture was allowed to warm to ambient temperature and maintained for 18 hours. The reaction mass was quenched with water (3 mL) and extracted with ethyl acetate (3×10 mL). The combined organic layers were washed with aqueous saturated sodium chloride (50 mL), dried over anhydrous sodium sulfate and concentrated to obtain methyl 7-bromo-2-oxo-2,3-dihydro-1H-benzo[d]imidazole-5-carboxylate as an off-white solid (500 mg, 45%). $^1$HNMR (CDCl$_3$+DMSO-d$_6$): δ 11.35 (s, 1H), 11.05 (s, 1H), 7.75 (s, 1H), 7.52 (s, 1H) and 3.85 (s, 3H).

Methyl 7-bromo-2-oxo-2,3-dihydro-1H-benzo[d]imidazole-5-carboxylate (238 mg, 0.878 mmol) and 2 N aqueous sodium hydroxide (1.50 mL, 3.0 mmol) were combined in methanol (5 mL) and heated to 50° C. for 90 minutes. The reaction solution was concentrated to remove the methanol. To the reaction residue was added ethyl acetate (5 mL). The resultant solution was acidified with 1N aqueous hydrochloric acid (1.5 mL) to give a final pH of 4. A precipitate formed which was filtered and dried under vacuum to give the title compound (226 mg, 100%) as a solid. $^1$H NMR (400 MHz, CD$_3$OD) 3 ppm 7.89 (d, J=1.37 Hz, 1H) 7.65 (d, J=−1.37 Hz, 1H).

Acid Preparation 16: 2-(3-methyl-1,2,4-oxadiazol-5-yl)isonicotinic acid

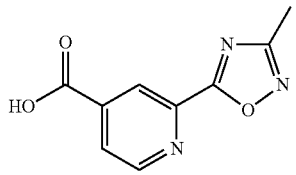

A mixture of acetonitrile (2 mol), hydroxyamine hydrochloride (2 mol) and sodium methoxide (2 mol) was stirred at room temperature for 3 days, then filtered and the filtrate concentrated below 20° C. to give (Z)—N'-hydroxyacetimidamide (150 g) as a white solid which was directly used in the next step.

A mixture of methanol (800 mL), potassium hydroxide (44 g, 0.95 mol) and dimethyl pyridine-2,4-dicarboxylate (ChemPacific) (156 g, 0.79 mol) was refluxed for 0.5 hours and then evaporated in vacuo to afford 4-(methoxycarbonyl)picolinic acid (144 g) as a yellow solid.

To 4-(methoxycarbonyl)picolinic acid (150 g, 1.62 mol) in dichloromethane (500 mL) was added oxalyl chloride (400 mL) keeping the temperature at 25-30° C. for 3 days. The reaction was evaporated in vacuo to afford methyl 2-(chlorocarbonyl)isonicotinate as yellow oil.

To a solution of methyl 2-(chlorocarbonyl)isonicotinate in dichloromethane (500 mL) was added (Z)—N'-hydroxyacetimidamide and triethylamine, keeping the temperature at 25-30° C. for 1 day. The reaction was concentrated in vacuo to afford (Z)-methyl 2-((1-aminoethylideneaminooxy)carbonyl)isonicotinate as a yellow solid.

A solution of (Z)-methyl 2-((1-aminoethylideneaminooxy)carbonyl)isonicotinate in toluene (1 L) was heated at reflux overnight. The obtained mixture was evaporated and purified by silica-gel column chromatography to afford methyl 2-(3-methyl-1,2,4-oxadiazol-5-yl)isonicotinate as a white solid.

A mixture of lithium hydroxide (15 g, 0.35 mol), ethanol (500 mL) and methyl 2-(3-methyl-1,2,4-oxadiazol-5-yl)isonicotinate (52 g, 0.23 mol) were stirred at room temperature for 5 hours, then mixture was concentrated in vacuo. Water was added then extracted with ethyl acetate. The water layer was brought to pH 1.5 with aqueous 1N hydrochloric acid and extracted with ethyl acetate. The organic layer was concentrated in vacuo to afford the title compound as a white solid (42 g). $^1$H NMR (300 MHz, DMSO-$d_6$) δ ppm 14.08 (br s, 1H) 9.00-8.98 (m, 1H) 8.50 (s, 1H) 8.09-8.07 (m, 1H), 2.46 (s, 3H).

Preparation I-1A-1a: tert-butyl
9-oxo-3-azaspiro[5.5]undec-7-ene-3-carboxylate

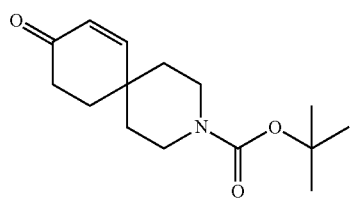

Methyl vinyl ketone (146 mL) was added to a solution of tert-butyl 4-formylpiperidine-1-carboxylate (375 g) in tetrahydrofuran (18 L). The reaction mixture was cooled to −5° C. and a solution of potassium hydroxide in ethanol (3N, 0.243 L) was added dropwise over 10 minutes. The reaction mixture was allowed to warm to room temperature and stirred for 16 hours. Cyclohexane (10 L) was added and the solution was washed with saturated sodium chloride (3×10 L). The organic layer was concentrated to an oil. This oil was dissolved in 2 L of 80:20 cyclohexane I ethyl acetate and filtered through Celite® to remove insoluble material. The filtrate was purified via flash column chromatography (70:30 hexane I ethyl acetate) to afford the product as an oil. The oil was triturated in hexanes to afford the desired product as a white solid (131 g, 28%).

Preparation I-1A-1b: (E)-tert-butyl 10-((dimethylamino)methylene)-9-oxo-3-azaspiro[5.5]undec-7-ene-3-carboxylate

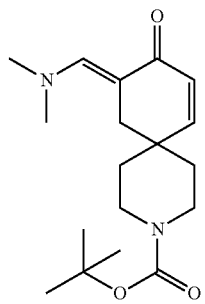

Preparation I-1A-1a (101 g), and tris(dimethylaminomethane) (133 mL) were dissolved in toluene (800 mL) and heated to reflux for 17 hours. The reaction mixture was concentrated to a minimum stirring volume and ethyl acetate (600 mL) was added. This mixture was heated to reflux and heptane (1.2 L) was added over 20 minutes. The hot solution was cooled to room temperature over 3 hours. The solids were filtered through a coarse glass frit and washed with heptane (300 mL). The resulting solid was dried in a vacuum oven at 40° C. for 3 hours to afford the desired product as a yellow solid (107 g). $^1$H NMR (400 MHz, CDCl$_3$) δ ppm 7.48 (s, 1H), 6.57 (d, J=9.97 Hz, 1H), 5.99 (d, J=10.16 Hz, I H), 3.32-3.51 (m, 4H), 3.06 (s, 6H), 2.72 (s, 2H), 1.57-1.66 (m, 2H), 1.41-1.53 (m, 11H).

Preparation I-1A-1c: tert-butyl 1-isopropyl-1,4-dihydrospiro[indazole-5,4'-piperidine]-1'-carboxylate

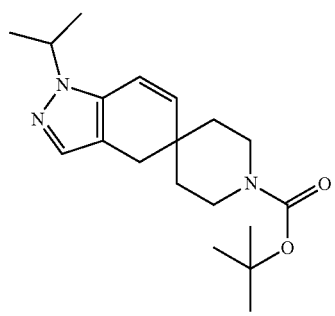

Preparation I-1A-1b (107 g) was taken up in toluene (700 mL) and isopropyl hydrazine (44.4 g) was added. The reaction was stirred at reflux for 4 hours. The reaction was cooled to room temperature and ethyl acetate was added (500 mL). The reaction solution was washed with citric acid (2×300 mL, 10% aqueous), and water (400 mL). The organic layer concentrated in vacuo to afford I-1A-1c as a yellow solid (109 g). $^1$H NMR (400 MHz, CDC$_{31}$) δ ppm 725 (s, 1H) 6.42 (dd, J=10.05, 0.49 Hz, 1H) 5.84 (d, J=9.95 Hz, 1H) 4.42-4.52 (m, 1H) 3.36-3.53 (m, 4H) 2.62 (s, 2H) 1.56-1.68 (m, 2H) 1.45-1.55 (m, 17H).

Preparation I-1A-1d: tert-butyl 1-isopropyl-7-oxo-1,4,6,7-tetrahydrospiro[indazole-5,4'-piperidine]-1'-carboxylate

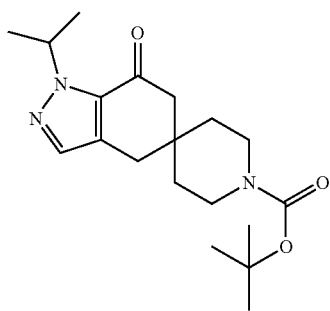

I-1A-1d

To a solution of Preparation I-1A-1c (109 g) in methanol (1 L) was added N-bromo succinimide (61.4 g). The reaction was stirred for 1 hour. The reaction was quenched with sodium thiosulfate (10 g in 300 mL water) and then distilled to a final volume of 500 mL. The solution was cooled to ambient temperature and 2-methyl tetrahydrofuran (1 L) and water (100 mL) were added. The organic layer was removed and the aqueous layer was extracted with 2-methyl tetrahydrofuran. The organic layers were combined, washed with aqueous sodium hydroxide (1 N, 250 mL), water, and saturated aqueous sodium chloride. The organic layer was dried over sodium sulfate, filtered and concentrated to an orange oil. The oil was dissolved in tetrahydrofuran (500 mL) and potassium tert-butoxide (76.8 g) in tetrahydrofuran (500 mL) was added. The solution was heated to 60° C. and stirred for 1 hour. Aqueous hydrochloric acid (1 N, 1 L) was added and the solution was stirred for 30 minutes. The phases ware separated and the aqueous layer was extracted with ethyl acetate (700 mL). The organic layers were combined, washed with water (400 mL) and saturated aqueous sodium chloride (100 mL). The organic layer was dried over sodium sulfate, filtered and concentrated in vacuo to give a residue. The residue was dried in a vacuum oven at 40° C. for 16 hours to afford the title compound as an orange wax (117 g). $^1$H NMR (400 MHz, CDCl$_3$) δ ppm 7.35 (s, 1H), 5.32-5.42 (m, 1H), 3.29-3.51 (m, 4H), 2.73 (s, 2H), 2.51 (s, 2H), 1.47-1.57 (m, 4H), 1.42-1.46 (m, 15H); +ESI MS (M+H)=348.5.

Preparation I-1A-1e: 1-isopropyl-4,6-dihydrospiro[indazole-5,4'-piperidin]-7(1H)-one

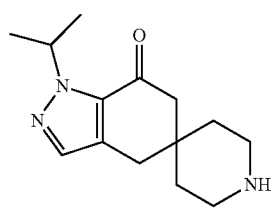

I-1A-1e

Preparation I-1A-1d (23.5 g) was suspended in ethyl acetate (260 mL) and methanol (70 mL). The reaction solution was cooled to <2° C. and acetyl chloride (33.6 mL) was added dropwise over 20 min. The reaction was allowed to slowly warm to room temperature and was stirred for 4 hours. The reaction solution was cooled to 0° C. and the precipitate was filtered. The precipitate was washed with ethyl acetate (200 mL) and dried in a vacuum oven (40° C., 10 mm Hg) for 16 hours to afford the title compound as a light yellow solid. $^1$H NMR (400 MHz, CD$_3$OD) δ ppm 7.43 (s, 1H), 5.32-5.42 (m, 1H), 3.15-3.25 (m, 4H), 2.89 (s, 2H), 2.64 (s, 2H), 1.69-1.90 (m, 4H). 1.37-1.45 (m, 6H); +ESI MS (M+H)=248.4.

Alternate preparation of 1-isopropyl-4,6-dihydrospiro[indazole-5,4'-piperidin]-7(1H)-one Preparation (I-1A-1e)

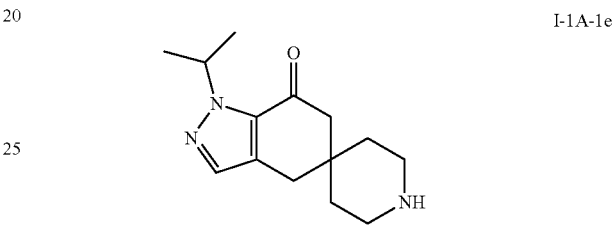

I-1A-1e tert-Butyl 9-oxo-3-azaspiro[5.5]undec-7-ene-3-carboxylate (250 g), and tris(dimethylaminomethane) (325 mL) were dissolved in toluene (1.9 L) and heated at reflux for 4 hours. The mixture was distilled and concentrated to a minimum stirring volume (110° C.) and then toluene (1.9 L) was added. The reaction was redistilled to a minimum stirring volume and cooled to room temperature. Toluene (1.8 L) and isopropyl hydrazine hydrochloride (135 g) were added and the solution was heated to reflux for 5 hours. The reaction was cooled to room temperature and was then washed with citric acid (10% aqueous, 2×150 mL) and water (200 mL), and then the organic layer was distilled to a minimum stirring volume. Methanol (2 L) was added and distilled to a minimum stirring volume. This was repeated with methanol (2 L). The solution was redissolved in methanol (2.5 L) and N-bromosuccinimide (176 g) was added in one portion. The solution was stirred at 23° C. for 2 hours. Aqueous sodium thiosulfate solution (5 wt %, 0.5 L) was added and the mixture was stirred for 15 minutes. The reaction mixture was concentrated via distillation (45° C., 210 mm Hg) to −0.5 L and then 2-methyl tetrahydrofuran (2.5 L) was added. After stirring for 15 minutes the aqueous layer was discarded. The organic layer was concentrated to −0.2 L and tetrahydrofuran (0.5 L) was added. To the mixture was added a potassium tert-butoxide solution in tetrahydrofuran (1.9 L, 1 M solution). The solution was heated to 60° C. and stirred for 1 hour. After cooling to room temperature, aqueous hydrochloric acid (1 N, 2.2 L) was added over 20 minutes. The mixture was stirred at room temperature for 20 minutes, and then the layers were allowed to separate. The aqueous layer was removed and back extracted with ethyl acetate (1.75 L). The combined organic layers were washed with water (1 L) and the organic layer concentrated via distillation (4 L solvent removed). Ethyl acetate (1.8 L) was added and the solution was concentrated to a minimum stirring volume. Ethyl acetate (3 L) and methanol (0.8 L) were added and the solution was cooled to 0° C. Acetyl chloride (401 mL) was added dropwise over 20 minutes and the solution was stirred at 0° C. for 4 hours. The precipitate was collected by filtration under nitrogen. The filtrate was washed with ethyl acetate (0.5 L) and dried in a vacuum oven at 40° C. to afford the I-1A-1e as an off-white solid (241 g). $^1$H NMR (400 MHz, CD$_3$OD) δ ppm 7.43 (s, 1H), 5.32-5.42 (m, 1H), 3.15-3.25 (m, 4H), 2.89 (s, 2H), 2.64 (s, 2H), 1.69-1.90 (m, 4H), 1.37-1.45 (m, 6H); +ESI (M+H) =248.4

Preparation I-1A-2: benzyl 9-oxo-3-azaspiro[5.5]undec-7-ene-3-carboxylate

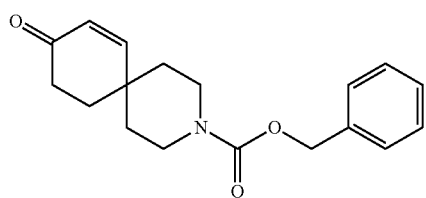

I-1A-2

To a benzene (700 mL) solution of benzyl 4-formylpiperidine-1-carboxylate (90.0 g, 363.9 mmol) stirring in a 2 L 3-neck flask fitted with a Dean-Stark trap was added p-toluenesulfonic acid (6.92 g, 36.4 mmol). The reaction was heated to 70° C., 3-buten-2-one (61.8 mL, 753 mmol) was added and mixture was heated at reflux for 24 hours collecting expelled water in the trap. The reaction was cooled to room temperature and washed with 500 mL saturated aqueous sodium bicarbonate. The organic phase was dried over sodium sulfate, filtered and concentrated. The resultant dark brown oil was taken up in 200 mL dichloromethane and filtered through a silica pad (600 mL silica), eluting with 2 L heptane followed by 3 L 50% ethyl acetate/heptane and then 3 L ethyl acetate, collecting by 1 L fractions. Fractions containing dean product were combined and concentrated to yield 68.1 g of the title compound as a thick brown oil. The fractions containing impure product were combined and concentrated and purified by flash chromatography (10-80% ethyl acetate/heptane, 340 g silica gel) to yield an additional 23.6 g of the title compound as a thick brown oil. Combined yield of 91.7 g, (94.1%) was realized. $^1$H NMR (400 MHz, CDCl$_3$) δ ppm 7.27-7.43 (m, 5H), 6.79 (d, J=10.3 Hz, 1H), 5.95 (d, J=10.3 Hz, 1H), 5.13 (s, 2H), 3.56-3.71 (m, 2H), 3.39-3.55 (m, 2H), 2.38-2.50 (m, 2H), 1.96 (t, J=6.7 Hz, 2H), 1.70-1.52 (m, 4H).

Preparation I-1A-2a: Benzyl 10-((dimethylamino)methylene)-9-oxo-3-azaspiro[5.5]undec-7-ene-3-carboxylate

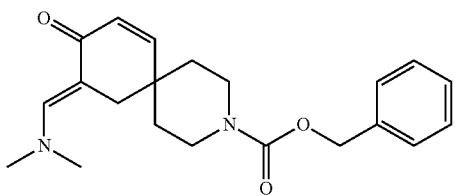

I-1A-2a 9-oxo-3-aza-spiro[5.5]undec-7-ene-3-carboxylic acid benzyl ester. Preparation I-1A-2 (15.2 g, 51 mmol) was dissolved in 180 mL toluene and tris(dimethylamino)methane (222 g, 27 mmol) was added. The reaction was heated to reflux for 5 hours and then allowed to cool to room temperature overnight. The reaction solution was concentrated in vacuo to provide the title compound (18.0 g, 100%): +APCI MS (M+H) 354.6; $^1$H NMR (400 MHz, CDC$_3$) δ ppm 7.49 (s, 1H), 7.28-7.40 (m, 5H), 6.59 (d, J=10.16 Hz, 1H), 6.01 (d, J=9.97 Hz, 1H), 5.13 (s, 2H), 3.52-3.66 (m, 2H), 3.39-3.52 (m, 2H), 3.07 (s, 6H), 2.74 (s, 2H), 1.58-1.73 (m, 2H), 1.41-1.58 (m, 2H).

Preparation I-1A-2b: benzyl 1-tert-butyl-1,4-dihydrospiro[indazole-5,4'-piperidine]-1'-carboxylate

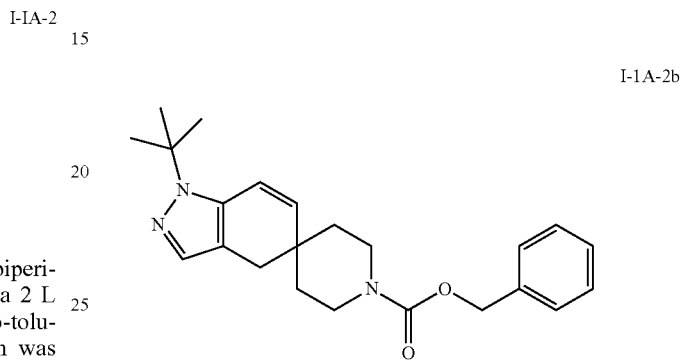

I-1A-2b

Preparation I-1A-2a (59.2 g, 167 mmol) was dissolved in 835 mL of ethanol. To the reaction solution was added acetic acid (20 mL, 345 mmol) and tert-butylhydrazine hydrochloride (29.1 g, 234 mmol). The reaction was heated to reflux for 1 hour. The reaction solution was cooled to room temperature and then concentrated in vacuo to give an orange oil which was purified by flash chromatography using 20-40% ethyl acetate in heptane as eluent to afford the title compound as a pale yellow solid (50 g, 79%): +ESI MS (M+H) 380.5; $^1$H NMR (400 MHz, CDCl$_3$) δ ppm 7.26-7.40 (m, 5H) 7.17 (s, 1H) 6.66 (d, J=9.95 Hz, 1H) 5.77 (d, J=10.15 Hz, 1H) 5.12 (s, 2H) 3.38-3.64 (m, 4H) 2.58 (s, 2H) 1.60 (s, 12H) 1.50 (br. s., 1H).

Preparation I-1A-2c: benzyl 6-bromo-1-tert-butyl-7-hydroxy-1,4,6,7-tetrahydrospiro[indazole-5,4'-piperidine]-1'-carboxylate

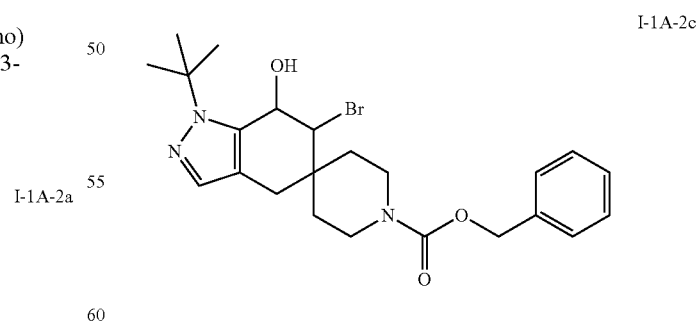

I-1A-2c

Preparation I-1A-2b (50 g, 132 mmol) was dissolved in 1 L of tetrahydrofuran. To the reaction was added N-bromosuccinimide (24.6 g, 138 mmol) and 250 mL of water. The reaction was stirred for 1 hour at room temperature. The reaction was partitioned between ethyl acetate and water. The phases were separated and the organic phase was washed an additional 2 times with water and once with saturated aqueous sodium chloride. The organic phase was dried over magnesium sulfate, concentrated in vacuo, and crystallized from ether to afford the title compound as a cream-colored solid (60.7 g, 97%): +ESI MS (M+H) 476.5; ¹H NMR (400 MHz, CDCl₃) δ ppm 7.28-7.36 (m, 5H), 7.27 (s, 1H), 523 (t, —4.68 Hz, 1H), 5.12 (s, 2H), 4.24 (d, J=4.49 Hz, 1H), 3.87 (br. s., 2H), 3.12 (br. s., 2H), 2.79 (d, J=16.00 Hz, 2H), 2.59 (d, J=15.80 Hz, 2H), 1.95 (br. s., 1H), 1.66 (s, 11H), 1.58 (br. s., 1 H).

Preparation I-1A-2d: benzyl 6-bromo-1-tert-butyl-7-oxo-1,4,6,7-tetrahydrospiro[indazole-5,4'-piperidine]-1'-carboxylate

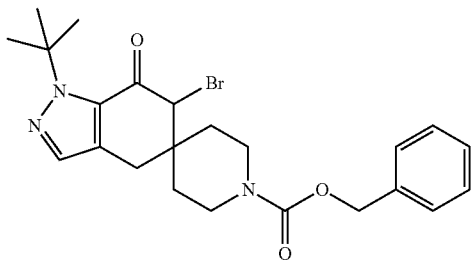

I-1A-2d

Preparation I-1A-2c (57.9 g, 122 mmol) was dissolved in 1 L acetone and then cooled to 0° C. in an ice bath. To the solution was added 122 mL of Jones Reagent (Fillion, E. *Tetrahedron Letters* 2004, 46, 1091-1094). The ice bath was removed and the reaction was allowed to warm to room temperature where it was stirred for 45 minutes. Saturated, aqueous sodium bicarbonate was added until no further gas evolution was noted and pH reached 7. The resulting mixture was filtered through a pad of Celite® rinsing with ethyl acetate. The filtrate layers were separated and the aqueous layer was back extracted with ethyl acetate. The organic extracts were combined, washed twice with water, once with saturated aqueous sodium chloride, dried over magnesium sulfate and concentrated in vacuo. The residue was crystallized from ethyl acetate/heptane to afford the title compound (50.4 g, 87%): +ESI MS (M+H) 474.5; ¹H NMR (400 MHz, CDCl₃) δ ppm 7.32 (d, J=9.38 Hz, 6H), 5.11 (s, 2H), 4.24 (s, 1H), 3.58-3.84 (m, 2H), 3.16-3.41 (m, 2H), 2.67-2.91 (m, 2H), 1.80 (br. s., 1H), 1.61-1.76 (m, 11H), 1.52-1.61 (m, 1H).

Preparation I-1A-2e: benzyl 1-tert-butyl-7-oxo-1,4,6,7-tetrahydrospiro[indazole-5,4'-piperidine]-1'-carboxylate

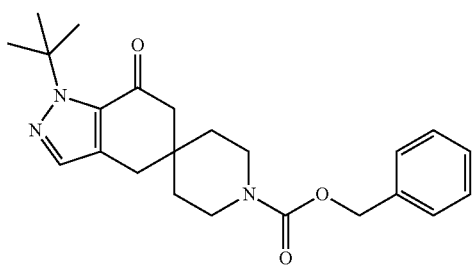

I-1A-2e

Preparation I-1A-2d (50.4 g, 106 mmol) was dissolved in 600 mL of tetrahydrofuran, to this was added saturated aqueous ammonium chloride (600 mL) and zinc powder (20.8 g, 319 mmol). The reaction was stirred for 30 minutes at room temperature. The reaction was filtered through Celite®, the phases were separated and the organic phase was washed with water and saturated aqueous sodium chloride, dried over magnesium sulfate and concentrated in vacuo to give a foam. The foam was triturated once in ethyl acetate/heptane and once in ether and filtered to afford the title compound as a white solid (40.4 g, 96%): +ESI MS (M+H) 396.5; ¹H NMR (400 MHz, CDCl₃) δ ppm 7.24-7.38 (m, 6H), 5.11 (s, 2H), 3.36-3.61 (m, 4H), 2.74 (s, 2H), 2.54 (s, 2H), 1.64 (s, 9H), 1.51 (br. s., 4H).

Preparation I-1A-2f: 1-tert-butyl-4,6-dihydrospiro[indazole-5,4'-piperidin]-7(1H)-one (1-A-2f)

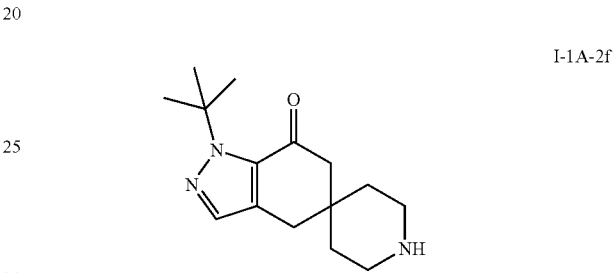

I-1A-2f

Preparation I-1A-2e (46.6 g, 118 mmol) was dissolved in 730 mL ethanol and the solution was added to 10% palladium on carbon (9.4 g). To this was added 1-methyl-1,4-cyclohexadiene (90 mL, 769 mmol). The reaction was stirred at reflux for 2 hours. The reaction was cooled to room temperature and filtered through Celite®. The filtrate was concentrated in vacuo to give a gray solid. The solid was dissolved in 150 mL ethyl acetate, to this was added 35 mL 4 M hydrochloric acid in dioxane. A precipitate formed and was collected by filtration to afford the title compound as a white solid (34 g, 97%): +ESI MS (M+H) 262.5; ¹H NMR (400 MHz, CD₃OD) δ ppm 7.34 (s, 1H) 3.12-3.25 (m, 4H) 2.90 (s, 2H) 2.66 (s, 2H) 1.67-1.85 (m, 4H) 1.62 (s, 9H).

Preparation I-2A-42a: tert-butyl 1-(2-ethoxy-2-oxoethyl-1,4-dihydrospiro[indazole-5,4'-piperidine]-1'-carboxylate

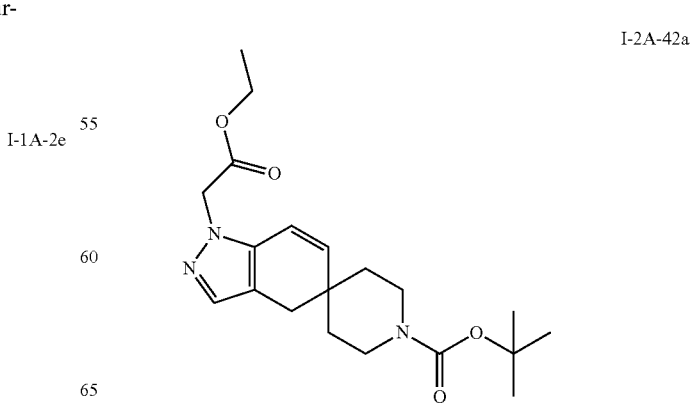

I-2A-42a

Ethylhydrazinoacetate hydrochloride (0.92 g, 5.95 mmol) was added to a solution of Preparation I-1A-2a (1.25 g, 3.90 mmol) in ethanol (30 mL). Stir the mixture at reflux for 1 hour. An aliquot indicated the reaction was complete by $^1$HNMR. The reaction mixture was cooled to room temperature and concentrated under high vacuum to a brown oil. The oil was triturated with diethyl ether (50 mL). The precipitate was filtered and the filtrate concentrated and dried under high vacuum to yield the title compound (1.50 g, 100%) as a brown oil. +APCI MS (M+H) 3762; $^1$H NMR (400 MHz, CDCl$_3$) δ ppm 1.21-1.26 (m, 3H), 1.43 (s, 9H), 1.45-1.52 (m, 2H), 1.54-1.64 (m, 2H), 2.62 (s, 2H), 3.33-3.49 (m, 4H), 4.15-4.22 (m, 2H), 4.82 (s, 2H), 5.87 (d, J=9.97 Hz, 1H), 6.26 (d, J=9.97 Hz, 1H), 7.24 (s, 1H).

Preparation I-2A-42b: diethyl 2-(1'-(tert-butoxycarbonyl)spiro[indazole-5,4'-piperidine]-1(4H)-yl)malonate

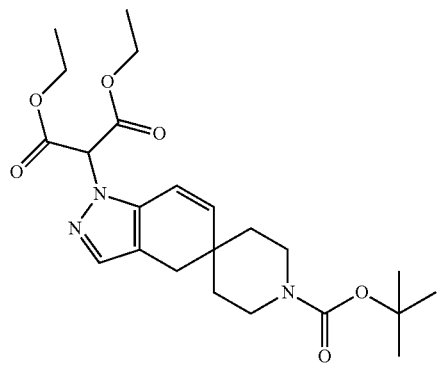

I-2A-42b

Preparation I-2A-42a (1.45 g 3.86 mmol) in toluene (5 mL) was added to a suspension of sodium hydride (0.148 g, 60% dispersion in mineral oil) in diethyl carbonate (30 mL), dropwise at 80° C. over 30 minutes. The reaction was stirred at reflux for 1.5 hours. $^1$H NMR indicated that starting material was consumed and that the desired product had formed. The reaction mixture was cooled to room temperature. Methanol (1 mL) was added and the solution was stirred at room temperature for 5 minutes. Water (5 mL) was added. The solution was acidified to pH~3 with 2 N aqueous, hydrochloric acid (3 mL) then was extracted with dichloromethane (3×15 mL). The combined organics were dried over magnesium sulfate, filtered, concentrated, and dried under high vacuum to yield a brown gum (1.59 g, 92%). The crude material was triturated with 1:1 diethyl ether: heptanes (50 mL). The precipitate was filtered. The filtrate was concentrated and dried under high vacuum to yield the title compound (1.25 g, 72%). +APCI MS (M+H) 348.1; $^1$H NMR (400 MHz, CDCl$_3$) δ ppm 1.13-1.32 (m, 6H), 1.40-1.46 (m, 9H), 1.46-1.54 (m, 2H), 1.59 (d, J=13.68 Hz, 3H), 2.62 (s, 2H), 3.31-3.51 (m, 4H), 4.27 (q, J=7.23 Hz, 4H), 5.85 (d, J=9.97 Hz, 1H), 6.34 (d, J=9.97 Hz, 1H), 7.24 (s, 1H).

Preparation I-2A-42c: tert-butyl 1-(1,3-dihydroxypropan-2-yl)-1,4-dihydrospiro[indazole-5,4'-piperidine]-1'-carboxylate

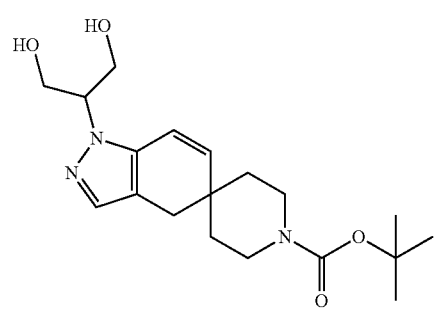

I-2A-42c

Tetrahydrofuran (40 mL) was added to lithium aluminum hydride (900 mg) in a 3-neck, 125 mL round bottom flask equipped with a nitrogen inlet and thermometer. The solution was cooled to −2° C. Preparation I-2A-42b (1 g) in tetrahydrofuran (5 mL) was added dropwise over 5 minutes. The temperature was never greater than −0.2° C. during the addition. The reaction was stirred at 0° C. for 3 hours then the reaction was then quenched through the sequential addition of water (1.0 mL). 15% aqueous sodium hydroxide (1.0 mL), and water (3 mL). The internal temperature was never greater than 3.2° C. during the addition. The reaction was then allowed to warm to room temperature over 15 minutes. The reaction mixture was filtered through Celite® and washed with diethyl ether (3×20 mL). The combined organics were washed with brine (5 mL) dried over sodium sulfate, filtered, concentrated, and dried under high vacuum to yield a pale yellow glass (548 mg, 67%). This material was chromatographed on 25 g of silica eluting with 2% to 8% methanol in dichloromethane with 0.1% ammonium hydroxide over 30 minutes to yield the title compound (133 mg, 16%). +APCI MS (M+H) 364.2; $^1$H NMR (400 MHz, CDCl$_3$) δ ppm 1.45 (s, 9H), 1.51 (br. s., 2H), 1.60 (br. s., 4H), 2.62 (s, 2H), 3.32-3.53 (m, 4H), 4.05 (br. s., 4H), 4.26 (t, J=4.89 Hz, 1H), 5.89 (s, 1H), 6.40 (d, J=9.77 Hz, 1H), 7.23-7.25 (m, 1H).

Preparation I-2A-42d: tert-butyl 1-(oxetan-3-yl)-1,4-dihydrospiro[indazole-5,4'-piperidine]-1'-carboxylate

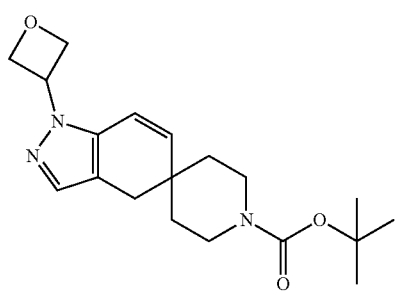

I-2A-42d 2.5 M n-butyl lithium in hexanes (0.33 ml, 165 uL) was added to a solution of Preparation I-2A-42c (150 mg. 0.41 mmol) in tetrahydrofuran (8 mL) at −6.2° C. The temperature was never greater than −3.7° C. during the addition. The solution was stirred at −8° C. for 30 minutes. A solution of p-toluenesulfonyl chloride (79 mg) in tetrahydrofuran (2 mL) was added to the reaction mixture at −5° C. The temperature was never greater than −2° C. during the addition. The reaction was stirred at −5° C. for 1 hour then the reaction mixture was cooled to −6° C. and 2.5 M n-butyl lithium in hexanes (0.33 mL, 165 uL) was added over 2 minutes. The temperature was never greater than −3.5° C. during the addition. The cooling to bath was removed and the reaction was stirred at an internal temperature of 60° C. for 16 hours. The reaction mixture was cooled to room temperature and ethyl acetate (20 mL) was added. The reaction solution was washed with water (35 mL) and the aqueous layer was extracted with ethyl acetate (15 mL). The combined organics were washed with brine (5 mL) dried over magnesium sulfate, filtered, concentrated, and dried under high vacuum to yield a yellow solid. The solid was purified by chromatography on 8 g silica eluting with 25% to 75% ethyl acetate in heptanes over 36 minutes to yield the title compound (58 mg, 40%). +ESI MS (M+H); ¹H NMR (400 MHz, CDCl₃) δ ppm 1.45 (s, 9H), 1.49 (d, J=3.71 Hz, 1H), 1.55 (s, 4H), 1.59 (br. s., 1H), 2.61 (s, 2H), 3.32-3.50 (m, 4H), 5.00 (m, J=7.22, 7.22 Hz, 2H), 5.13 (t, J=6.44 Hz, 2H), 5.36-5.46 (m, 1H), 5.88 (d, J=9.95 Hz, 1H), 6.43 (d, J=9.95 Hz, 1H), 7.33 (s, 1H).

Preparation I-2A-42e: tert-butyl 6-bromo-7-methoxy-1-(oxetan-3-yl)-1,4,6,7-tetrahydrospiro[indazole-5,4'-piperidine]-1'-carboxylate

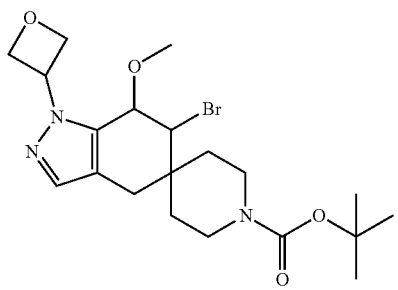

I-2A-42e

N-bromosuccinimide (30 mg, 0.17 mmol) was added to Preparation I-2A-42d (56 mg, 0.17 mmol) in methanol (1.0 mL) at room temperature. The reaction was stirred at room temperature for 2 hours then N-bromosuccinimide (4.5 mg) was added and the reaction mixture was stirred at room temperature for 1 hour. The reaction mixture was concentrated under a stream of nitrogen to a residue. Ethyl acetate (15 mL) was added and the reaction solution was washed with 10% citric acid (3 mL), 1N sodium hydroxide (3 mL), and brine (3 mL). The organic layer was concentrated and dried under high vacuum to yield the title compound (74 mg, 100%) as a colorless solid. +APCI MS (M+H) 458.2; ¹H NMR (400 MHz, CDCl₃) ppm 1.44 (s, 9H), 1.69 (br. s., 4H), 2.51 (d, J=15.83 Hz, 1H), 2.67 (d, J=15.83 Hz, 1H), 3.06-3.31 (m, 3H), 3.54 (s, 3H), 3.62-3.72 (m, 1H), 4.39 (s, 1H), 4.66 (s, 1H), 4.87-4.93 (m, 1H), 4.97 (t. J=6.84 Hz, 1H), 4.99-5.04 (m, 1H), 5.30 (s, 1H), 5.34-5.40 (m, 1H), 7.43 (s, 1H).

Preparation I-2A-42f: tert-butyl 1-(oxetan-3-yl)-7-oxo-1,4,6,7-tetrahydrospiro[indazole-5,4'-piperidine]-1'-carboxylate

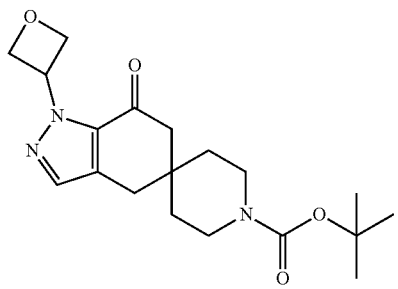

I-2A-42f

1 M potassium tert-butoxide in tetrahydrofuran (0.320 mL) was added to a solution of Preparation I-2A-42e (72 mg, 0.16 mmol) in tetrahydrofuran (1.0 mL) at room temperature. The colorless solution turned yellow upon addition. The solution was stirred at room temperature for 16 hours. 1 N aqueous, hydrogen chloride (0.475 mL, 3 eq.) was added and the solution was stirred at room temperature for 1 hour. The tetrahydrofuran was concentrated under a stream of nitrogen. The aqueous phase was extracted with ethyl acetate (3×5 mL). The combined organics were washed with brine (3 mL) then the organic layer was concentrated and dried under high vacuum to give the title compound as a pale yellow solid (54 mg, 96%). -APCI MS (M−H) 360.2; ¹H NMR (400 MHz, CD₃OD) δ ppm 1.38-1.45 (m, 9H), 1.46-1.56 (m, 4H), 2.57 (s, 2H), 2.82 (s, 2H), 3.33-3.53 (m, 4H), 4.94-5.06 (m, 4H), 6.08-621 (m, 1H), 7.53 (s, 1H).

Preparation I-2A-42g: 1-(oxetan-3-yl 4,6-dihydrospiro[indazole-5,4'-piperidin]-7(1H)-one

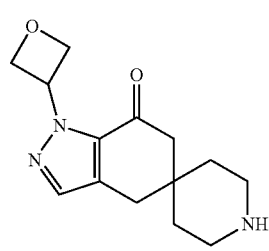

I-2A-42q

Trifluoroacetic acid (0.2 mL) was added to a solution of Preparation I-2A-42f (50 mg, 0.14 mmol) in dichloromethane (2 mL) at 0° C. The cooling bath was removed and the reaction was stirred at room temperature for 1.5 hours. The reaction mixture was concentrated to a residue under a stream of nitrogen and dried under high vacuum for 20 minutes. The residue was triturated with diethyl ether (5 mL). The solvent was decanted and the resulting precipitate was dried under high vacuum to yield the title compound (52 mg. 100) as a pale yellow solid. +APCI MS (M+H) 262.2; ¹H NMR (400 MHz, CD₃OD) δ ppm 1.65-1.86 (m, 4H), 2.63 (s, 2H), 2.89 (s, 2H), 3.14-327 (m, 4H), 5.02 (s, 4H), 6.07-6.21 (m, 1H), 7.53-7.60 (m, 1H).

Preparation I-2A-75a: Benzyl 1-isopropyl-1,4-dihydrospiro(indazole-5,4'-piperidine-1'-carboxylate

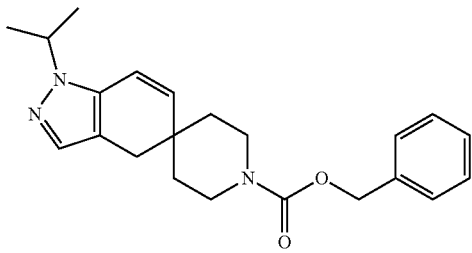

I-2A-75a

Preparation I-1A-2a (6.38 g, 18 mmol) was dissolved in 90 mL of ethanol. To the reaction solution was added acetic acid (2.16 g, 36 mm) and 1-isopropylhydrazine hydrochloride (2.79 g, 25 mmol). The reaction was heated to reflux for 2 hours then the reaction solution was cooled to room temperature and concentrated in vacuo to give an orange oil which was purified by flash chromatography using 12-100% ethyl acetate in heptane as eluent to afford the title compound as a yellow gum (6.58 g, 69%): +ESI MS (M+H) 366.5; $^1$H NMR (400 MHz, CDCl$_3$) δ ppm 7.28-7.39 (m, 5H), 7.25 (s, 1H), 6.42 (d, J=9.95 Hz, 1H), 5.84 (d, J=9.95 Hz, 1H), 5.14 (s, 2H), 4.41-4.54 (m, 1H), 3.42-3.65 (m, 4H), 2.62 (s, 2H), 1.58-1.70 (m, 2H), 1.50-1.58 (m, 2H), 1.49 (d, J=6.83 Hz, 6H).

Preparation I-2A-75b: benzyl 3,6-dibromo-1-isopropyl-7-methoxy-1,4,6,7-tetrahydrospiro[indazole-5,4'-piperidine]-1'-carboxylate

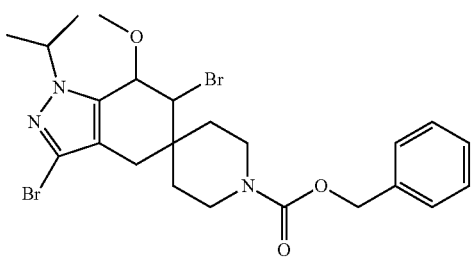

I-2A-75b

Preparation I-2A-75a (679 mg, 1.86 mmol) was dissolved in 15 mL methanol and treated with N-bromosuccinimide (728 mg, 4.09 mmol) and the reaction was stirred at ambient temperature for 18 hours. The methanol was removed under reduced pressure. The resultant tan foam was taken up in 50 mL ethyl acetate and washed with 0.5 M sodium hydroxide (2×50 mL) and 20 mL saturated aqueous sodium thiosulfate. The organic phase was dried over sodium sulfate, filtered and concentrated. The resultant oil was flash chromatographed (25 g silica, 10-80% ethyl acetate/heptane gradient) to yield 784 mg (76%) of the title compound as a white foam: +APCI-MS (M+H)=554.1, 556.2, 558.2: $^1$H NMR (400 MHz, CDCl$_3$) δ ppm 726-7.42 (m, 5H), 5.12 (s, 2H), 4.67 (d, J=1.76 Hz, 1H), 4.36 (s, 1H), 4.27 (m, 1H), 3.79 (d, J=11.90 Hz, 1H), 3.59-3.73 (m, 1H), 3.53 (s, 3H), 3.24-3.40 (m, 1H), 3.19 (ddd, J=13.61, 10.00, 3.12 Hz, 1H), 2.56 (d, J=16.19 Hz, 1H), 2.34 (d, J=16.19 Hz, 1H), 1.56-1.85 (m, 4H), 1.38-1.55 (m, 6H).

Preparation I-2A-75c: benzyl 3-bromo-1-isopropyl-7-oxo-1,4,6,7-tetrahydrospiro[indazole-5,4'-piperidine]-1'-carboxylate

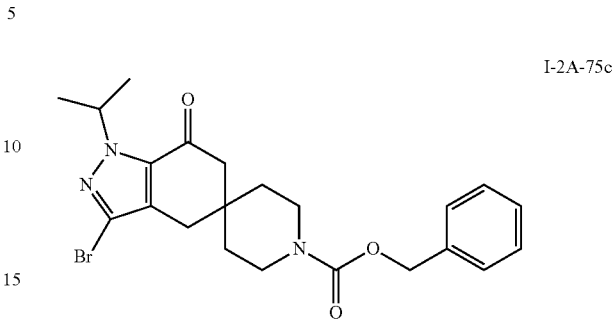

I-2A-75c

Preparation I-2A-75b (784 mg. 1.4 mmol) was dissolved in 15 mL tetrahydrofuran. Potassium t-butoxide (2.82 mL, 2 eq, 1 M tetrahydrofuran) was added and the reaction was stirred for 18 hours at ambient temperature. To the reaction was added 25 mL 2 N hydrochloric acid. The mixture was stirred for 30 minutes at ambient temperature. The mixture was diluted with 25 mL water and extracted with ethyl acetate (2×50 mL). The organic extracts were combined and dried over sodium sulfate, filtered and concentrated. The resultant oil was flash chromatographed (50 g silica, 8-66% ethyl acetate/heptane gradient) to yield 612 mg of the title compound as a white foam: +ESI MS (M+H)=462.5 $^1$H NMR (400 MHz, CDCl$_3$) δ ppm 7.25-7.38 (m, 5H), 5.24-5.42 (m, 1H), 5.12 (s, 2H), 3.49-3.66 (m, 2H), 3.46 (dd, J=7.41, 4.88 Hz, 2H), 2.63 (s, 2H), 2.52 (s, 2H), 1.48-1.65 (m, 4H), 1.44 (d. J=6.63 Hz, 6H).

Preparation I-2A-75d: tert-butyl 3-bromo-1-isopropyl-7-oxo-1,4,6,7-tetrahydrospiro[indazole-5,4'-piperidine]-1'-carboxylate

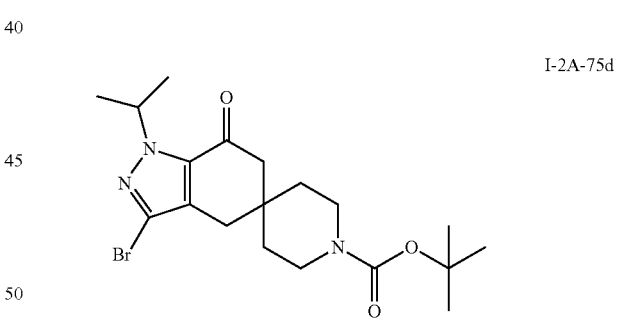

I-2A-75d

Preparation I-2A-75c (612 mg, 1.33 mmol) was dissolved in 10 mL 33% hydrobromic acid/acetic acid and the mixture was stirred for 60 minutes at ambient temperature. The solvent was evaporated and the red-orange residue taken up in 50 mL water and made basic with saturated aqueous sodium carbonate and extracted with ethyl acetate (2×50 mL). The organic phase was concentrated to 20 mL and treated with 20 mL saturated aqueous sodium bicarbonate and di-tert-butyl dicarbonate (348 mg). The biphasic mixture stirred for one hour at ambient temperature. The layers were separated and the organic phase dried over sodium sulfate, filtered and concentrated under reduced pressure. The resultant oil was flash chromatographed (10-70% ethyl acetate/heptane. 10 g silica) to yield 364 mg of the title compound. +ESI MS (M+H) =413.5; $^1$H NMR (400 MHz, CDCl$_3$) 5 ppm 5.24-5.43 (m, 1H) 3.41-3.56 (m, 2H) 3.28-3.41 (m, 2H) 2.63 (s, 2H) 2.51 (s, 2H) 1.47-1.56 (m, 4H) 1.40-1.49 (m, 15H).

Preparation I-2A-75e: tert-butyl 1-isopropyl-3-methyl-7-oxo-1,4,6,7-tetrahydrospiro[indazole-5,4'-piperidine]-1'-carboxylate

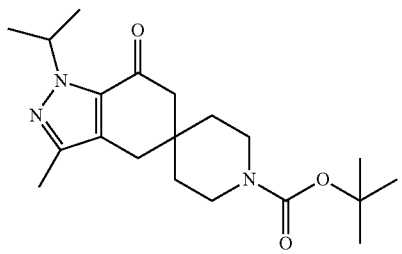

I-2A-75e

Preparation I-2A-75d (440 mg, 1.03 mmol), paladium tetrakis triphenylphosphine (119 mg, 0.103 mmol), potassium carbonate (146 mg, 1.03 mmol), and water (94 mg, 5.16 mmol) were combined in dimethylformamide (2 mL) and degassed with nitrogen for 2 minutes. The reaction vial was sealed and heated in a microwave reactor for 30 minutes at 100° C. The vial was removed from the microwave reactor and then heated to 100° C. in a conventional heating block for 4 days. The reaction was concentrated in vacuo and then partitioned between water (5 mL) and ethyl acetate (5 mL). The phases were separated and the organic layer was concentrated and then chromatographed on a 40 g column eluting with 20-40% ethyl acetate in heptane gradient to give 268 mg (72%) of the title compound. +ESI MS (M+H)=362.5; $^1$H NMR (400 MHz, CDC$_3$) 5 ppm 5.20-5.53 (m, 1H), 3.32-3.54 (m, 4H), 2.62 (s, 2H), 2.50 (s, 2H), 2.23 (s, 3H), 1.53 (t, J=5.76 Hz, 4H), 1.46 (s, 9H), 1.44 (d, J=6.64 Hz, 6H).

Preparation I-2A-75f: 1-isopropyl-3-methyl-4,6-dihydrospiro[indazole-5,4'-piperidin]-7(1H)-one

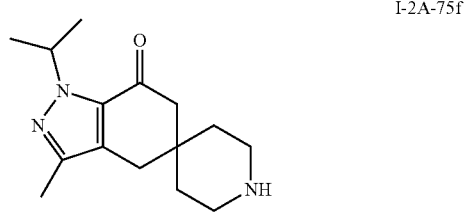 [SMILES: Cc1nn(C(C)C)c2c1CC1(CCNCC1)CC2=O]

I-2A-75f

Preparation I-2A-75e (375 mg, 1.04 mmol) was dissolved in 3 mL diethyl ether and treated with 4 M hydrogen chloride in dioxane (1 mL). The solution was stirred for one hour and then concentrated in vacuo to provide 300 mg of the title compound as a white foam: $^1$H NMR (400 MHz, DMSO-d$_6$) δ ppm 5.10-5.35 (m, 1H), 4.34 (br. s., 4H), 2.70 (s, 2H), 2.56 (s, 2H), 2.17 (s, 3H), 1.66 (br. s., 4H), 1.34 (d, J=6.64 Hz, 6H).

Preparation I-2A-76a: tert-butyl 3-cyano-1-isopropyl-7-oxo-1,4,6,7-tetrahydrospiro[indazole-5,4'-piperidine]-1'-carboxylate

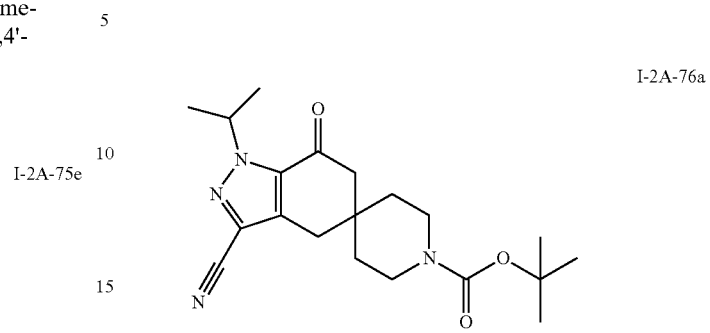

I-2A-76a

In a schlenk tube flushed with nitrogen was added Preparation I-2A-75d (250 mg, 0.59 mmol), tris(dibenzylideneacetone)dipalladium(0)-chloroform adduct (23.8 mg, 0.02 mmol), zinc dust (9.6 mg, 0.15 mmol), zinc cyanide (75.7 mg, 0.65 mmol) and 1,1'-bis(diphenylphosphino)ferrocene (26.1 mg, 0.05 mmol). Anhydrous dimethylacetamide (3.5 mL) was added and the flask was flushed with nitrogen, then capped with a Teflon® screw top. The reaction was stirred at 120° C. for 16 hours. The reaction was cooled and then filtered through a pad of Celite® washing with ethyl acetate. The filtrate was washed with water and the aqueous phase was back extracted with ethyl acetate. The combined organic phases were washed with saturated aqueous sodium chloride, dried over magnesium sulfate and concentrated in vacuo. The residue was purified by flash chromatography using 5-30% ethyl acetate in heptane gradient to give 204 mg of the title compound as a solid (93%): 20+ESI MS (M-Boc+H) 273.5; $^1$H NMR (400 MHz, CD$_3$OD) δ ppm 5.44 (m, 1H), 3.44 (m, 4H), 2.89 (s, 2H), 2.64 (s, 2H), 1.53 (m, 4H), 1.46-1.43 (m, 15H).

Preparation I-8a-1b: 1-isopropyl-7-oxo-1,4,6,7-tetrahydrospiro[indazole-5,4'-piperidine]-3-carbonitrile

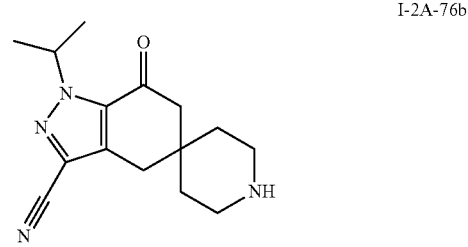 [SMILES: CC(C)n1nc(C#N)c2c1C(=O)CC1(CCNCC1)C2]

I-2A-76b

Preparation I-2A-76a (70 mg, 0.19 mmol) was dissolved in dichloromethane (3 mL) and trifluoroacetic acid (0.2 mL) and stirred at ambient temperature for 90 minutes. The solvent was concentrated in vacuo and the residue was co-distilled with toluene followed by ethyl acetate to give 149 mg (100%) of the title compound as a yellow solid: +ESI MS (M+H) 273.5.

Preparation I-4A-1a: Benzyl 6-bromo-7-hydroxy-1-isopropyl-1,4,6,7-tetrahydrospiro[indazole-5,4'-piperidine]-1'-carboxylate

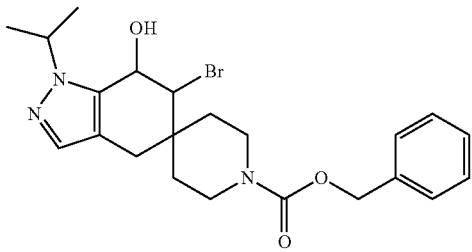

I-4A-1a

Preparation I-2A-75a (4.20 g, 11 mmol) was dissolved in 130 mL of tetrahydrofuran. To the reaction was added N-bromosuccinimide (2.49 g, 14 mmol) and 30 mL of water. The reaction was stirred for 1 hour at room temperature. The reaction was partitioned between ethyl acetate and saturated, aqueous sodium chloride. The organic phase was separated then washed an additional time with saturated aqueous sodium chloride. The organic phase was dried over sodium sulfate and concentrated in vacuo to afford the title compound as an off-white foam (5.31 g, 100%): +ESI MS (M+H) 463.8.

Preparation I-4A-1b: Benzyl 6-bromo-1-isopropyl-7-oxo-1,4,6,7-tetrahydrospiro[indazole-5,4'-piperidine]-1'-carboxylate

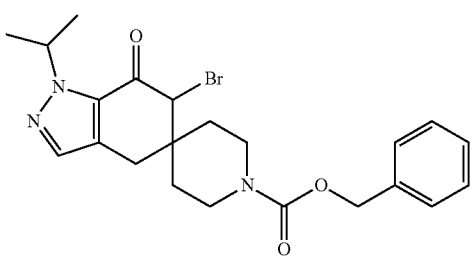

I-4A-1b

Preparation 14A-1a (5.30 g, 11 mmol) was dissolved in 53 mL acetone and then cooled to 0° C. in an ice bath. To the solution was added 83 mL of Jones Reagent (Filion, E. *Tetrahedron Letters* 2004, 46, 1091-1094). The ice bath was removed and the reaction was allowed to warm to room temperature where it was stirred for 45 minutes. The reaction was cooled to 0° C. in an ice bath and then saturated, aqueous sodium bicarbonate was added until no further gas evolution was noted. The resulting mixture was filtered through a pad of Celite® rinsing with ethyl acetate. The filtrate layers were separated and the aqueous layer was back extracted with ethyl acetate. The organic extracts were combined, washed twice with water, once with saturated, aqueous sodium chloride, dried over sodium sulfate and concentrated in vacuo to afford the title compound (5.27 g, 100%): +ESI MS (M+H) 460.4.

Preparation I-4A-1c: Benzyl 6-bromo-1-isopropyl-7-oxo-1,4,6,7-tetrahydrospiro[indazole-5,4'-piperidine]-1'-carboxylate

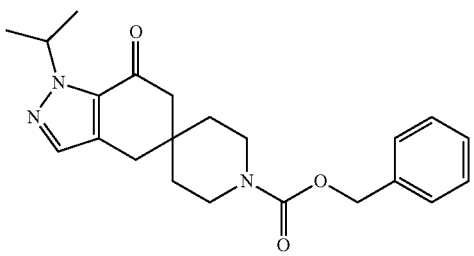

I-4A-1c

Preparation I-4A-1b (5.63 g, 12 mmol) was dissolved in 55 mL of acetic acid, to this was added zinc powder (2.40 g, 37 mmol). The reaction was stirred for 35 minutes at room temperature. The reaction was concentrated in vacuo and then partitioned between saturated, aqueous sodium bicarbonate and ethyl acetate. The phases were separated and the aqueous phase was extracted with ethyl acetate. The organic extracts were combined, washed with water, saturated, aqueous sodium chloride, dried over sodium sulfate and concentrated in vacuo to give an oil. The oil was purified by flash chromatography using 12-100% ethyl acetate in heptane as eluent to afford the title compound as an oil (2.25 g, 48%): +ESI MS (M+H) 382.4; $^1$H NMR (400 MHz, CDCl$_3$) δ ppm 7.28-7.40 (m, 6H), 5.32-5.45 (m, 1H), 5.13 (s, 2H), 3.41-3.61 (m, 4H), 2.76 (s, 2H), 2.54 (s, 2H), 1.50-1.62 (m, 4H), 1.47 (d, J=6.63 Hz, 6H).

Preparation I-4A-1d: Benzyl 1-isopropyl-6-methyl-7-oxo-1,4,6,7-tetrahydrospiro[indazole-5,4'-piperidine]-1'-carboxylate

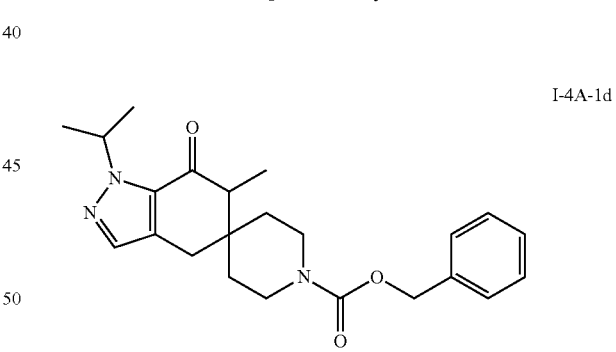

I-4A-1d

Preparation I-4A-1c (397 mg, 1.04 mmol) in tetrahydrofuran (8 mL) was coded to −70° C. To this was added lithium bis(trimethylsilyl)amide (1.56 mL 1.56 mmol) as a 1.0 M solution in tetrahydrofuran over a ten minute period. The resulting yellow solution was stirred for thirty minutes at −70° C. 1,3-Dimethyl-3,4,5,6-tetrahydro-2(H)-pyrimidinone (1.6 mL) was added to the reaction, stirring was continued at −70° C. for ten minutes. To the reaction was added iodomethane (746 mg, 5.2 mmol). The reaction was allowed to warm to room temperature where it was stirred for 18 hours. To the reaction was added saturated, aqueous sodium bicarbonate (2 mL), the mixture was then partitioned between water (20 mL) and ethyl acetate (150 mL). The layers were separated and the aqueous layer was extracted with ethyl acetate (150 mL). The organic layers were combined, dried over magnesium sulfate, filtered and then concentrated to give a clear oil. The oil was purified by silica gel chromatography using 10-40% ethyl acetate in heptane as eluent to afford the title compound as a white solid (351 mg, 85%): +ESI MS (M+H) 3962; $^1$H NMR (400 MHz, DMSO-$d_6$) δ ppm 7.44 (s, 1H), 7.35 (s, 5H), 5.17-5.34 (m, 1H), 5.06 (s, 2H), 3.52-3.72 (m, 4H), 2.79 (s, 2H), 2.42-2.48 (m, 1H), 1.38-1.49 (m, 4H), 1.35 (t, J=6.74 Hz, 6H), 1.04 (d, J=7.04 Hz, 3H).

Preparation I-4A-1e: 1-isopropyl-6-methyl-4,6-dihydrospiro[indazole-5,4'-piperidin]-7(1H)-one

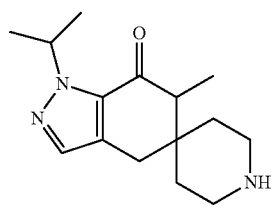

I-4A-1e

The title compound was prepared from Preparation I-4A-1d in an analogous fashion to Preparation I-1A-2f.

Preparation I-6A-1a: Benzyl 1-isopropyl-6,6-dimethyl-7-oxo-1,4,6,7-tetrahydrospiro [indazole-5,4'-piperidine]-1'-carboxylate

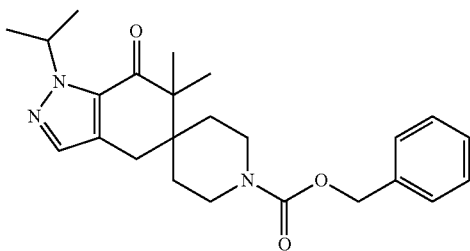

I-6A-1a

A solution of Preparation I-4A-1d (84 mg, 021 mmol) in 1 mL tetrahydrofuran was cooled to −70° C. and then treated with lithium bis(trimethylsilyl)amide (0.318 mL, 0.318 mmol) as a 1.0 M solution in tetrahydrofuran over ten minutes. Then 1,3-Dimethyl-3,4,5,6-tetrahydro-2(1H)pyrimidinone (0.2 mL) was added to the reaction. Stirring continued for ten minutes at −70° C., then iodomethane (152 mg. 1.06 mmol) was added to the reaction. The mixture was allowed to warm to room temperature where it was held for four hours. To the reaction was added saturated, aqueous ammonium chloride (1 mL), the mixture was then partitioned between water (2 mL) and ethyl acetate (10 mL). The layers were separated and the aqueous layer was extracted with ethyl acetate (5 mL). The organic layers were combined, dried over magnesium sulfate, filtered and then concentrated to give a clear, yellow oil. The oil was purified by silica gel chromatography using 10-40% ethyl acetate in heptane as eluent to afford the title compound as a clear oil (58 mg, 67%): +ESI MS (M+H) 410.3; $^1$H NMR (400 MHz, CDCl$_3$) δ ppm 7.28-7.44 (m, 5H), 7.27 (s, 1H), 5.40 (m, 1H), 5.13 (s, 2H), 3.85-4.24 (m, 2H), 2.86-3.11 (m, 2H), 1.58-1.79 (m, 2H), 1.56 (s, 2H), 1.46 (d, J=6.64 Hz, 6H), 1.19-1.40 (m, 2H), 1.15 (s, 6H).

Preparation I-6A-1b: 1-isopropyl-6,6-dimethyl-4,6-dihydrospiro[indazole-5,4'-piperidin]-7(1H)-one

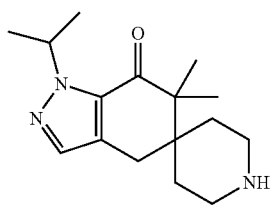

I-6A-1b

Preparation I-6A-1b was prepared from Preparation I-6A-1a in an analogous fashion to Preparation I-1A-2f.

Preparation I-13A-1a: tert-butyl 1-tert-butyl-7-oxo-1,4,6,7-tetrahydrospiro[indazole-5,4'-piperidine]-1'-carboxylate

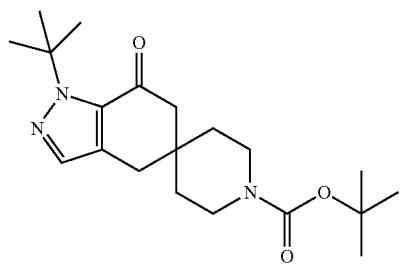

I-13A-1a

The hydrochloride salt of Preparation I-1A-2f (1040 mg, 3.492 mmol), di-tert-butyl dicarbonate (800 mg, 3.67 mmol) and triethylamine (730 mg, 7.2 mmol) were combined in dichloromethane (30 mL). The reaction solution was stirred at ambient temperature for 16 hours. To the reaction was added dichloromethane (20 mL). The reaction solution was washed with 1N aqueous hydrochloric acid (5 mL), water (5 mL), and saturated, aqueous sodium chloride (5 mL). The organic phase was dried over magnesium sulfate and concentrated to give I-13A-1a (1262 mg, 100%): −APCI MS (M−H) 360.3; $^1$H NMR (400 MHz, CDCl$_3$) δ ppm 7.30 (s, 1H), 3.29-3.56 (m, 4H), 2.77 (s, 2H), 2.56 (s, 2H), 1.67 (s, 9H), 1.48-1.56 (m, 4H), 1.46 (s, 9H).

Preparation I-13A-1b: tert-butyl 3-bromo-1-tert-butyl-7-oxo-1,4,6,7-tetrahydrospiro[indazole-5,4'-piperidine]-1'-carboxylate

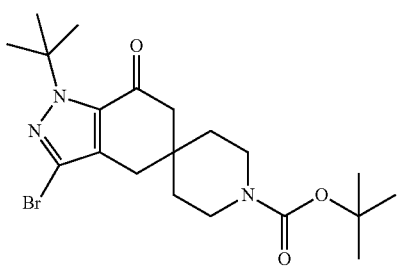

I-13A-1b

Preparation I-13A-1a (1090 mg, 3.015 mmol) and sodium acetate (1050 mg, 12.80 mmol) were combined in ethanol (40 mL) and water (10 mL). To this solution was added bromine (1870 mg, 11.7 mmol). The reaction was stirred at room temperature for 4 hours. To the reaction was added ethanol (40 mL). The reaction was stirred for 16 more hours. The reaction solution was poured in water (20 mL) and extracted twice with ethyl acetate (75 mL each). The combined organic extracts ware washed twice with aqueous, saturated sodium thiosulfate (25 mL each) and saturated, aqueous sodium chloride (25 mL). The organic phase was dried over magnesium sulfate and concentrated to a final volume of 20 mL to give a precipitate. The mixture was filtered and the solids collected to give the title compound as a solid (679 mg, 51%): +APCI MS (M+H-Boc) 342.1; $^1$H NMR (400 MHz, CDCl$_3$) 3 ppm 3.28-3.60 (m, 4H), 2.66 (s, 2H), 2.56 (s, 2H), 1.65 (s, 9H), 1.48-1.55 (m, 4H), 1.46 (s, 9H).

Preparation I-13A-1c: 3-bromo-1-tert-butyl-4,6-dihydrospiro[indazole-5,4'-piperidin]-7(1H)-one

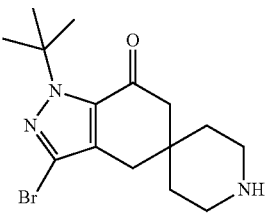

I-13A-1c

Preparation I-13A-1b (670 mg, 1.52 mmol) and 4 M hydrogen chloride in dioxane (8 mL) were combined and stirred for 2.5 hours. To the reaction was added diethyl ether (20 mL). A precipitate formed that was filtered and the solids collected to give I-13A-1c (573 mg, 97%): +APCI MS (M+H) 342.1; $^1$H NMR (400 MHz, CD$_3$OD) δ ppm 3.24 (t, J=5.96 Hz, 4H), 2.80 (s, 2H), 2.74 (s, 2H), 1.71-1.92 (m, 4H), 1.65 (s, 9H).

Example 1

Preparation of 1-isopropyl-1-(4-chloro-3-methylbenzoyl)-4,6-dihydrospiro[indazole-5,4'-piperidin]-7(1H)-one (1A-1)

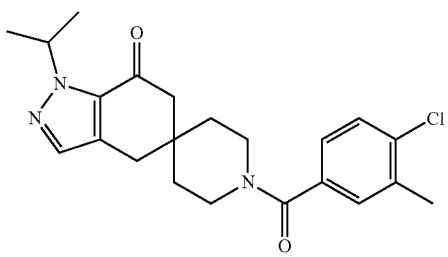

1A-1

4-chloro-3-methylbenzoic acid (253 mg, 1.48 mmol) was suspended in thionyl chloride (3000 mg, 30 mmol) and heated to reflux for 30 minutes. The solution was concentrated in vacuo in the presence of dichloromethane to give a residue. The residue was dissolved in 1 mL dichloromethane and added to a solution of diisopropyl ethylamine (890 mg, 6.9 mmol) and Preparation I-1A-1e (204 mg, 0.83 mmol) in 8 mL dichloromethane. The reaction was stirred for 10 minutes. The reaction was partitioned between dichloromethane and saturated, aqueous sodium bicarbonate. The organic phase as separated and then washed with saturated, aqueous sodium chloride. The organic layer was dried over sodium sulfate and concentrated in vacuo to give an oil. The oil was purified by flash chromatography using 15-100% ethyl acetate in heptane as eluent to afford the title compound as a white foam (153 mg, 46%): +ESI MS (M+H) 400.2; $^1$H NMR (400 MHz, CDCl$_3$) δ ppm 7.32-7.40 (m, 2H), 7.28 (s, 1H), 7.11-7.17 (m, 1H), 5.31-5.45 (m, 1H), 3.74 (br. s., 2H), 3.42 (br. s., 2H), 2.80 (s, 2H), 2.59 (s, 2H), 2.39 (s, 3H), 1.49-1.84 (m, 4H), 1.46 (d, J=6.63 Hz, 6H).

The compounds listed in Table 1 below were prepared using procedures analogous to those described above for the synthesis of Example 1, Compound 1A-1 using the appropriate starting materials which are available commercially, prepared using preparations well-known to those skilled in the art, or prepared in a manner analogous to routes described above for other intermediates.

TABLE 1

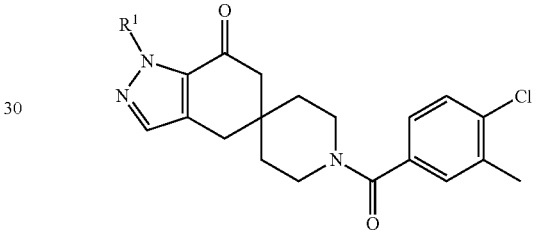

| Ex. | R$^1$ | Analytical Data |
|---|---|---|
| 1A-2 | C(CH$_3$)$_3$ | +ESI MS (M + H) 414.1; $^1$H NMR (400 MHz, CDCl$_3$) δ ppm 7.35 (d, J = 8.19 Hz, 1 H) 7.31 (s, 1 H) 7.28 (d, J = 2.15 Hz, 1 H) 7.14 (dd, J = 7.80, 1.95 Hz, 1 H) 3.19-4.01 (m, 4 H) 2.82 (s, 2 H) 2.61 (s, 2 H) 2.39 (s, 3 H) 1.66 (s, 9 H) 1.58 (s, 4 H) |
| 1A-3 | cyclobutyl | +ESI MS (M + H) 412.4; $^1$H NMR (400 MHz, CDCl$_3$) δ ppm 7.39 (s, 1 H) 7.31-7.37 (m, 1 H) 7.25 (s, 1 H) 7.12 (dd, J = 8.01, 1.76 Hz, 1 H) 5.58 (quin, J = 8.35 Hz, 1 H) 3.72 (br. s., 2 H) 3.38 (br. s., 2 H) 2.77 (s, 2 H) 2.56-2.68 (m, 2 H) 2.55 (s, 2 H) 2.38-2.46 (m, 2 H) 2.37 (s, 3 H) 1.74-1.93 (m, 2 H) 1.40-1.72 (m, 4 H) |
| 1A-4 | benzyl | +ESI MS (M + H) 448.4; $^1$H NMR (400 MHz, CDCl$_3$) δ ppm 7.39 (s, 1 H) 7.31-7.36 (m, 2 H) 7.21-7.29 (m, 5 H) 7.09-7.15 (m, 1 H) 5.65 (s, 2 H) 3.52-3.89 (m, 2 H) 3.15-3.52 (m, 2 H) 2.78 (s, 2 H) 2.55 (s, 2 H) 2.37 (s, 3 H) 1.41-1.75 (m, 4 H) |
| 1A-5 | ![tetrahydrofuranyl] | +ESI MS (M + H) 428.5; $^1$H NMR (400 MHz, CDCl$_3$) δ ppm 7.38 (s, 1 H) 7.34 (d, J = 8.00 Hz, 1 H) 7.25-7.27 (m, 1 H) 7.10-7.14 (m, 1 H) 5.73-5.82 (m, 1 H) 4.04 -4.19 (m, 2 H) 3.89-3.99 (m, 2 H) 3.72 (br. s., 2 H) 3.39 (br. s., 2 H) 2.79 (s, 2 H) 2.58 (s, 2 H) 2.38-2.47 (m, 2 H) 2.36 (s, 3 H) 1.58 (s, 4 H) |

Example 2

Preparation of 1-isopropyl-1'-(1H)-pyrazolo[3,4-b]pyridine-5-carbonyl)-4,6-dihydrospiro[indazole-5,4'-piperidin]-7(1H)-one (2A-1)

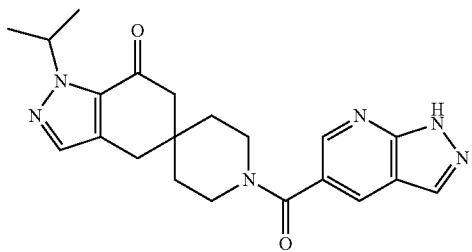

The hydrochloride salt of Preparation I-1A-1e (80 mg, 0.28 mmol), 1H-pyrazolo[3,4-b]pyridine-5-carboxylic acid (46 mg, 0.28 mmol), O-(azabenzotriazole-1-yl)-N,N,N',N'-tetramethyluronium hexafluorophosphate (107 mg, 0.28 mmol) and triethylamine (115 mg, 1.13 mmol) were combined in 3 mL of dimethylformamide and stirred at room temperature for 16 hours. The reaction was partitioned between 10 mL ethyl acetate and 10 mL saturated aqueous sodium bicarbonate. The organic phase was separated and then concentrated to give an oil. The oil was purified by flash chromatography using 50-100% ethyl acetate in heptane as eluent to afford the title compound as a solid (48 mg, 44%): +APCI MS (M+H) 393.2; $^1$H NMR (400 MHz, CDCl$_3$) δ ppm 11.08 (br. s., 1H), 8.67 (d, J=1.95 Hz. 1H), 8.22 (d. J=1.76 Hz, 1H), 8.16 (s, 1H), 7.40 (s, 1H), 5.32-5.46 (m, 1H), 3.24-4.13 (m, 4H), 2.84 (s, 2H), 2.63 (s, 2H), 1.66 (br. s., 4H), 1.47 (d, J=6.63 Hz, 6H).

The compounds listed in Table 2 below were prepared using procedures analogous to those described above for the synthesis of Compound 2A-1 using the appropriate starting materials which are available commercially, prepared using preparations well-known to those skilled in the art, or prepared in a manner analogous to routes described above for other intermediates. The compounds listed below were isolated initially as the free base and may be converted to their corresponding hydrochloride salt for testing.

TABLE 2

| Ex. | R$^1$ | R$^2$ | C(O)R$^4$ | Analytical Data |
|---|---|---|---|---|
| 2A-2 | (tetrahydrofuran-2-ylmethyl, via CH$_2$) | H | 4-Cl, 3-methylbenzoyl | +APCI MS (M + H) 442.2; $^1$H NMR (400 MHz, DMSO-d$_6$) δ ppm 7.42-7.49 (m, 2 H) 7.37 (d, J = 1.76 Hz, 1 H) 7.18-7.25 (m, 1 H) 4.51 (dd, J = 13.27, 7.22 Hz, 1 H) 4.32 (dd, J = 13.36, 5.37 Hz, 1 H) 4.07-4.17 (m, 1 H) 3.62-3.75 (m, 2 H) 3.53-3.62 (m, 2 H) 3.24-3.33 (m, 2 H) 2.80 (s, 2 H) 2.60 (s, 2 H) 2.34 (s, 3 H) 1.68-1.91 (m, 3 H) 1.37-1.66 (m, 5 H) |
| 2A-3 | CH(CH$_3$)CH$_2$OCH$_3$ | H | 4-Cl, 3-methylbenzoyl | +ESI MS (M + H) 430.1; $^1$H NMR (400 MHz, DMSO-d$_6$) δ ppm 7.41-7.51 (m, 2 H) 7.37 (d, J = 2.15 Hz, 1 H) 7.21 (dd, J = 7.90, 1.85 Hz, 1 H) 4.51 (dd, J = 13.27, 7.22 Hz, 1 H) 4.32 (dd, J = 13.46, 5.27 Hz, 1 H) 4.09-4.17 (m, 1 H) 3.62-3.74 (m, 2 H) 3.44-3.61 (m, 2 H) 3.31 (s, 3 H) 2.80 (s, 2 H) 2.59 (s, 2 H) 2.34 (s, 3 H) 1.67-1.90 (m, 2 H) 1.37-1.65 (m, 5 H) |
| 2A-4 | CH$_3$ | H | 4-Cl, 3-methylbenzoyl | +ESI (MS) 372.1; $^1$H NMR (400 MHz, CD$_3$OD) δ ppm 7.43 (d, J = 8.19 Hz, 1 H) 7.39 (s, 1 H) 7.34 (d, J = 1.56 Hz, 1 H) 7.22 (d, J =1.56 Hz, 1 H) 4.07 (s, 3 H) 3.56-3.95 (m, 2 H) 3.35-3.55 (m, 2 H) 2.87 (s, 2 H) 2.63 (d, J = 1.95 Hz, 2 H) 2.40 (s, 3 H) 1.41-1.83 (m, 4 H) |

TABLE 2-continued

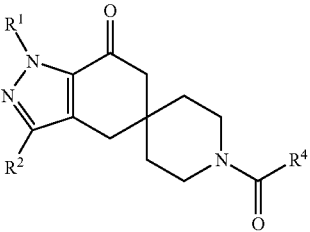

| Ex. | R¹ | R² | C(O)R⁴ | Analytical Data |
|---|---|---|---|---|
| 2A-5 | CH₂CH(CH₃)₂ | H | 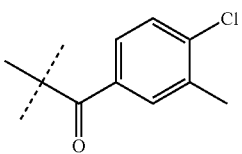 | +ESI (MS) 414.4; ¹H NMR (400 MHz, CDCl₃) δ ppm 7.30-7.43 (m, 2 H) 7.28 (s, 1 H) 7.14 (dd, J = 8.11, 2.05 Hz, 1 H) 4.31 (d, J = 7.43 Hz, 2 H) 3.16-3.99 (m, 4 H) 2.81 (s, 2 H) 2.58 (s, 2 H) 2.39 (s, 3 H) 2.07-2.28 (m, 1 H) 1.66 (s, 4 H) 0.87 (d, J = 6.84 Hz, 6 H) |
| 2A-6 | 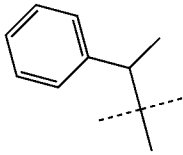 | H | 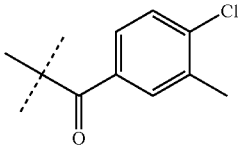 | +ESI (MS) 462.2; ¹H NMR (400 MHz, CDCl₃) δ ppm 7.40 (s, 1 H) 7.14-7.36 (m, 7 H) 7.10 (dd, J = 8.11, 1.86 Hz, 1 H) 6.42 (q, J = 7.04 Hz, 1 H) 3.10-3.97 (m, 4 H) 2.64-2.88 (m, 2 H) 2.42-2.63 (m, 2 H) 2.36 (s, 3 H) 1.86 (d, J = 7.04 Hz, 3 H) 1.61 (s, 4 H) |
| 2A-7 | CH₂CH₃ | H | 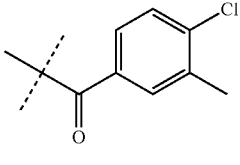 | +ESI (MS) 386.5 |
| 2A-8 | CH₂CH₂OCH₃ | H | 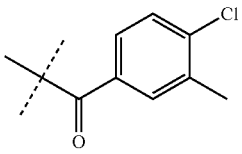 | +APCI MS (M + H) 416.2; ¹H NMR (400 MHz, CDCl₃) δ ppm 7.40 (s, 1 H) 7.36 (d, J = 8.19 Hz, 1 H) 7.28 (d, J = 1.76 Hz, 1 H) 7.14 (dd, J = 8.00, 1.76 Hz, 1 H) 4.69 (t, J = 5.56 Hz; 2 H) 3.75 (t, J = 5.56 Hz, 4 H) 3.33-3.54 (m, 2 H) 3.31 (s, 3 H) 2.81 (s, 2 H) 2.59 (s, 2 H) 2.39 (s, 3 H) 1.62 (s, 4 H) |
| 2A-9 | (CH₂)₂CH₃ | H | 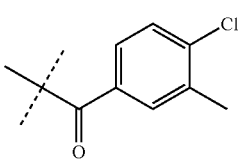 | +APCI MS (M + H) 400.2; ¹H NMR (400 MHz, CD₃OD) δ ppm 7.39-7.49 (m, 2 H) 7.33-7.36 (m, 1 H) 7.19-7.25 (m, 1 H) 4.43 (t, J = 7.02 Hz, 2 H) 3.76-3.95 (m, 1 H) 3.60-3.76 (m, 1 H) 3.36-3.54 (m, 2 H) 2.89 (s, 2 H) 2.64 (d, J = 1.95 Hz, 2 H) 2.40 (s, 3 H) 1.79 (sxt, J = 7.26 Hz, 2 H) 1.47-1.73 (m, 4 H) 0.85 (t, J = 7.41 Hz, 3 H) |
| 2A-10 | CH(CH₃)₂ | H | 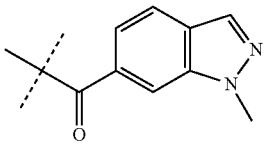 | +ESI MS (M + H) 406.5; ¹H NMR (400 MHz, CDCl₃) δ ppm 7.98 (d, J = 0.78 Hz, 1 H) 7.71 (d, J = 7.82 Hz, 1 H) 7.48 (d, J = 0.78 Hz, 1 H) 7.36 (s, 1 H) 7.07-7.13 (m, 1 H) 5.30-5.39 (m, 1 H) 4.07 (s, 3 H) 3.80 (br. s., 2 H) 3.42 (br. s., 2 H) 2.79 (s, 2 H) 2.58 (s, 2H) 1.69 (br. s., 2 H) 1.54 (br. s., 2 H) 1.43 (d, J = 6.64 Hz, 6 H) |

TABLE 2-continued

| Ex. | R¹ | R² | C(O)R⁴ | Analytical Data |
|---|---|---|---|---|
| 2A-11 | CH(CH₃)₂ | H | 1-methyl-1H-indazol-5-yl carbonyl | +ESI MS (M + H) 406.5; ¹H NMR (400 MHz, CDCl₃) δ ppm 8.00 (s, 1 H) 7.79 (S,1 H) 7.32-7.47 (m, 3 H) 5.30-5.41 (m, 1 H) 4.07 (s, 3 H) 3.61 (br. s., 4 H) 2.79 (s, 2 H) 2.58 (s, 2 H) 1.61 (br. s., 2 H) 1.53 (br. s., 2 H) 1.43 (d, J = 6.84 Hz, 6 H) |
| 2A-12 | CH(CH₃)₂ | H | 1H-benzimidazol-5-yl carbonyl | +ESI MS (M + H) 392.2; ¹H NMR (400 MHz, CDCl₃) δ ppm 7.99 (s, 1 H) 7.69 (s, 1 H) 7.58 (d, J = 7.61 Hz, 1 H) 7.39 (s, 1 H) 7.29 (dd, J = 8.19, 1.37 Hz, 1 H) 5.38 (quin, J = 6.63 Hz, 1 H) 3.35-3.97 (m, 4 H) 2.82 (d, J = 1.95 Hz, 2 H) 2.61 (s, 2 H) 1.50-1.82 (m, 4 H) 1.46 (d, J = 6.63 Hz, 6 H) |
| 2A-13 | CH(CH₃)₂ | H | 1-oxo-1,2-dihydroisoquinolin-7-yl carbonyl | +ESI (MS) 419.2; ¹H NMR (400 MHz, CDCl₃) δ ppm 9.59 (br. s., 1 H) 8.41 (d, J = 1.76 Hz, 1 H) 7.76 (dd, J = 8.19, 1.76 Hz, 1 H) 7.61 (d, J = 8.00 Hz, 1 H) 7.39 (s, 1 H) 7.15 (dd, J = 7.12, 5.76 Hz, 1 H) 6.56 (d, J =7 .41 Hz, 1 H) 5.38 (qd, J = 6.63, 6.44 Hz, 1 H) 3.64-4.02 (m, 2 H) 3.34-3.64 (m, 2 H) 2.82 (s, 2 H) 2.61 (s, 2 H) 1.52-1.91 (m, 4 H) 1.46 (d, J = 6.44 Hz, 6 H) |
| 2A-14 | CH(CH₃)₂ | H | 1-oxo-1,2-dihydroisoquinolin-6-yl carbonyl | +ESI (MS) 419.4; ¹H NMR (400 MHz, CDCl₃) δ ppm 8.44 (d, J = 8.19 Hz, 1 H) 7.60 (d, J = 1.37 Hz, 1 H) 7.47 (dd, J = 8.19, 1.56 Hz, 1 H) 7.39 (s, 1 H) 7.18 (ddd, J = 7.07, 1.90, 1.17 Hz, 1 H) 6.58 (d, J = 7.22 Hz, 1 H) 5.38 (quin, J = 6.63 Hz, 1 H) 3.66-3.96 (m, 2 H) 3.40 (br. s., 2 H) 2.82 (s, 2 H) 2.61 (s, 2 H) 1.72 (br. s., 2 H) 1.51-1.61 (m, 2H) 1.45 (s, 6 H) |
| 2A-15 | CH(CH₃)₂ | H | 4-amino-2-methylpyrimidin-5-yl carbonyl | +ESI (MS) 363.5; ¹H NMR (400 MHz, CD₃OD) δ ppm 8.05 (s, 1 H) 7.42 (s, 1 H) 5.24-5.58 (m, 1 H) 3.37-3.96 (m, 4 H) 2.87 (s, 2 H) 2.63 (s, 2 H) 2.43 (s, 3 H) 1.63 (br. s., 4 H) 1.42 (d, J = 6.64 Hz, 6 H) |
| 2A-16 | CH(CH₃)₂ | H | 7-chloro-1H-indazol-5-yl carbonyl | +ESI MS (M + H) 426.4; ¹H NMR (400 MHz, CDCl₃) δ ppm 10.57 (br. s., 1 H) 8.14 (s, 1 H) 7.72 (d, J = 1.17 Hz, 1 H) 7.45 (d, J = 1.17 Hz, 1 H) 7.37 (s, 1 H) 5.30-5.42 (m, 1 H) 3.59 (br. s., 4 H) 2.80 (s, 2 H) 2.59 (s, 2 H) 1.62 (br. s., 4 H) 1.44 (d, J = 6.63 Hz, 6 H) |

TABLE 2-continued

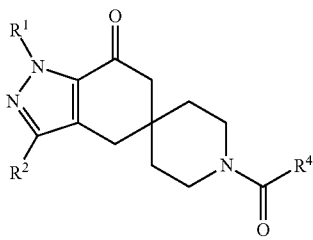

| Ex. | R¹ | R² | C(O)R⁴ | Analytical Data |
|---|---|---|---|---|
| 2A-17 | CH(CH₃)₂ | H | | +ESI MS (M + H) 382.5; ¹H NMR (400 MHz, CDCl₃) δ ppm 8.20 (dd, J = 2.34, 0.59 Hz, 1 H), 7.56 (dd, J = 8.58, 2.34 Hz, 1 H) 7.38 (s, 1 H) 6.39 (dd, J = 8.68, 0.68 Hz, 1H) 5.31-5.47 (m, 1 H), 4.83 (q, J = 5.14 Hz, 1 H), 3.51-3.69 (m, 4 H), 2.96 (d, J = 5.27 Hz, 3 H), 2.80 (s, 2 H) 2.59 (s, 2 H), 1.53-1.75 (m, 4 H) |
| 2A-18 | CH(CH₃)₂ | H | | +ESI MS (M + H) 410.5; ¹H NMR (400 MHz, CDCl₃) δ ppm 7.94 (s, 1 H) 7.35 (s, 1 H) 6.30 (s, 1 H) 5.30-5.40 (m, 1 H) 3.26-3.83 (br. m, 4 H) 3.06 (s, 6 H) 2.77 (s, 2 H) 2.55 (s, 2 H) 2.23 (s, 3 H) 1.56 (br. s., 4 H) 1.37-1.47 (m, 6 H) |
| 2A-19 | CH(CH₃)₂ | H | | +APCI MS (M + H) 392.2; ¹H NMR (400 MHz, DMSO-d₆), δ ppm 11.76 (br. s., 1 H), 8.43 (d, J = 1.76 Hz, 1 H) 7.95 (s, 1 H) 7.86 (t, J = 2.93 Hz, 1 H) 7.46 (s, 1 H) 6.65 (ddd, J = 2.98, 1.90, 0.78 Hz, 1 H) 5.27 (quin, J = 6.58 Hz, 1 H) 3.26-3.86 (m, 4 H) 2.82 (s, 2 H) 2.63 (s, 2 H) 1.41-1.66 (m, 4 H) |
| 2A-20 | CH(CH₃)₂ | H | | +ESI MS (M + H) 392.5; ¹H NMR (400 MHz, DMSO-d₆) δ ppm 12.05 (s, 1 H) 8.30 (dd, J = 4.69, 1.56 Hz, 1 H) 8.00 (dd, J = 7.82, 1.56 Hz, 1 H) 7.47 (s, 1 H) 7.03-7.16 (m,1 H) 6.71 (d, J = 2.15 Hz, 1 H) 5.28 (quin, J = 6.64 Hz, 1 H) 3.57-3.82 (m, 4 H) 2.83 (s, 2 H) 2.64 (s, 2 H) 1.52-1.61 (m, 4 H) 1.37 (d, J = 6.64 Hz, 6 H) |
| 2A-21 | C(CH₃)₃ | H | | +ESI MS (M + H) 420.5; ¹H NMR (400 MHz, CD₃OD) δ ppm 7.56 (d, J = 0.78 Hz, 1 H) 7.54 (d, J = 8.21 Hz, 1 H) 7.34 (s, 1 H) 7.27 (dd, J = 8.21, 1.56 Hz, 1 H) 3.88 (br. s., 1 H) 3.71 (br. s., 1 H) 3.45-3.58 (m, 2 H) 2.90 (s, 2 H) 2.66 (s, 2 H) 2.59 (s, 3 H) 1.65-1.81 (m, 2 H) 1.63 (s, 9 H) 1.51-1.60 (m, 2H) |
| 2A-22 | C(CH₃)₃ | H | | +ESI (MS) 433.5; ¹H NMR (400 MHz, CDCl₃) δ ppm 11.53 (br. s., 1 H) 8.39 (d, J = 8.21 Hz, 1 H) 7.55 (d, J = 1.17 Hz, 1 H) 7.34-7.48 (m, 1 H) 7.27 (s, 1 H) 7.11-7.22 (m, 1 H) 6.52 (d, J = 7.23 Hz, 1 H) 3.58-3.98 (m, 2 H) 3.19-3.53 (m, 2 H) 2.79 (s, 2 H) 2.59 (s, 2 H) 1.63-1.79 (m, 2 H) 1.61 (s, 9 H) 1.39-1.55 (m, 2 H) |

TABLE 2-continued

| Ex. | R¹ | R² | C(O)R⁴ | Analytical Data |
|---|---|---|---|---|
| 2A-23 | C(CH₃)₃ | H | 5-acyl-1H-pyrrolo[2,3-b]pyridine | +ESI (MS) 406.5; ¹H NMR (400 MHz, CDCl₃) δ ppm 10.95 (br. s., 1 H) 8.44 (d, J = 1.95 Hz, 1 H) 8.04 (d, J = 1.95 Hz, 1 H) 7.38-7.50 (m, 1 H) 7.31 (s, 1 H) 6.55 (dd, J = 3.52, 1.95 Hz, 1 H) 3.22-4.13 (m, 4 H) 2.83 (s, 2 H) 2.63 (s, 2 H) 1.65 (s, 13 H) |
| 2A-24 | C(CH₃)₃ | H | 6-acyl-1H-pyrrolo[3,2-b]pyridine | +ESI (MS) 406.5; ¹H NMR (400 MHz, CDCl₃) δ ppm 10.05 (br. s.. 1 H) 8.49 (d, J = 1.76 Hz, 1 H) 7.68 (d, J = 0.78 Hz, 1 H) 7.49 (t, J = 3.02 Hz, 1 H) 7.32 (s, 1 H) 6.70 (ddd, J = 3.07, 2.00, 0.78 Hz, 1 H) 3.29-4.03 (m, 4 H) 2.83 (s, 2 H) 2.62 (s, 2 H) 1.66 (s, 13 H) |
| 2A-25 | C(CH₃)₃ | H | 7-chloro-5-acyl-1H-indazole | +APCI (M + H) 440.2; ¹H NMR (400 MHz, CDCl₃) δ ppm 8.16 (s, 1 H) 7.74 (d, J = 1.17 Hz, 1 H) 7.48 (d, J = 1.17 Hz, 1 H) 7.32 (s, 1 H) 3.64 (br. s., 4 H) 2.84 (s, 2 H) 2.64 (s, 2 H) 1.67 (br. s., 13 H) |
| 2A-26 | CH(CH₃)₂ | H | 5-acyl-1H-pyrazolo[3,4-b]pyridine | +APCI (M + H) 392.2; ¹H NMR (400 MHz, CD₃OD) δ ppm 1.40 (d, J = 6.63 Hz, 6 H), 1.53-1.74 (m, 4 H), 2.64 (s, 2 H), 2.88 (s, 2 H) 3.48-3.91 (m, 4 H), 5.32-5.41 (m, 1 H), 6.56 (d, J = 3.51 Hz, 1 H), 7.41 (s, 1 H) 7.46 (d, J = 3.51 Hz, 1 H), 8.07 (d, J = 1.95 Hz, 1 H), 8.27 (d, J = 1.76 Hz, 1 H) |
| 2A-27 | CH(CH₃)₂ | H | 5-acyl-1,3-dihydro-2H-indol-2-one | +APCI (M + H) 407.2; ¹H NMR (400 MHz, CDCl₃) δ ppm 1.43 (d, J = 6.64 Hz, 6 H), 2.57 (s, 2 H), 2.78 (s, 2 H), 3.47 (d, J = 5.28 Hz, 1 H), 3.53 (s, 2 H), 5.31-5.40 (m, 1 H), 6.84 (d, J = 8.01 Hz, 2 H), 7.28 (d, J = 8.40 Hz, 1 H), 7.36 (s, 1 H), 8.00 (s, 1 H) |
| 2A-28 | C(CH₃)₃ | H | 5-acyl-1H-indazole | +APCI (M + H) 406.3; ¹H NMR (400 MHz, CDCl₃) δ ppm 1.54-1.59 (m, 4 H), 1.61-1.66 (m, 9 H), 2.61 (s, 2 H), 2.81 (s, 2 H), 3.46 (m, 4 H), 7.29 (s, 1 H), 7.43 (dt, J = 8.60, 1.37 Hz, 1 H), 7.49 (d, J = 8.60 Hz, 1 H), 7.82 (s, 1 H), 8.08-8.12 (m, 1 H) |
| 2A-29 | C(CH₃)₃ | H | 5-acyl-1,3-dihydro-2H-benzimidazol-2-one | +ESI (M + H) 422.2; ¹H NMR (400 MHz, CDCl₃) δ ppm 1.58 (s, 4 H) 1.63 (s, 9 H), 2.60 (s, 2 H), 2.80 (s, 2 H), 3.30-3.92 (m, 4 H), 6.98 (d, J = 7.82 Hz, 1 H), 7.06 (dt, J = 8.01, 1.37 Hz, 1 H), 7.08-7.12 (m, 1 H), 7.29 (s, 1 H) |

TABLE 2-continued

| Ex. | R¹ | R² | C(O)R⁴ | Analytical Data |
|---|---|---|---|---|
| 2A-30 | C(CH₃)₃ | H | 5-acyl-oxindole | +ESI MS (M + H) 421.5; ¹H NMR (400 MHz, CDCl₃) δ ppm 7.96 (brs, 1 H) 7.32 (s, 1 H) 7.31(d, J = 0.87 Hz, 1 H) 7.28 (dd, J = 8.00, 1.78 Hz, 1 H) 6.92 (d, J = 8.00 Hz, 1 H) 3.55 (s, 2 H) 3.29 (m(5), J = 1.67 Hz, 2 H) 2.98 (d, J = 0.78 Hz, 1 H) 2.88 (s, 2 H) 2.85 (d., J = 0.78 Hz, 1 H), 2.64 (s, 2 H), 1.64 (s, 9 H), 1.56 (brm, 2 H) |
| 2A-31 | C(CH₃)₃ | H | 7-acyl-isoquinolinone | +ESI MS (M + H) 433.5; ¹H NMR (400 MHz, CD₃OD) δ ppm 8.33 (s, 1 H) 7.75 (s, 2 H) 7.34 (s, 1 H) 7.24 (d, J = 7.23 Hz, 1 H) 6.71 (d, J = 7.04 Hz, 1 H) 3.90 (br. s., 1 H) 3.83-3.95 (m, 1 H) 3.70 (br. s., 1 H) 3.49 (br. s., 2 H) 2.91 (s, 2 H) 2.67 (br. s., 2 H) 1.66-1.72 (m, 2 H) 1.63 (s, 9 H) 1.53-1.60 (m, 2 H) |
| 2A-32 | C(CH₃)₃ | H | 6-acyl-benzimidazole | +ESI (M + H) 406.2; ¹H NMR (400 MHz, CDCl₃) δ ppm 1.62 (br. s., 13 H), 2.59 (br. s., 2 H), 2.80 (br. s., 2 H), 3.30-3.95 (m, 4 H), 7.19 (d, J = 8.00 Hz, 1 H), 7.28 (s, 1 H), 7.45 (d, J = 7.61 Hz, 1 H), 7.59 (br. s., 1 H), 7.85 (s, 1 H) |
| 2A-33 | CH(CH₃)₂ | H | 6-acyl-benzimidazolone | +ESI MS (M + H) 408.5; ¹H NMR (400 MHz, DMSO-d₆) δ ppm 10.77 (s, 1 H) 10.70 (s, 1 H) 7.45 (s,1 H) 6.86-7.02 (m, 3 H) 5.27 (quin, J = 6.60 Hz, 1 H) 3.45 (br. s., 4 H) 3.07-3.14 (m, 1 H) 2.79 (s, 2 H) 2.60 (s, 2 H) 1.48 (br. s., 4 H) 1.35 (d, J = 6.64 Hz, 6 H) |
| 2A-34 | C(CH₃)₃ | H | 7-acyl-dihydroquinolinone | +ESI MS (M + H) 435.5; ¹H NMR (400 MHz, DMSO-d₆) δ ppm 10.15 (s, 1 H) 7.39 (s, 1 H) 7.20 (d, J = 7.62 Hz, 1 H) 6.91 (dd, J = 7.62, 1.56 Hz, 1 H) 6.85 (d, J = 1.56 Hz, 1 H) 3.69 ( br. s., 1 H) 3.48 (br. s., 1 H) 3.05-3.17 (m, 1 H) 2.89 (t, J = 7.62 Hz, 2 H) 2.82 (s, 2 H) 2.62 (s, 2 H) 2.45 (dd, J = 8.70, 6.55 Hz, 2 H) 1.57 (s, 9 H) 1.46 (br. s., 4 H); ESI+ MS (M + H) 435.5. |
| 2A-35 | CH(CH₃)₂ | H | 6-acyl-dihydroisoquinolinone | +ESI MS (M + H) 421.5; ¹H NMR (400 MHz, DMSO-d₆) δ ppm 10.15 (s, 1 H) 7.45 (s, 1 H) 7.20 (d, J = 7.61 Hz, 1 H) 6.91 (dd, J = 7.51, 1.66 Hz, 1 H) 6.85 (d, J = 1.56 Hz, 1 H) 5.27 (quin, J = 6.58 Hz, 1 H) 3.65 (br. s., 1 H) 3.53 (br. s., 1 H) 2.89 (t, J = 7.61 Hz, 2 H) 2.79 (br. s., 2 H) 2.60 (s, 2 H) 2.45 (dd, J = 8.78, 6.44 Hz, 3 H) 1.48 (br. s., 4 H) 1.36 (d, J = 6.63 Hz, 6 H) |

TABLE 2-continued

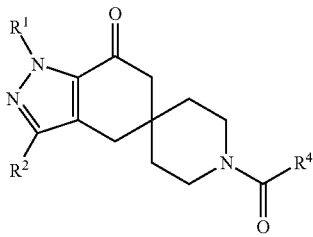

| Ex. | R¹ | R² | C(O)R⁴ | Analytical Data |
|---|---|---|---|---|
| 2A-36 | CH(CH₃)₂ | H | 4-fluoro-1H-benzimidazol-6-yl carbonyl | +ESI MS (M + H) 410.5; ¹H NMR (400 MHz, CDCl₃) δ ppm 7.94 (s, 1 H) 7.40 (s, 1 H) 7.28-7.38 (m, 1 H) 7.00 (d, J = 10.36 Hz, 1 H) 5.38 (quin, J = 6.64 Hz, 1 H) 3.26-4.02 (m, 4 H) 2.83 (s, 2 H) 2.61 (s, 2H) 1.70 (br. s., 4 H) 1.46 (d, J = 6.45 Hz, 6 H) |
| 2A-37 | CH(CH₃)₂ | H | 7-fluoro-1H-indazol-5-yl carbonyl | +ESI (M = 1) 410.5; ¹H NMR (400 MHz, CDCl₃) δ ppm 9.18 (s, 1 H) 8.56 (d, J = 6.24 Hz, 1 H) 8.15 (s, 1 H) 7.69 (d, J = 6.44 Hz, 1 H) 7.40 (s, 1 H) 5.37 (dt, J = 13.27, 6.63 Hz, 1 H) 3.54-3.88 (m, 2 H) 3.17 (qd, J = 7.28, 3.90 Hz, 2 H) 2.86 (s, 2 H) 2.62 (s, 2 H) 1.57-1.83 (m, 4 H) |
| 2A-38 | CH(CH₃)₂ | H | 2-amino-1,6-naphthyridin-3-yl carbonyl | +ESI MS (M + H) 419.5; 1H NMR (400 MHz, CDCl₃) δ ppm 9.18 (s, 1 H) 8.56 (d, J = 6.24 Hz, 1 H) 8.15 (s, 1 H) 7.69 (d, J = 6.44 Hz, 1 H) 7.40 (s, 1 H) 5.37 (m, 6.63 Hz, 1 H) 3.54-3.88 (m, 2 H) 3.17 (qd, J = 7.28, 3.90 Hz, 2 H) 2.86 (s, 2 H) 2.62 (s, 2 H) 1.57-1.83 (m, 4 H) |
| 2A-39 | C(CH₃)₃ | H | 3-aminoquinoxalin-2-yl carbonyl | +ESI MS (M + H) 433.5; ¹H NMR (400 MHz, CDCl₃) δ ppm 7.80-7.88 (m, 1 H) 7.59-7.71 (m, 2 H) 7.40-7.49 (m, 1 H) 7.33 (s, 1 H) 5.78 (br. s., 2 H) 3.87-3.98 (m, 1 H), 3.76-3.86 (m, 1 H) 3.60-3.75 (m, 2 H) 2.87 (s, 2 H), 2.66 (s, 2 H) 1.68-1.79 (m, 4 H) |
| 2A-40 | CH(CH₃)₂ | H | 7-aminopyrazolo[1,5-a]pyrimidin-6-yl carbonyl | +ESI MS (M + H) 408.0; ¹H NMR (400 MHz, CD₃OD) δ ppm 8.15 (s, 1 H) 8.09 (s, 1 H) 7.42 (s, 1 H) 6.45 (s, 1 H) 5.26-5.45 (m, 1 H) 3.58-3.77 (m, 4 H) 2.88 (s, 2 H) 2.65 (s, 2 H) 1.61-1.67 (m, 4 H) 1.42 (d, J = 6.64 Hz, 6 H) |
| 2A-41 | C(CH₃)₃ | H | 1H-pyrazolo[3,4-b]pyridin-5-yl carbonyl | ESI + MS (M + H) 407.5; ¹H NMR (400 MHz, DMSO-d₆) δ ppm 13.84 (s, 1 H) 8.55 (d, J = 1.95 Hz, 1 H) 8.30 (d, J = 1.37 Hz, 1 H) 8.21 (d, J = 1.17 Hz, 1 H) 7.40 (s, 1 H) 3.75 (br. s., 1 H) 3.44 (br. s., 4 H) 3.05-3.17 (m, 3 H) 2.84 (s, 2 H) 2.66 (s, 2 H) 1.57 (s, 9 H) 1.50 (br. s., 4H) |
| 2A-42 | 3-methyloxetan-3-yl | H | 2-methyl-1H-benzimidazol-6-yl carbonyl | +ESI MS (M + H) 420.2; ¹H NMR (400 MHz, CD₃OD) δ ppm 1.54 (br. s., 4 H), 2.56 (s, 3 H), 2.62 (s, 2 H), 2.89 (s, 2 H), 3.38-3.90 (m, 4 H), 4.95-5.04 (m, 4 H), 6.10- 6.13 (m, 1 H), 7.24 (dd, J = 8.29, 1.46 Hz, 1 H), 7.52 (d, J = 8.19 Hz, 1 H), 7.54 (s, 1 H) 8.49 (s, 1 H) |

TABLE 2-continued

| Ex. | R¹ | R² | C(O)R⁴ | Analytical Data |
|---|---|---|---|---|
| 2A-43 | C(CH₃)₃ | H | pyrazolo[1,5-a]pyrimidine with NH₂ | ESI + MS (M + H) 422.5; ¹H NMR (400 MHz, DMSO-d₆) δ ppm 8.15 (d, J = 2.15 Hz, 1 H) 8.10 (s, 1H) 7.85 (s, 2 H) 7.40 (s, 1 H) 6.46 (d, J = 2.35 Hz, 1 H) 3.42-3.65 (m, 4 H) 2.82 (s, 2 H) 2.63 (s, 2 H) 1.58 (s, 9 H) 1.48-1.55 (m, 4 H) |
| 2A-44 | C(CH₃)₃ | H | 7-fluoro-1H-indazol-5-yl | +ESI MS (M + H) 424.2; ¹H NMR (400 MHz, CDCl₃) δ ppm 8.15 (d, J = 3.32 Hz, 1 H) 7.62 (d, J = 0.98 Hz, 1 H) 7.32 (s, 1 H) 7.19 (dd, J = 10.75, 0.98 Hz, 1 H) 3.64 (br. s., 4 H) 2.84 (s, 2 H) 2.64 (s, 2 H) 1.66 (s, 4 H) 1.59 (s, 9 H) |
| 2A-45 | C(CH₃)₃ | H | 1-methyl-2-oxo-2,3-dihydro-1H-benzimidazol-5-yl | +ESI MS (M + H) 436.5; ¹H NMR (400 MHz, CDCl₃) δ ppm 10.10 (s, 1 H) 7.27 (s, 1 H) 7.14 (s, 1 H) 7.12 (dd, J = 7.91, 1.27 Hz, 1 H) 6.92 (d, J = 8.01 Hz, 1 H) 3.64 (br. s., 4 H) 3.39 (s, 3 H) 2.78 (s, 2 H) 2.56 (s, 2H) 1.62 (s, 9 H) 1.55 (br. s., 4 H) |
| 2A-46 | CH(CH₃)₂ | H | 1-methyl-2-oxo-2,3-dihydro-1H-benzimidazol-5-yl | +ESI MS (M + H) 422.5; ¹H NMR (400 MHz, CDCl₃) δ ppm 9.82 (s,1 H) 7.36 (s, 1 H) 7.15 (s, 1 H) 7.13 (dd, 1 H) 6.93 (d, J = 8.01 Hz, 1 H) 5.35 (m, 1 H) 3.58 (br. s., 4 H) 3.40 (s, 3 H) 2.78 (s, 2 H) 2.57 (s, 2 H) 1.58 (br. s., 4 H) 1.43 (d, J = 6.64 Hz, 6 H) |
| 2A-47 | CH(CH₃)₂ | H | 4-chloro-1H-benzimidazol-6-yl | +ESI MS (M + H) 426.4; ¹H NMR (400 MHz, CD₃OD) δ ppm 8.30 (s, 1 H) 7.58 (br. s., 1 H) 7.38 (s, 1 H) 7.34 (s, 1H) 5.34 (m, 1 H) 3.83 (br. s., 1 H) 3.65 (br. s., 1 H) 3.46 (br. s., 2 H) 2.85 (s, 2 H) 2.61 (s, 2 H) 1.43-1.73 (m, 4 H) 1.38 (d, J = 6.63 Hz, 6 H) |
| 2A-48 | C(CH₃)₃ | H | 4-chloro-1H-benzimidazol-6-yl | +ES1 MS (M + H) 440.4; ¹H NMR (400 MHz, CD₃OD) δ ppm 8.30 (s, 1 H) 7.59 (br. s., 1 H) 7.34 (s, 1 H) 7.30 (s, 1 H) 3.81 (br. s., 1 H) 3.65 (br. s., 1 H) 3.47 (br. s., 2 H) 2.86 (s, 2 H) 2.62 (s, 2 H) 1.62-1.75 (m, 2 H) 1.59 (s, 9 H) 1.49-1.56 (m, 2 H) |
| 2A-49 | C(CH₃)₃ | H | 3-methyl-2-oxo-2,3-dihydro-1H-benzimidazol-5-yl | +ESI MS (M + H) 436.5; ¹H NMR (400 MHz, CDCl₃) δ ppm 8.36 (s, 1 H) 7.29 (s, 1 H) 7.06-7.10 (m, 2 H) 7.00 (d, 1 H) 3.57 (br. s., 4 H) 3.40 (s, 3 H) 2.80 (s, 2 H) 2.60 (s, 2 H) 1.63 (s, 9 H) 1.58 (br. s., 4 H) |

TABLE 2-continued

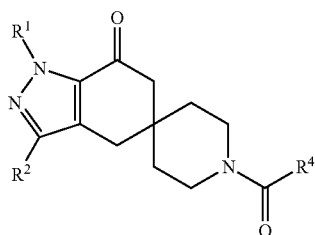

| Ex. | R¹ | R² | C(O)R⁴ | Analytical Data |
|---|---|---|---|---|
| 2A-50 | CH(CH₃)₂ | H | 5-carbonyl-1-methyl-2-oxo-2,3-dihydro-1H-benzimidazole | +ESI MS (M + H) 422.5; ¹H NMR (400 MHz, CDCl₃) δ ppm 9.55 (br. s., 1 H) 7.36 (s, 1 H) 7.00-7.10 (m, 3 H) 5.35 (quin, J = 6.55 Hz, 1 H) 3.58 (br. s., 4 H) 3.41 (s, 3 H) 2.79 (s, 2 H) 2.58 (s, 2 H) 1.59 (br. s., 4 H) 1.43 (d, J = 6.45 Hz, 6 H) |
| 2A-51 | C(CH₃)₃ | H | 4-fluoro-1H-benzimidazole-6-carbonyl | +ESI MS(M + H) 424.2; ¹H NMR (400 MHz, CDCl₃) δ ppm 7.99 (s, 1 H) 7.39 (br. s., 1 H) 7.30 (s, 1 H) 7.01 (d, J = 12.12 Hz, 1 H) 3.41-3.94 (m, 4 H) 2.83 (s, 1 H) 2.82 (s, 2 H) 2.61 (s, 2 H) 1.47-1.78 (m, 13 H) |
| 2A-52 | CH(CH₃)₂ | H | 4-chloro-2-methyl-1H-benzimidazole-6-carbonyl | +ESI MS (M + H) 440.4; ¹H NMR (400 MHz, CD₃OD) δ ppm 7.43-7.55 (m, 1 H) 7.42 (s, 1 H) 7.30 (s, 1 H) 5.30-5.43 (m, 1 H) 3.86 (br. s., 1 H) 3.63 (br. s., 1 H) 3.51 (br. s., 2 H) 2.89 (s, 2 H) 2.65 (s, 2 H) 2.61 (s, 3 H) 1.52-1.73 (m, 4 H) 1.42 (d, J = 6.64 Hz, 6 H) |
| 2A-53 | C(CH₃)₃ | H | 4-chloro-2-methyl-1H-benzimidazole-6-carbonyl | +ESI MS (M + H) 454.4; ¹H NMR (400 MHz, CD₃OD) δ ppm 7.49 (s, 1 H) 7.34 (s, 1 H) 7.30 (d, J = 1.37 Hz, 1 H) 3.40-3.97 (m, 4 H) 2.90 (s, 2 H) 2.66 (s, 2 H) 2.61 (s, 3 H) 1.54-1.71 (m, 13 H) |
| 2A-54 | CH(CH₃)₂ | H | 4-fluoro-2-methyl-1H-benzimidazole-6-carbonyl | +ESI MS (M + H) 424.4; ¹H NMR (400 MHz, CD₃OD) δ ppm 7.42 (s, 1 H) 7.36 (br. s., 1 H) 7.03 (d, J = 10.36 Hz, 1 H) 5.29-5.45 (m, 1 H) 3.38-4.07 (m, 4 H) 2.88 (s, 2 H) 2.64 (br. s., 2 H) 2.59 (s, 3 H) 1.48-1.82 (m, 4 H) 1.42 (d, J = 6.64 Hz, 6 H) |
| 2A-55 | C(CH₃)₃ | H | 4-fluoro-2-methyl-1H-benzimidazole-6-carbonyl | +ESI MS (M + H) 438.3; ¹HNMR (400 MHz, CD₃OD) δ ppm 7.35 (s, 2 H) 7.05(d, J = 10.36 Hz, 1 H) 3.38-4.10 (m, 4 H) 2.92 (s, 2 H) 2.68 (s, 2 H) 2.61 (s, 3 H) 1.65 (s, 13 H) |

TABLE 2-continued

| Ex. | R¹ | R² | C(O)R⁴ | Analytical Data |
|---|---|---|---|---|
| 2A-56 | C(CH₃)₃ | H | 4-chloro-benzimidazolone acyl | +ESI MS (M + H) 456.4; ¹H NMR (400 MHz, DMSO-d₆) δ ppm 7.39 (s, 1 H), 6.97 (s, 1 H) 6.84 (s, 1 H), 3.03-3.76 (m, 4 H) 2.82 (s, 2 H) 2.62 (s, 2 H) 1.58 (s, 9 H) |
| 2A-57 | CH(CH₃)₂ | H | 4-chloro-benzimidazolone acyl | +APCI MS (M + H) 442.2; ¹H NMR (400 MHz. CDCl₃) δ ppm 7.38 (s,1 H) 7.07-7.26 (m, 1 H) 7.03 (br. s., 1 H) 5.31-5.45 (m, 1 H) 3.25-3.92 (m, 4 H) 2.80 (s, 2H), 2.60 (s, 2 H) 1.50-1.77 (m, 4 H) |
| 2A-58 | CH(CH₃)₂ | H | 4-amino-1-methyl-pyrazolo[3,4-b]pyridine acyl | ESI + MS (M + H) 422.5; ¹H NMR (400 MHz, DMSO-d₆) δ ppm 8.18 (s, 1 H) 7.98 (s, 1 H) 7.46 (s, 1 H) 6.98 (br. s., 2 H) 5.27 (quin, J = 6.63 Hz, 1 H) 3.90 (s, 3 H) 3.48 (br s., 4 H) 2.79 (s, 2 H) 2.60 (s, 2 H) 1.46-1.56 (m, 4 H) 1.35 (d, J = 6.7 Hz, 6 H) |
| 2A-59 | C(CH₃)₃ | H | 4-amino-1-methyl-pyrazolo[3,4-b]pyridine acyl | ESI + MS (M + H) 436.5; ¹H NMR (400 MHz, DMSO-d₆) δ ppm 8.18 (s, 1 H) 7.98 (s, 1 H) 7.40 (s, 1 H) 6.98 (br. s., 2 H) 3.90 (s, 3 H) 3.38-3.62 (m, 4 H) 2.81 (s, 2 H) 2.62 (s, 2 H) 1.58 (s, 9 H) 1.45-1.52 (m, 4 H) |
| 2A-60 | CH(CH₃)₂ | H | 2-(3-methyl-1,2,4-oxadiazol-5-yl)pyridine-4-acyl | ESI + MS (M + H) 435.5; ¹HNMR (400 MHz, CD₃OD) δ 8.64 (d, J = 5.2 Hz, 1H), 3.05 (s, 1H), 7.46 (d, J = 4.8 Hz, 1H), 7.23 (s, 1H), 5.17 (m, 1H), 3.69 (m, 1H), 3.55 (m, 1H), 3.22 (m, 1H), 3.05 (m, 1H), 2.70 (m, 2H), 2.45 (s, 2H), 2.29 (s, 3H), 1.51 (m, 2H), 1.39 (m, 2H), 1.20 (m, 6H) |
| 2A-61 | CH(CH₃)₂ | H | quinoxaline-2-acyl | ESI + MS (M + Na) 426.4; ¹HNMR (400 MHz, CD₃OD) δ 9.09 (s, 1H), 8.13 (m, 2H), 7.93 (m, 2H), 7.46 (s, 1H), 5.38 (m, 1H), 3.97 (m, 1H), 3.82 (m, 1H), 3.68 (m, 2H), 2.95 (s, 2H), 2.70 (s, 2H), 1.70-1.80 (m, 4H), 1.43 (m, 6H) |
| 2A-62 | CH(CH₃)₂ | H | 6-acetamido-pyridine-2-acyl | ESI +MS (M + H) 410.6; ¹HNMR (400 MHz, CD₃OD) δ 9.16 (d, J = 8.4 Hz, 1H), 7.84 (t, 1H), 7.43 (s, 1H), 7.25 (d, J = 7.6 Hz, 1H), 5.36 (m, 1H), 3.83 (m, 1H), 3.66 (m, 1H), 3.48 (m, 2H), 2.89 (s, 2H), 2.65 (s, 2H), 2.16 (s, 3H), 1.71-1.62 (m, 4H) 1.42 (m, 6H) |

TABLE 2-continued

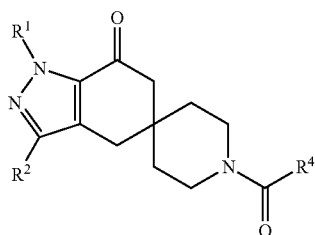

| Ex. | R¹ | R² | C(O)R⁴ | Analytical Data |
|---|---|---|---|---|
| 2A-63 | CH(CH₃)₂ | H | (2,6-naphthyridin-2-yl)carbonyl | ESI + MS (M + H) 404.3; ¹HNMR (400 MHz, CD₃OD) δ 9.43 (s, 1H), 8.78 (d, J = 6 Hz, 1H), 8.72 (d, J = 8.8 Hz, 1H), 8.01 (d, J = 6 Hz, 1H), 7.85 (d, J = 8.4 Hz, 1H), 7.46 (s, 1H), 5.39 (m, 1H), 3.96 (m, 1H), 3.81 (m, 1H), 3.49 (m, 2H), 2.94 (s, 2H), 2.69 (s, 2H), 1.78-1.65 (m, 4H), 1.42 (m, 6H) |
| 2A-64 | CH(CH₃)₂ | H | (1H-pyrrolo[3,2-c]pyridin-2-yl)carbonyl | ESI + MS (M + H) 392.4; ¹HNMR (400 MHz, CD₃OD) δ 8.89 (s, 1H), 8.18 (d, J = 6 Hz, 1H), 7.85 (d, J = 6 Hz, 1H), 8.01 (d, J = 6 Hz, 1H), 7.46 (s, 1H), 6.99 (s, 1H), 5.39 (m, 1H), 3.80-3.89 (m, 2H), 3.22 (m, 1H), 2.94 (m, 2H), 2.68 (m, 2H), 1.71-1.83 (m, 4H), 1.44 (d, J = 6.8 Hz, 6H) |
| 2A-65 | CH(CH₃)₂ | H | (4-chloro-1H-indazol-6-yl)carbonyl | ESI + MS (M + H) 426.2; ¹HNMR (400 MHz, CD₃OD) δ 8.18 (s, 1H), 7.57 (s, 1H), 7.45 (s, 1H), 7.23 (s, 1H), 5.37 (m, 1H), 3.90 (m, 1H), 3.75 (m, 1H), 3.49 (m, 1H), 3.22 (m, 1H), 2.92 (s, 2H), 2.68 (s, 2H), 1.59-1.81 (m, 4H), 1.30 (m, 6H) |
| 2A-66 | CH(CH₃)₂ | H | (2-morpholinopyrimidin-5-yl)carbonyl | ESI + MS (M + H) 439.5; ¹HNMR (400 MHz, CD₃OD) δ 8.47 (s, 2H), 7.45 (m, 1H), 5.39 (m, 1H), 3.65-3.88 (m, 10 H), 3.15-3.25 (m, 2H), 2.91 (s, 2H), 2.67 (s, 2H), 1.65-1.80 (m, 4H), 1.44 (d, J = 6.8 Hz, 6H) |
| 2A-67 | CH(CH₃)₂ | H | (1H-imidazo[1,2-b]pyrazol-2-yl)carbonyl | ESI + MS (M + H) 381.7; ¹HNMR (400 MHz, CD₃OD) δ 7.38 (s, 1H), 7.34 (s, 1H), 7.10 (s, 1H), 5.97 (s, 1H), 5.31 (m, 1 H), 3.91 (m, 1H), 3.82 (m, 2H), 3.65 (m, 1H), 2.84 (s, 2H), 2.59 (s, 2H), 1.58 (m, 4H), 1.37 (d, J = 6.8 Hz, 6H) |
| 2A-68 | CH(CH₃)₂ | H | (1H-indazol-6-yl)carbonyl | ESI + MS (M + H) 392.5; ¹HNMR (400 MHz, CD₃OD) δ 8.16 (s, 1H), 7.92 (s, 1H), 7.62 (d, J = 8.8 Hz, 1H) 7.46 (d, J = 8.8 Hz, 1H), 7.45 (s, 1H), 5.39 (m, 1 H), 3.51-3.99 (m, 4H), 2.92 (s, 2H), 2.68 (s, 2H), 1.61-1.70 (m, 4H), 1.43 (d, J = 6.4 Hz, 6H) |

TABLE 2-continued

| Ex. | R¹ | R² | C(O)R⁴ | Analytical Data |
|---|---|---|---|---|
| 2A-69 | CH(CH₃)₂ | H | (5-hydroxyquinolin-6-yl pivaloyl) | ESI + MS (M + H) 419.5; ¹HNMR (400 MHz, CD₃OD) δ 8.99 (d, J = 4 Hz, 1H), 8.86 (d, J = 7.6 Hz, 1H), 7.56-7.72 (m, 3H), 7.56 (s, 1H), 5.51 (m, 1 H), 3.77-3.83 (m, 4H), 3.02 (s, 2H), 2.78 (s, 2H), 1.79 (m, 4H), 1.54 (d, J = 6.8 Hz, 6H) |
| 2A-70 | CH(CH₃)₂ | H | (3-hydroxyquinolin-4-yl pivaloyl) | ESI + MS (M + H) 419.5; ¹HNMR (400 MHz, CD₃OD) δ 8.99 (d, J = 4 Hz, 1H), 8.86 (d, J = 7.6 Hz, 1H), 7.56-7.72 (m, 3H), 7.56 (s, 1H), 5.51 (m, 1 H), 3.77-3.83 (m, 4H), 3.02 (s, 2H), 2.78 (s, 2H), 1.79 (m, 4H), 1.54 (d, J = 6.8 Hz, 6H) |
| 2A-71 | CH(CH₃)₂ | H | (7-azaindol-3-yl pivaloyl) | ESI + MS (M + H) 392.4; ¹HNMR (400 MHz, CD₃OD) δ 3.30 (d, J = 4 Hz, 1H), 8.19 (d, J = 8 Hz, 1H), 7.79 (s, 1H), 7.45 (s, 1H), 7.25 (m, 1H), 5.40 (m, 1 H), 3.73-3.88 (m, 4H), 2.93 (s, 2H), 2.69 (s, 2H), 1.67 (m, 4H), 1.44 (d, J = 6.4 Hz, 6H) |
| 2A-72 | CH(CH₃)₂ | H | (5-hydroxyisoquinolin-6-yl pivaloyl) | ESI + MS (M + H) 419.4; ¹HNMR (400 MHz, CD₃OD) δ 9.21 (s, 1H), 8.48 (d, J = 6.4 Hz, 1H), 8.17 (d, 1H), 7.58 (m, 1H), 7.49 (d, J = 8 Hz 1H), 7.45 (s, 1H), 5.40 (m, 1 H), 3.24-3.80 (m, 4H), 2.91 (s, 2H), 2.67 (s, 2H), 1.68 (m, 4H), 1.43 (d, J = 6.4 Hz, 6H) |
| 2A-73 | CH(CH₃)₂ | H | (8-hydroxyquinolin-7-yl pivaloyl) | ESI + MS (M + 23) 419.4; ¹HNMR (400 MHz, CD3OD) δ 9.00 (d, J = 4.8 Hz, 1H), 8.75 (d, J = 7.2 Hz, 1H), 7.857 (m, 1H), 7.58 (d, J = 9.2 Hz, 1H), 7.59 (d, J = 8 Hz, 1H), 7.45 (s, 1H), 5.40 (m, 1 H), 3.58 (m, 4H), 2.92 (s, 2H), 2.68 (s, 2H), 1.69 (m, 4H), 1.43 (d, J = 6.4 Hz, 6H) |
| 2A-74 | CH(CH₃)₂ | H | (4-(1H-pyrazol-4-yl)phenyl pivaloyl) | +ESI MS (M + H) 418.6; ¹HNMR (400 MHz, CD₃OD) δ 8.00 (s, 2H), 7.67 (d, J = 8 Hz, 1H), 7.61 (s, 1H), 7.41 (m, 2H), 7.22 (d, J = 7.6Hz, 1H), 5.36 (m, 1 H), 3.48-3.90 (m, 2H), 3.30 (m, 2H), 2.88 (s, 2H), 2.64 (s, 2H), 1.56-1.68 (m, 4H), 1.40 (d, J = 4.4 Hz, 6H) |

TABLE 2-continued

[Structure: R¹–N–N=C(R²)–fused cyclohexanone–spiro-piperidine–N–C(O)R⁴]

| Ex. | R¹ | R² | C(O)R⁴ | Analytical Data |
|---|---|---|---|---|
| 2A-75 | CH(CH₃)₂ | CH₃ | (1H-indazol-5-yl)carbonyl | +ESI MS (M + H) 406.6; ¹H NMR (400 MHz, CDCl₃) δ ppm 10.28 (br. s., 1 H) 8.12 (s, 1 H) 7.85 (s, 1 H) 7.41-7.61 (m, 2 H) 5.21-5.50 (m, 1 H) 3.29-4.02 (m, 4H) 2.69 (s, 2H) 2.58 (s, 2 H) 2.24 (s, 3 H) 1.49-1.77 (m, 4 H) 1.44 (d, J = 6.64 Hz, 6H) |
| 2A-76 | CH(CH₃)₂ | CN | (1H-indazol-5-yl)carbonyl | +ESI MS (M + H) 417.5; ¹H NMR (400 MHz, CD₃OD) δ ppm 8.11 (s, 1 H) 7.89 (d, J = 0.78 Hz, 1 H) 7.59 (dd, J = 8.60, 0.78 Hz, 1 H) 7.44 (dd, J = 8.60, 0.78 Hz, 1 H) 5.42 (dt, J = 13.24, 6.57 Hz, 1 H) 3.79 (br. s., 2 H) 3.54 (br. s., 2 H) 2.96 (s, 2 H) 2.71 (s, 2 H) 1.48-1.81 (m, 4 H) 1.44 (d, J = 6.64 Hz, 6 H) |
| 2A-77 | C(CH₃)₃ | CN | (1H-benzimidazol-5-yl)carbonyl | +ESI MS (M + H) 431.5; ¹H NMR (400 MHz, CD₃OD) δ ppm 8.26 (s, 1 H) 7.68 (br. s., 2 H) 7.34 (d, J = 8.60 Hz, 1 H) 3.80 (br. s., 2 H) 3.52 (br. s., 2 H) 2.98 (s, 2 H) 2.74 (s, 2 H) 1.46-1.80 (m, 13 H) |
| 2A-78 | C(CH₃)₃ | CN | (1H-indazol-5-yl)carbonyl | +ESI MS (M + H) 431.5; ¹H NMR (400 MHz, CD₃OD) δ ppm 8.11 (d, J = 0.98 Hz, 1 H) 7.89 (dd, J = 1.46, 0.88 Hz, 1 H) 7.59 (dt, J = 8.58, 0.88 Hz, 1 H) 7.44 (dd, J = 8.68, 1.46 Hz, 1 H) 3.78 (br. s., 2 H) 3.54 (br. s., 2 H) 2.98 (s, 2 H) 2.74 (s, 2 H) 1.52-1.82 (m, 13 H) |

Example 3

Preparation of 1 isopropyl-1'-(2-methyl-1H-benzo[d]imidazole-5-carbonyl)-4,6-dihydrospiro[indazole-5,4'-piperidin]-7(1H)-one (3A-1)

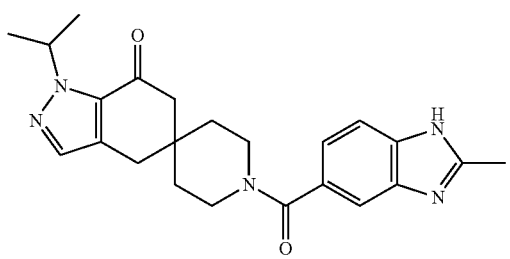

3A-1

2-Methyl-1H-benzimidazole-5-carboxylic acid (15 g) was taken up in tetrahydrofuran (500 mL), dimethylformamide (329 uL) and oxalyl chloride (22.1 mL) were added. The reaction solution was stirred at ambient temperature for 16 hours. The solution was concentrated in vacuo and the residue was taken up in dichloromethane and concentrated (x 2) under reduced pressure. To the resulting acid chloride was added tetrahydrofuran (500 mL), Preparation I-1A-1e (25.9 g) and triethylamine (71.2 mL). The solution was stirred at room temperature for 16 hours. To the reaction was added saturated, aqueous sodium bicarbonate (250 mL) and the solution was stirred for 5 min. The layers were separated and the aqueous layer was extracted with 1:1 ethyl acetate I tetrahydrofuran. The organic layers were combined, diluted with ethyl acetate (1 L) and washed with saturated aqueous, sodium bicarbonate (200 mL) and saturated, aqueous sodium chloride. The organic layer was dried over sodium sulfate, filtered and concentrated in vacuo to a light yellow solid. The solid was dissolved in hot methanol (300 mL) and then heated to reflux. To the solution was added 350 mL ethyl acetate and 300 mL of solvent was removed by distillation. Additional ethyl acetate was added dropwise until an internal temperature of 70° C. was reached. The solution was cooled to room temperature over 3 hours. The solids were collected by filtration and dried in a vacuum oven (40° C.) for 16 hours to afford the title compound as a white solid (20.5 g, 59%): +ESI MS (M+H) 406.5; $^1$H NMR (400 MHz, DMSO-$d_6$) δ ppm 12.25-12.33 (m, 1H), 7.35-7.51 (m, 3H), 7.05-7.16 (m, 1H), 5.16-5.31 (m, 1H), 3.32-3.58 (m, 4H), 2.77 (s, 2H), 2.57 (s, 2H), 1.40-1.52 (m, 4H), 1.32 (d, J=6.45 Hz, 6H).

In the present example it is to be understood that the starting material 2-Methyl-1H-benzimidazole-5-carboxylic acid employed in this example also exists as its tautomeric form 2-Methyl-1H-benzimidazole-6-carboxylic acid (also known as 2-Methyl-3H-benzimidazole-5-carboxylic acid) and each is designated by the same CAS No. 709-19-3. It is to be further understood that the instant example has been depicted above as one of two tautomeric forms of the compound with respect to the 2-methyl benzimidazolyl group and that the title compound is synonymous with the tautomeric form 1-isopropyl-1'-(2-methyl-1H-benzo[d]imidazole-6-carbonyl)-4,6-dihydrospiro[indazole-5,4'-piperidin]-7(1H)-one which is depicted as:

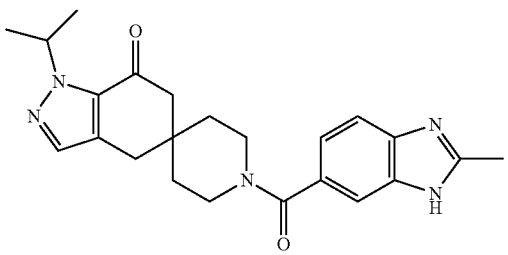 [SMILES: Cc1nc2ccc(C(=O)N3CCC4(CC3)CC(=O)c3c(cnn3C(C)C)C4)cc2[nH]1]

Example 4

Preparation of 1'-1H-indazole-5-carbonyl)-1-isopropyl-6-methyl-4,6-dihydrospiro[indazole-5,4'-piperidin]-7(1H)-one (4A-1)

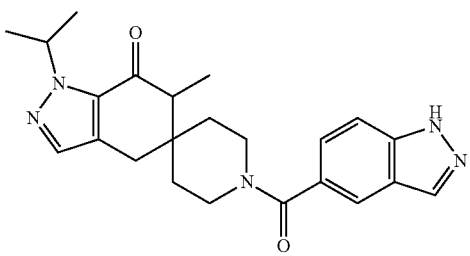

4A-1

Preparation 14A-1e (177 mg, 0.677 mmol), 1H-indazole-5-carboxylic acid (110 mg, 0.677 mmol), O-(azabenzotriazole-1-yl)-N,N,N',N'-tetramethyluronium hexafluorophosphate (257 mg, 0.677 mmol) and triethylamine (138 mg, 1.35 mmol) were combined in 3 mL of dimethylformamide and stirred at room temperature for 18 hours. To the reaction was added saturated, aqueous sodium bicarbonate (2 mL). The reaction was partitioned between ethyl acetate (80 mL) and water (20 mL). The phases were separated and the aqueous layer was extracted with ethyl acetate (50 mL). The organic phases were combined, dried over magnesium sulfate and concentrated to give an oil. The oil was purified by flash chromatography using 0-5% methanol in dichloromethane as eluent to afford the title compound as a solid (196 mg, 72%): +APCI MS (M+H) 406.2; $^1$H NMR (400 MHz, DMSO-$d_6$) s ppm 13.21 (br. s., 1H), 8.13 (s, 1H), 7.82 (s, 1H), 7.56 (d, J=8.60 Hz, 1H), 7.46 (s, 1H), 7.37 (dd, J=8.60, 1.37 Hz, 1H), 5.25 (m, 1H), 3.21-3.39 (m, 4H), 3.01-3.19 (m, 1H), 2.74-2.94 (m, 2H), 1.41-1.62 (m, 4H), 1.34 (d, J=6.64 Hz, 6H), 1.07 (d, J=7.23 Hz, 3H).

Example 5

Preparation of (+)-1'-(1H-indazole-5-carbonyl-4-isopropyl-6-methyl-4,6-dihydrospiro[indazole-5,4'-piperidin]-7(1H)-one (5A-1) and (−)-1'-(indazole-5-carbonyl)-1-isopropyl-6-methyl-4,6-dihydrospiro[indazole-5,4'-piperidin]-7(1H)-one (5A-2)

5A-1 and 5A-2

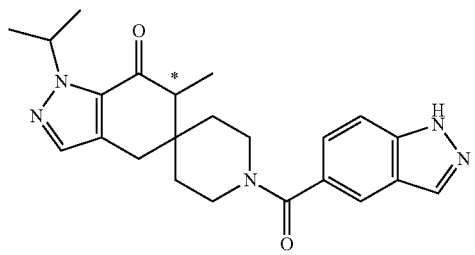

Racemic compound Example 4 (Compound 4A-1) was separated to give the corresponding two enantiomers using chiral HPLC: [Chiralpakl AD-H (10×250); mobile phase: 70:30 (CO$_2$/Ethanol); flow rate=10 mL/min]. Compound 5A-1: retention time=4.17 min; optical rotation results: c=0.0053 g/mL in ethanol; path length=1 dcm; observed rotation=+0.202 (D line of a sodium lamp (589 nm) at 20° C.); specific rotation=+38.1. Compound 5A-2: retention time=5.47 min; optical rotation results: c=0.0053 g/mL in ethanol; path length=1 dcm; observed rotation=−0.184 (D line of a sodium lamp (589 nm) at 20° C.); specific rotation=−34.1.

Example 6

Preparation of 1'-(1H-indazole-5-carbonyl)-1-isopropyl-6,6-dimethyl-4,6-dihydrospiro[indazole-5,4'-piperidin]-7(1H)-one (6A-1)

6A-1

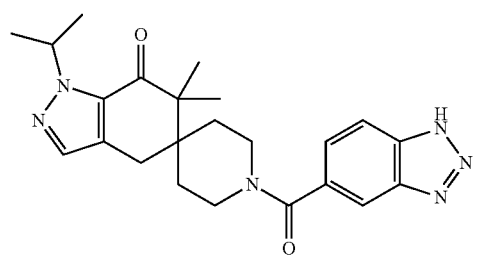

A solution of 1H-indazole-5-carboxylic acid (27 mg, 0.167 mmol) in dimethylformamide (2 mL) was treated with N-methyl morpholine (51 mg, 0.167 mmol) followed by 2-chloro-4,6-dimethoxy-1,3,5-triazine (29 mg, 167 mmol). The solution was stirred at ambient temperature for two hours. To the reaction was added Preparation I-6A-1b (46 mg, 0.17 mmol) and N-methyl morpholine (34 mg, 0.334 mmol) as a solution in dimethylformamide (2 mL). The reaction mixture was stirred at room temperature for 18 hours. To the reaction was added aqueous, saturated ammonium chloride (1 mL). The reaction was partitioned between ethyl acetate (30 mL) and water (5 mL). The phases were separated and the aqueous layer was extracted with ethyl acetate (30 mL). The organic phases were combined, dried over magnesium sulfate and concentrated to give an oil. The oil was purified by flash chromatography using 0-5% methanol in dichloromethane as eluent to afford the title compound as a solid (39 mg, 56%): +APCI MS (M+H) 420.3; $^1$H NMR (400 MHz, DMSO-$d_6$) δ ppm 13.18 (s, 1H), 8.10 (s, 1H). 7.80 (s, 1H), 7.53 (d, J=8.78 Hz, 1H). 7.42 (s, 1H), 7.34 (dd, J=8.58, 1.37 Hz, 1H), 5.24 (m, 1H), 3.84 (br. s., 6H), 1.38-1.72 (m, 4H), 1.32 (d, J=6.63 Hz, 6H), 1.06 (s, 6H).

Example 7

Preparation of 1'-(1H-benzo[d]imidazole-5-carbon)—isopropyl-3-methyl-4,6-dihydrospiro[indazole-5,4'-piperidin]-7(1H)-one (7A-1)

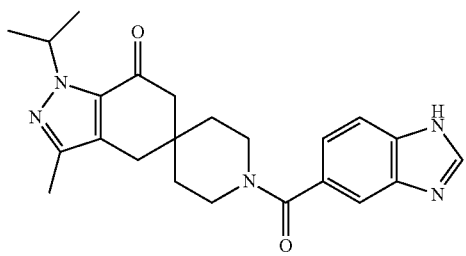

7A-1

Preparation I-2A-75f (150 mg, 0.50 mmol), 1H-benzo[d]imidazole-5-carboxylic acid (82 mg, 0.50 mmol), O-(azabenzotriazole-1-yl)-N,N,N',N'-tetramethyluronium hexafluorophosphate (198 mg, 0.50 mmol) and triethylamine (103 mg, 1.01 mmol) were combined in 3 mL of dimethylformamide and stirred at room temperature for 16 hours. The reaction was partitioned between 10 mL ethyl acetate and 10 mL saturated aqueous sodium bicarbonate. The organic phase was separated and then concentrated to give an oil. The oil was purified by flash chromatography using 5-10% ethanol in dichloromethane as eluent to afford the title compound as a solid (82 mg, 40%): +APCI MS (M+H) 4062; $^1$H NMR (400 MHz, CDCl$_3$) δ ppm 8.05 (s, 1H), 7.71 (s, 1H), 7.43 (m, 2H), 5.35 (m, 1H), 3.62 (m, 4H), 2.82 (s, 2H), 2.57 (br. s., 2H), 2.24 (s, 3H), 1.49-1.89 (m, 4H), 1.44 (d, J=6.64 Hz, 6H).

Example 8

Preparation of 1'-(1H-benzo[d]imidazole-5-carbonyl)-1-isopropyl-7-oxo-1,4,6,7-tetrahydrospiro[indazole-5,4'-piperidine]-3-carbonitrile (8A-1)

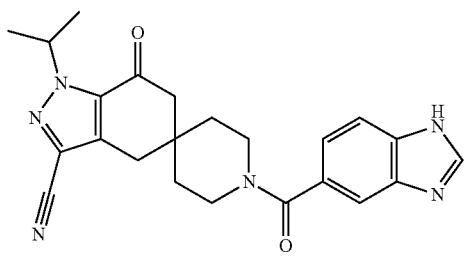

8A-1

Preparation I-2A-76b (50 mg, 0.18 mmol), 1H-benzo[d]imidazole-5-carboxylic acid (30 mg, 0.18 mmol), O-(azabenzotriazole-1-yl)-N,N,N',N'-tetramethyluronium hexafluorophosphate (77 mg, 0.20 mmol) and triethylamine (56 mg, 0.55 mmol) were combined in 2.3 mL of dichloromethane and stirred at room temperature for 16 hours. To the reaction was added saturated aqueous sodium bicarbonate (3 mL). The phases were separated and the aqueous phase was extracted with an additional portion of dichloromethane. The organic phases were combined and concentrated to give a residue. The residue was dissolved in methanol and potassium carbonate (49 mg, 0.36 mmol) was added. The mixture was stirred at ambient temperature for 5 minutes. The reaction was quenched with the addition of saturated aqueous ammonium chloride (2 mL) and the methanol was concentrated in vacuo to give a residue. The residue was partitioned between water and dichloromethane and then the phases were separated. The organic layer was washed with saturated aqueous sodium chloride, dried over magnesium sulfate and concentrated in vacuo to give a residue which was purified by flash chromatography using 0-10% methanol in ethyl acetate as eluent to afford the title compound as a solid (17 mg, to 22%): +ESI MS (M+H)=417.5; $^1$H NMR (400 MHz, CD$_3$OD) δ ppm 8.26 (s, 1H), 7.51-7.88 (m, 2H), 7.33 (d, J=9.77 Hz, 1H), 5.35-5.47 (m, 1H), 3.33-3.91 (m, 4H), 2.96 (s, 2H), 2.71 (s, 2H), 1.48-1.83 (m, 4H), 1.44 (d, J=6.64 Hz, 6H).

Example 9

Preparation of 1'-(1H-indazole-5-carbonyl)-1-(oxeten-3-yl)-4,6-dihydrospiro[indazole-5,4'-piperidin]-7(1H)-one (9A-1)

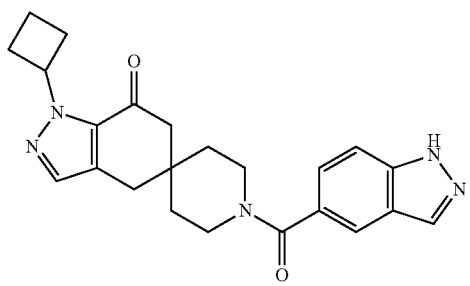

9A-1

Preparation I-2A-42g (12.4 mg. 0.042 mmol), 1H-indazole-5-carboxylic acid (7 mg, 0.043 mmol), O-(azabenzotriazole-1-yl)-N,N,N',N'-tetramethyluronium hexafluorophosphate (16 mg, 0.042 mmol) and triethylamine (14 mg, 0.14 mmol) were combined in 3 mL of dimethylformamide and stirred at room temperature for 16 hours. The reaction was diluted with ethyl acetate and washed with citric acid (0.5 M in water), saturated aqueous sodium chloride and saturated aqueous sodium bicarbonate one time each. The organic phase was separated and then dried over magnesium sulfate, filtered and concentrated to give a residue. The residue was purified by flash chromatography using 0-20% methanol in ethyl acetate as eluent to afford the title compound as an oil (7 mg, 40%): +APCI MS (M+H) 406.2; $^1$H NMR (400 MHz, CD$_3$OD) δ ppm 8.15 (s, 1H), 7.91 (s, 1H), 7.63 (d, J=8.60 Hz, 1H), 7.58 (s, 1H), 7.46 (dd, J=8.70, 1.47 Hz, 1H), 6.10-6.25 (m, 1H), 4.95-5.13 (m, 4H), 3.41-4.06 (m, 4H), 2.93 (s, 2H), 2.66 (s, 2H), 1.44-1.85 (m, 4H).

Example 10

Preparation of 1'-(1H-indazole-5-carbonyl-1-isopropyl-4,6-dihydrospiro[indazole-5,4'-piperidin]-7(1H)-one (10A-1)

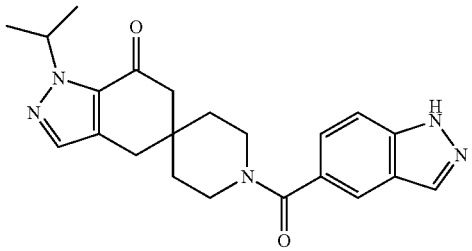

10A-1

Preparation I-1A-1e (30.3 g, 94.6 mmol) and 1H-indazole-5-carboxylic acid (16.96 g, 104.6 mmol) were suspended in dimethyl acetamide (430 mL) and 1-ethyl-3-[3-(dimethylamino)propyl]carbodiimide hydrochloride (22.3 g, 115 mmol) was added, followed by the dropwise addition of triethylamine (65 mL, 475 mmol). 1-Hydroxybenzotriazole hydrate (16.2 g, 106 mmol) was then added and the reaction mixture was stirred at 60° C. for 2 hours. The reaction was poured into half saturated, aqueous ammonium chloride (500 mL) and extracted with ethyl acetate (1×1 L, 2×500 mL). The combined organic layers were washed with aqueous sodium bicarbonate (2×500 mL), water (3×500 mL) and aqueous saturated sodium chloride (1×500 mL). The organic layer was dried over sodium sulfate, filtered and concentrated under reduced pressure to an oil. The oil was purified via flash column chromatography (1-6% methanol in dichloromethane) to afford the desired product (27.1 g). A small amount was crystallized using ethyl acetate/heptane. This was used to seed the following crystallization. The product was dissolved in ethyl acetate (100 mL) and heated to reflux until the solution turned hazy. A small amount of seed crystal was added. The mixture was cooled to room temperature and a precipitate formed and was stirred 80 hours. The precipitate was collected by filtration and washed with cold ethyl acetate (2×30 mL). The material was air dried and then further dried under high vacuum to afford the desired title product as an off-white solid (23 g, 62%). +ESI MS (M+H) 392.5; $^1$H NMR (400 MHz, DMSO-d) δ ppm 13.19 (s, 1H), 8.08-8.12 (m, 1H), 7.78-7.80 (m, 1H), 7.49-7.57 (m, 1H), 7.43 (s, 1H), 7.29-7.38 (m, 1H), 5.17-5.31 (m, 1H), 3.45 (br. s., 4H), 2.78 (s, 2H), 2.59 (s, 2H), 1.48 (br. s., 4H), 1.32 (d, J=6.63 Hz, 6H).

Example 11

Preparation of 1'-(4-1H-imidazol-2-yl)benzoyl)-1-isopropyl-4,6-dihydrospiro[indazole-5,4'-piperidin]-7(1H)-one (11A-1)

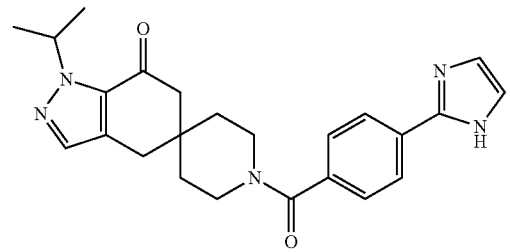

11A-1

4-(1H-imidazol-2-yl)benzoic acid (1.4 mg, 75 umol), anhydrous acetonitrile (400 ul), Preparation I-1A-1f (1.9 mg, 75 ul), triethylamine (21 ul, 150 umol) and O-(azabenzotriazole-1-yl)-N,N,N',N'-tetramethyluronium hexafluorophosphate (2.9 mg, 75 umol) were combined and heated to 30° C. for 14 hours. The reaction solution was concentrated in vacuo and purified by preparative HPLC to give the title compound. Preparative HPLC method: column=Luna 5u 100×21.2 mm, solvent phase A=0.1% trifluoroacetic acid in water, phase B=acetonitrile, flow rate=23 mL/min and detector=UV.

Gradient

| Time (min) | Phase B (%) | |
|---|---|---|
| 0 | 20 | |
| 1.5 | 20 | |
| 8 | 50 | linear |
| 8.2 | 100 | |
| 9.4 | 100 | |
| 9.6 | 20 | |
| 10 | 20 | |

Analytical HPLC method: column=welch materials XB-C18 2.1*50 mm, solvent phase A=H$_2$O (1 L H$_2$O with 0.5 mL NH$_3$.H$_2$O), solvent phase B=acetonitrile, flow rate: 0.8 mL/min. Retention time=2.419 minutes.

Gradient

| Time (min) | Phase A (%) | Phase B (%) |
|---|---|---|
| 0 | 95 | 5 |
| 0.5 | 95 | 5 |
| 3.4 | 0 | 100 |
| 4.2 | 0 | 100 |
| 4.21 | 95 | 5 |
| 4.70 | 95 | 5 |

Mass parameter: Mass range=170-1000 Fragmentor=50 Gas flow=10 L/min

Dry gas temperature=350° C. Capillary voltage (v)=2500 M+H=418

The compounds listed in Table 3 below were prepared using procedures analogous to those described above for the synthesis of Example 11, Compound 11A-1 using the appropriate starting materials which are available commercially, prepared using preparations well-known to those skilled in the art, or prepared in a manner analogous to routes described above for other intermediates. The compounds listed below were isolated initially as the free base and may be converted to their corresponding hydrochloride salt for testing. The compounds were characterized by the same analytical HPLC method referenced for Example 11, Compound 11A-1 (method A) or by a method in which 0.05% trifluoroacetic acid in water was substituted for solvent phase A (method B).

TABLE 3

| Example | R¹ | C(O)R⁴ | Analytical Data |
|---|---|---|---|
| 11A-2 | CH(CH₃)₂ | (2,6-dimethyl-5-amino-pyridin-4-yl)carbonyl | MS (M + H) 396; HPLC method A = 2.504 min |
| 11A-3 | CH(CH₃)₂ | [3-(1H-imidazol-4-yl)phenyl]carbonyl | MS (M + H) 418; HPLC method B = 2.490 min |
| 11A-4 | CH(CH₃)₂ | [3-methyl-1-(pyridin-3-yl)-1H-pyrazol-5-yl]carbonyl | MS (M + H) 433; HPLC method A = 2.649 min |
| 11A-5 | C(CH₃)₃ | [3-methyl-1-(pyridin-3-yl)-1H-pyrazol-5-yl]carbonyl | MS (M + H) 447; HPLC method A = 2.817 min |
| 11A-6 | CH(CH₃)₂ | (5-amino-2-phenyl-2H-1,2,3-triazol-4-yl)carbonyl | MS (M + H) 434; HPLC method B = 3.356 min |

TABLE 3-continued
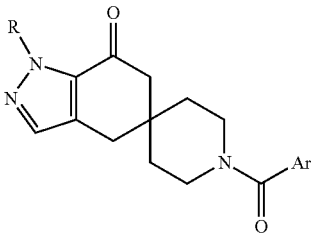
| Example | R¹ | C(O)R⁴ | Analytical Data |
|---|---|---|---|
| 11A-7 | C(CH₃)₃ | 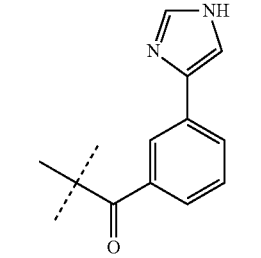 | MS (M + H) 432; HPLC method B = 2.637 min |
| 11A-8 | C(CH₃)₃ | 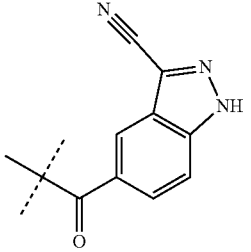 | MS (M + H) 447; HPLC method A = 2.560 min |
| 11A-9 | CH(CH₃)₂ | 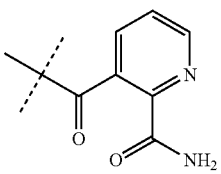 | MS (M + H) 417; HPLC method B = 2.983 min |
| 11A-10 | CH(CH₃)₂ | 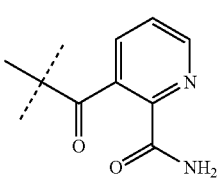 | MS (M + H) 396; HPLC method B = 2.584 min |
| 11A-11 | C(CH₃)₃ |  | MS (M + H) 410; HPLC method B = 2.814 min |

TABLE 3-continued
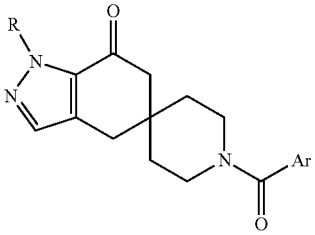
| Example | R¹ | C(O)R⁴ | Analytical Data |
|---|---|---|---|
| 11A-12 | C(CH₃)₃ | 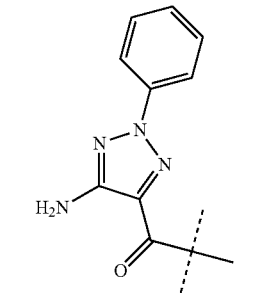 | MS (M + H) 448; HPLC method B = 2.291 min |
| 11A-13 | CH(CH₃)₂ | 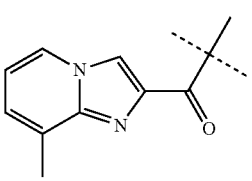 | MS (M + H) 432; HPLC method A = 2.369 min |
| 11A-14 | CH(CH₃)₂ | 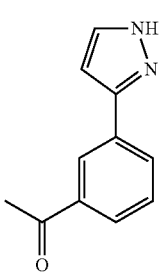 | MS (M + H) 406; HPLC method B = 2.489 min |
| 11A-15 | CH(CH₃)₂ | 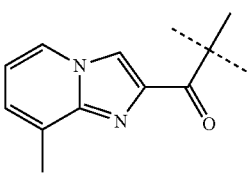 | MS (M + H) 418; HPLC method B = 2.944 min |
| 11A-16 | C(CH₃)₃ | 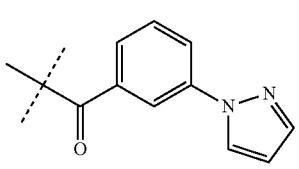 | MS (M + H) 420; HPLC method A = 2.945 min |
| 11A-17 | C(CH₃)₃ |  | MS (M + H) 432; HPLC method B = 2.781 min |

TABLE 3-continued
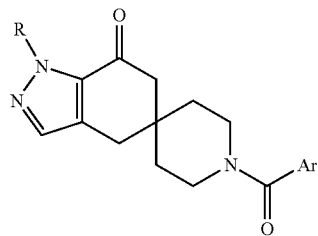
| Example | R¹ | C(O)R⁴ | Analytical Data |
|---|---|---|---|
| 11A-18 | CH(CH₃)₂ | | MS (M + H) 419; HPLC method B = 2.609 min |
| 11A-19 | C(CH₃)₃ | | MS (M + H) 406; HPLC method B = 2.845 min |
| 11A-20 | C(CH₃)₃ | | MS (M + H) 431; HPLC method B = 3.164 min |
| 11A-21 | CH(CH₃)₂ | | MS (M + H) 418; HPLC method B = 3.098 min |
| 11A-22 | C(CH₃)₃ | | MS (M + H) 452; HPLC method A = 2.869 min |
| 11A-23 | C(CH₃)₃ | | MS (M + H) 432; HPLC method A = 2.949 min |

TABLE 3-continued

| Example | R¹ | C(O)R⁴ | Analytical Data |
|---|---|---|---|
| 11A-24 | CH(CH₃)₂ | (6-morpholinopyridin-3-yl) ketone | MS (M + H) 438; HPLC method B = 2.578 min |
| 11A-25 | C(CH₃)₃ | (4-hydroxy-1,3-dimethyl-1H-pyrazol-5-yl) ketone | MS (M + H) 400; HPLC method B = 2.883 min |
| 11A-26 | C(CH₃)₃ | (2-(1H-pyrazol-3-yl)pyridin-4-yl) ketone | MS (M + H) 433; HPLC method A = 2.696 min |
| 11A-27 | C(CH₃)₃ | (7-methylimidazo[1,2-a]pyridin-2-yl) ketone | MS (M + H) 420; HPLC method B = 2.622 min |
| 11A-28 | CH(CH₃)₂ | (imidazo[1,2-a]pyridin-2-yl) ketone | MS (M + H) 392; HPLC method B = 2.406 min |
| 11A-29 | C(CH₃)₃ | (5-phenyl-1H-pyrazol-3-yl) ketone | MS (M + H) 433; HPLC method B = 2.614 min |
| 11A-30 | C(CH₃)₃ | (6-methyl-2-(methylamino)pyridin-3-yl) ketone | MS (M + H) 410; HPLC method B = 2.591 min |

TABLE 3-continued
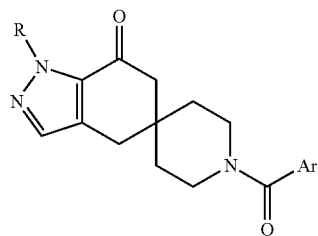
| Example | R¹ | C(O)R⁴ | Analytical Data |
|---|---|---|---|
| 11A-31 | CH(CH₃)₂ | | MS (M + H) 393; HPLC method A = 2.377 min |
| 11A-32 | C(CH₃)₃ | | MS (M + H) 406; HPLC method A = 2.679 min |
| 11A-33 | CH(CH₃)₂ | | MS (M + H) 393; HPLC method A = 2.245 min |
| 11A-34 | CH(CH₃)₂ | | MS (M + H) 392; HPLC method A = 2.694 min |
| 11A-35 | CH(CH₃)₂ | | MS (M + H) 409; HPLC method A = 1.947 min |
| 11A-36 | C(CH₃)₃ | | MS (M + H) 405; HPLC method B = 2.721 min |
| 11A-37 | CH(CH₃)₂ | | MS (M + H) 419; HPLC method B = 2.669 min |

TABLE 3-continued

| Example | R¹ | C(O)R⁴ | Analytical Data |
|---|---|---|---|
| 11A-38 | C(CH₃)₃ | (2,6-dimethyl-3-amino-pyridin-4-yl)carbonyl | MS (M + H) 410; HPLC method B = 2.542 min |
| 11A-39 | C(CH₃)₃ | (3H-imidazo[4,5-b]pyridin-6-yl)carbonyl | MS (M + H) 407; HPLC method A = 2.436 min |
| 11A-40 | CH(CH₃)₂ | (7-methylimidazo[1,2-a]pyridin-2-yl)carbonyl | MS (M + H) 406; HPLC method B = 2.431 min |
| 11A-41 | CH(CH₃)₂ | [3-(1H-imidazol-2-yl)phenyl]carbonyl | MS (M + H) 418; HPLC method B = 2.424 min |
| 11A-42 | CH(CH₃)₂ | (5-morpholinopyridin-2-yl)carbonyl | MS (M + H) 438; HPLC method A = 2.595 min |
| 11A-43 | CH(CH₃)₂ | (indolizin-2-yl)carbonyl | MS (M + H) 391; HPLC method A = 2.909 min |
| 11A-44 | C(CH₃)₃ | (3-hydroxy-6-methylpyridin-2-yl)carbonyl | MS (M + H) 397; HPLC method B = 2.787 min |

TABLE 3-continued
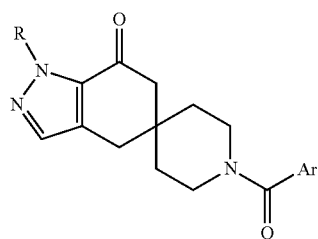
| Example | R¹ | C(O)R⁴ | Analytical Data |
|---|---|---|---|
| 11A-45 | C(CH₃)₃ | | MS (M + H) 406; HPLC method B = 2.858 min |
| 11A-46 | CH(CH₃)₂ | | MS (M + H) 396; HPLC method B = 2.391 min |
| 11A-47 | CH(CH₃)₂ | | MS (M + H) 392; HPLC method A = 2.704 min |
| 11A-48 | CH(CH₃)₂ | | MS (M + H) 392; HPLC method A = 2.522 min |
| 11A-49 | CH(CH₃)₂ | | MS (M + H) 383; HPLC method B = 2.546 min |
| 11A-50 | C(CH₃)₃ | | MS (M + H) 433; HPLC method A = 2.823 min |
| 11A-51 | C(CH₃)₃ | | MS (M + H) 406; HPLC method B = 2.554 min |

TABLE 3-continued
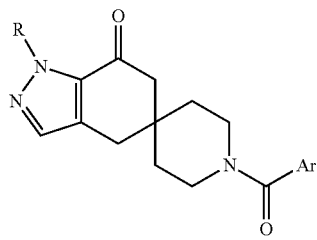
| Example | R¹ | C(O)R⁴ | Analytical Data |
|---|---|---|---|
| 11A-52 | CH(CH₃)₂ | | MS (M + H) 392; HPLC method B = 2.309 min |
| 11A-53 | C(CH₃)₃ | | MS (M + H) 432; HPLC method B = 2.603 min |
| 11A-54 | CH(CH₃)₂ | | MS (M + H) 419; HPLC method A = 2.577 min |
| 11A-55 | CH(CH₃)₂ | | MS (M + H) 406; HPLC method A = 2.509 min |
| 11A-56 | CH(CH₃)₂ | | MS (M + H) 392; HPLC method B = 2.353 min |
| 11A-57 | C(CH₃)₃ | | MS (M + H) 452; HPLC method A = 2.798 min |

TABLE 3-continued
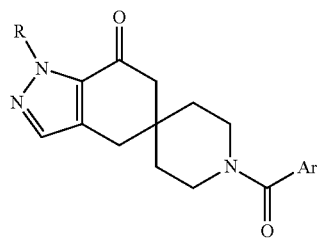
| Example | R¹ | C(O)R⁴ | Analytical Data |
|---|---|---|---|
| 11A-58 | C(CH₃)₃ | | MS (M + H) 407; HPLC method A = 2.572 min |
| 11A-59 | C(CH₃)₃ | | MS (M + H) 433; HPLC method A = 3.026 min |
| 11A-60 | CH(CH₃)₂ | | MS (M + H) 392; HPLC method A = 2.480 min |
| 11A-61 | C(CH₃)₃ | | MS (M + H) 418; HPLC method A = 2.732 min |
| 11A-62 | CH(CH₃)₂ | | MS (M + H) 419; HPLC method A = 2.514 min |
| 11A-63 | CH(CH₃)₂ | | MS (M + H) 419; HPLC method A = 2.445 min |

TABLE 3-continued

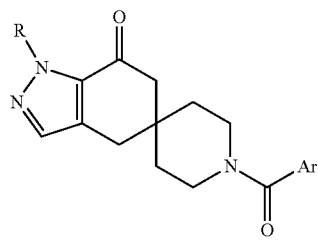

| Example | R¹ | C(O)R⁴ | Analytical Data |
|---|---|---|---|
| 11A-64 | C(CH₃)₃ | (3-(1H-imidazol-2-yl)phenyl pivaloyl) | MS (M + H) 432; HPLC method B = 2.613 min |
| 11A-65 | CH(CH₃)₂ | (3H-imidazo[4,5-b]pyridin-5-yl pivaloyl) | MS (M + H) 393; HPLC method A = 2.280 min |
| 11A-66 | CH(CH₃)₂ | (1-methyl-4-oxo-4,7-dihydro-1H-pyrazolo[3,4-b]pyridin-5-yl pivaloyl) | MS (M + H) 423; HPLC method B = 2.426 min |
| 11A-67 | C(CH₃)₃ | (imidazo[1,2-a]pyridin-6-yl pivaloyl) | MS (M + H) 406; HPLC method A = 2.648 min |
| 11A-68 | C(CH₃)₃ | (1H-imidazo[4,5-b]pyridin-5-yl pivaloyl) | MS (M + H) 407; HPLC method A = 2.471 min |
| 11A-69 | C(CH₃)₃ | (pyrrolo[1,2-c]pyrimidin-7-yl pivaloyl) | MS (M + H) 406; HPLC method B = 3.221 min |
| 11A-70 | C(CH₃)₃ | (1-methyl-4-oxo-4,7-dihydro-1H-pyrazolo[3,4-b]pyridin-5-yl pivaloyl) | MS (M + H) 437; HPLC method A = 2.036 min |

TABLE 3-continued

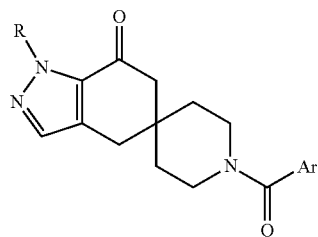

| Example | R¹ | C(O)R⁴ | Analytical Data |
|---|---|---|---|
| 11A-71 | C(CH₃)₃ | imidazo[1,2-a]pyridin-6-yl pivaloyl | MS (M + H) 392; HPLC method A = 2.457 min |
| 11A-72 | C(CH₃)₃ | 4-(1H-1,2,4-triazol-1-yl)phenyl pivaloyl | MS (M + H) 433; HPLC method A = 2.776 min |
| 11A-73 | C(CH₃)₃ | 1H-pyrrolo[2,3-b]pyridin-2-yl pivaloyl | MS (M + H) 406; HPLC method B = 2.804 min |
| 11A-74 | C(CH₃)₃ | 1H-indazol-6-yl pivaloyl | MS (M + H) 406; HPLC method B = 2.800 min |

Example 12

Preparation of 1-tert-butyl-1'-(1H-pyrrolo[2,3-b]pyridine-2-carbonyl)-4,6-dihydrospiro[indazole-5,4'-piperidin]-7(1H)-one 12A-1

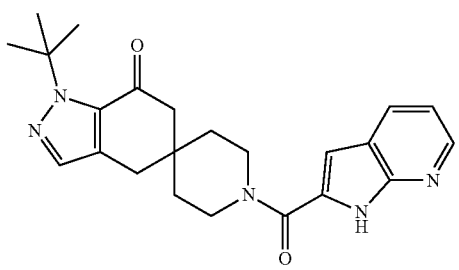

Preparation I-1a-2f (88 mg, 0.3 mmol), 1H-Pyrrolo[2,3-b]pyridine-2-carboxylic acid (48 mg, 0.3 mmol), O-(azabenzotriazole-1-yl)-N,N,N',N'-tetramethyluronium hexafluorophosphate (116 mg, 0.3 mmol) and triethylamine (0.83 mL, 0.59 mmol) were combined in 3 mL of dimethylformamide and stirred at room temperature for 30 hours. The reaction was partitioned between 10 mL ethyl acetate and 10 mL saturated aqueous ammonium chloride. The organic phase was separated and then washed with saturated, aqueous sodium bicarbonate and saturated, aqueous sodium chloride, dried over magnesium sulfate and concentrated to give a cream-colored solid. The solid was purified by flash chromatography using 0-20% methanol in ethyl acetate as eluent to afford the title compound as a white solid (91 mg, 76%): +ESI MS (M+H) 406.5; $^1$H NMR (400 MHz, CDCl₃) δ ppm 11.05 (br. s., 1H), 8.50 (dd, J=4.69, 1.56 Hz. 1H), 7.94 (dd, J=8.01, 1.56 Hz, 1H), 7.30 (s, 1H), 7.11 (dd, J=8.01, 4.69 Hz, 1H), 6.67 (s, 1H), 3.91 (br. s., 2H), 3.86 (br. s., 2H), 2.83 (s, 2H), 2.63 (s, 2H), 1.65 (br.s, 13H).

Example 13

Preparation of 3-bromo-1'-(7-bromo-2-oxo-2,3-dihydro-1H-benzo[d]imidazole-5-carbonyl)-1-tert-butyl-4,6-dihydrospiro[indazole-5,4'-piperidin]-7(1H)-one

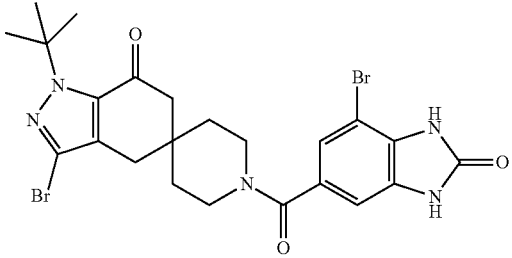

13A-1

Preparation I-13A-1c (190 mg, 0.504 mmol), 7-bromo-2-oxo-2,3-dihydro-1H-benzo[d]imidazole-5-carboxylic acid (130 mg, 0.506 mmol), O-(azabenzotriazole-1-yl)-N,N,N',N'-tetramethyluronium hexafluorophosphate (205 mg, 0.52 mmol) and triethylamine (100 mg, 1.0 mmol) was combined in dichloromethane (10 mL) and stirred at ambient temperature for 16 hours. To the reaction solution was added ethyl acetate (30 mL). The reaction solution was washed with 10% wt/wt aqueous citric acid (5 mL), saturated aqueous sodium bicarbonate (5 mL) and saturated, aqueous sodium chloride (5 mL). The organic layer was dried over magnesium sulfate and concentrated to give a residue which was purified by silica gel chromatography with a 2-8% methanol in dichloromethane gradient to give 13A-1 (52 mg, 18%): +ESI MS (M+H) 580.4; $^1$H NMR (400 MHz, CDCl$_3$) δ ppm 10.05 (br. s., 1H), 9.74 (br. s., 1H), 6.95-7.37 (m, 2H), 3.17-4.03 (m, 4H), 2.70 (br. s., 2H), 2.60 (br. s., 2H), 1.62 (br.s, 13H).

Pharmacological Data

Biological Protocols

The utility of the compounds of present invention, in the treatment of diseases (such as are detailed herein) in animals, particularly mammals (e.g., humans) may be demonstrated by the activity thereof in conventional assays known to one of ordinary skill in the art, including the in vitro and in vivo assays described below. Such assays also provide to a means whereby the activities of the compound of the present invention can be compared with the activities of other known compounds.

Direct Inhibition of the Activities of ACC1 and ACC2

The ACC inhibitory activity of the compound of the present invention was demonstrated by methods based on standard procedures. For example direct inhibition of ACC activity, for the compound of Formula (I) was determined using preparations of recombinant human ACC1 (rhACC1) and recombinant human ACC2 (rhACC2). Representative sequences of the recombinant human ACC1 and ACC2 that can be used in the assay are provided in FIG. 1 (SEQ ID NO. 1) and FIG. 2 (SEQ. ID NO. 2), respectively.

[1] Preparation of rhACC1. Two liters of SF9 cells, infected with recombinant baculovirus containing full length human ACC1 cDNA, were suspended in ice-cold lysis buffer (25 mM Tris, pH 7.5; 150 mM NaCl: 10% glycerol; 5 mM imidazole (EMD Bioscience; Gibbstown, N.J.); 2 mM TCEP (BioVectra; Charlottetown, Canada); Benzonase nuclease (10000 U/100 g cell paste; Novagen; Madison, Wis.); EDTA-free protease inhibitor cocktail (1 tab/50 mL; Roche Diagnostics; Mannheim, Germany). Cells were lysed by 3 cycles of freeze-thaw and centrifuged at 40,000×g for 40 minutes (4° C.). Supernatant was directly loaded onto a HisTrap FF crude column (GE Healthcare; Piscataway, N.J.) and eluted with an imidazole gradient up to 0.5 M over 20 column volumes (CV). ACC1-containing fractions were pooled and diluted 1:5 with 25 mM Tris, pH 7.5, 2 mM TCEP, 10% glycerol and direct loaded onto a CaptoQ (GE Healthcare) column and eluted with an NaCl gradient up to 1 M over 20 CV's. Phosphate groups were removed from purified ACC1 by incubation with lambda phosphatase (100 U/10 μM target protein; New England Biolabs; Beverly. MA) for 14 hours at 4=C; okadaic acid was added (1 μM final concentration; Roche Diagnostics) to inhibit the phosphatase. Purified ACC1 was exchanged into 25 mM Tris, pH 7.5, 2 mM TCEP, 10% glycerol, 0.5 M NaCl by 6 hour dialysis at 4° C. Aliquots were prepared and frozen at −80° C.

[2] Measurement of rhACC1 inhibition. hACC1 was assayed in a Costar #3676 (Costar, Cambridge, Mass.) 384-well plate using the Transcreener ADP detection FP assay kit (Bellbrook Labs, Madison, Wis.) using the manufacturer's recommended conditions for a 50 μM ATP reaction. The final conditions for the assay were 50 mM HEPES, pH 7.2, 10 mM MgCl$_2$ 7.5 mM tripotassium citrate, 2 mM DTT, 0.1 mg/mL BSA, 30 μM acetyl-CoA, 50 μM ATP, and 10 mM KHCO$_3$. Typically, a 10 μl reaction was run for 120 min at 25° C., and 10 μl of Transcreener stop and detect buffer was added and the combination incubated at room temp for an additional 1 hour. The data was acquired on a Envision Fluorescence reader (Perkinelmer) using a 620 excitation Cy5 FP general dual mirror, 620 excitation Cy5 FP filter, 688 emission (S) and a 688 (P) emission filter.

[3] Preparation of rhACC2. Human ACC2 inhibition was measured using purified recombinant human ACC2 (hrACC2). Briefly, a full length Cytomax done of ACC2 was purchased from Cambridge Bioscience Limited and was sequenced and subcloned into PcDNA5 FRT TO-TOPO (Invitrogen, Carlsbad, Calif.). The ACC2 was expressed in CHO is cells by tetracycline induction and harvested in 5 liters of DMEM/F12 with glutamine, biotin, hygromycin and blasticidin with 1 μg/mL tetracycline (Invitrogen, Carlsbad, Calif.). The conditioned medium containing ACC2 was then applied to a Softlink Soft Release Avidin column (Promega, Madison, Wis.) and eluted with 5 mM biotin. 4 mgs of ACC2 were eluted at a concentration of 0.05 mg/mL (determined by A280) with an estimated purity of 95% (determined by A280). The purified ACC2 was dialyzed in 50 mM Tris, 200 mM NaCl, 4 mM DTT, 2 mM EDTA, and 5% glycerol. The pooled protein was frozen and stored at −80° C., with no loss of activity upon thawing. For measurement of ACC2 activity and assessment of ACC2 inhibition, test compounds were dissolved in DMSO and added to the rhACC2 enzyme as a 5× stock with a final DMSO concentration of 1%.

[4] Measurement of human ACC2 inhibition. hACC2 was assayed in a Costar #3676 (Costar, Cambridge, Mass.) 384-well plate using the Transcreener ADP detection FP assay kit (Bellbrook Labs. Madison, Wis.) using the manufacturer's recommended conditions for a 50 uM ATP reaction. The final conditions for the assay were 50 mM HEPES, pH 7.2, 5 mM MgCl$_2$ 5 mM tripotassium citrate, 2 mM DTT, 0.1 mg/mL BSA, 30 μM acetyl-CoA, 50 μM ATP, and 8 mM KHCO$_3$. Typically, a 10 μl reaction was run for 50 min at 25° C., and 10 μl of Transcreener stop and detect buffer was added and the combination incubated at room temp for an additional 1 hour. The data was acquired on an Envision Fluorescence reader (Perkinelmer) using a 620 excitation Cy5 FP general dual mirror, 620 excitation Cy5 FP filter, 688 emission (S) and a 688 (P) emission filter.

The results using the recombinant hACC1 and recombinant hACC2 Transcreener assays described above are summarized in the table below for the Compounds of Formula (I) exemplified in the Examples above.

| Example | hACC1 (nM) | n | hACC2 (nM) | n |
|---|---|---|---|---|
| 1A-1 | 267 | 3 | 68 | 3 |
| 1A-2 | 444 | 3 | 62.3 | 3 |
| 1A-3 | 646 | 3 | 155 | 6 |
| 1A-4 | 2980 | 3 | 719 | 3 |
| 1A-5 | 800 | 3 | 127 | 3 |
| 2A-1 | 282 | 3 | 69.7 | 4 |
| 2A-2 | 8300 | 3 | 3570 | 3 |
| 2A-3 | 2720 | 2 | 680 | 3 |
| 2A-4 | 8730 | 3 | 2530 | 3 |
| 2A-5 | 1220 | 3 | 481 | 3 |
| 2A-6 | 640 | 3 | 88.8 | 4 |
| 2A-7 | 4340 | 3 | 965 | 4 |
| 2A-8 | 16000 | 2 | 4890 | 3 |
| 2A-9 | 4260 | 1 | 1850 | 3 |
| 2A-10 | 188 | 3 | 29.2 | 3 |
| 2A-11 | 261 | 3 | 33.5 | 3 |
| 2A-12 | 94 | 3 | 32.2 | 9 |
| 2A-13 | 95.3 | 3 | 28 | 5 |
| 2A-14 | 172 | 3 | 27 | 7 |
| 2A-15 | 2030 | 3 | 775 | 3 |
| 2A-16 | 46.9 | 3 | 13.6 | 7 |
| 2A-17 | 795 | 3 | 287 | 3 |
| 2A-18 | 1010 | 2 | 458 | 3 |
| 2A-19 | 57.4 | 3 | 22.1 | 9 |
| 2A-20 | 121 | 4 | 93 | 5 |
| 2A-21 | 93.3 | 2 | 32.7 | 4 |
| 2A-22 | 1890 | 1 | 334 | 3 |
| 2A-23 | 32.3 | 3 | 23.3 | 9 |
| 2A-24 | 30.7 | 3 | 15.8 | 5 |
| 2A-25 | 69.5 | 3 | 22.7 | 6 |
| 2A-26 | 43.8 | 3 | 42.4 | 4 |
| 2A-27 | 308 | 1 | 91.8 | 4 |
| 2A-28 | 47.8 | 3 | 17 | 5 |
| 2A-29 | 24.1 | 3 | 9.81 | 10 |
| 2A-30 | 170 | 2 | 51 | 3 |
| 2A-31 | 43.5 | 3 | 28.8 | 4 |
| 2A-32 | 37 | 3 | 28.6 | 6 |
| 2A-33 | 53.7 | 3 | 14.5 | 10 |
| 2A-34 | 72.4 | 2 | 32.1 | 3 |
| 2A-35 | 97.3 | 2 | 34.1 | 4 |
| 2A-36 | 123 | 2 | 29.6 | 4 |
| 2A-37 | 87.4 | 2 | 34.5 | 3 |
| 2A-38 | 297 | 2 | 99.7 | 3 |
| 2A-39 | 527 | 2 | 122 | 6 |
| 2A-40 | 262 | 2 | 116 | 3 |
| 2A-41 | 176 | 2 | 90 | 3 |
| 2A-42 | 1300 | 3 | 766 | 3 |
| 2A-43 | 304 | 2 | 149 | 3 |
| 2A-44 | 106 | 2 | 30.2 | 3 |
| 2A-45 | 73.7 | 2 | 32.9 | 3 |
| 2A-46 | 167 | 3 | 29.5 | 6 |
| 2A-47 | 48.2 | 3 | 15.9 | 5 |
| 2A-48 | 51.1 | 3 | 17.2 | 8 |
| 2A-49 | 92.1 | 2 | 71.6 | 3 |
| 2A-50 | 269 | 5 | 64.1 | 7 |
| 2A-51 | 72.7 | 2 | 29.9 | 3 |
| 2A-52 | 54.2 | 3 | 19.3 | 7 |
| 2A-53 | 39.6 | 3 | 17.2 | 8 |
| 2A-54 | 214 | 2 | 51.5 | 3 |
| 2A-55 | 266 | 2 | 105 | 3 |
| 2A-56 | 31.2 | 3 | 15.1 | 4 |
| 2A-57 | 66.5 | 4 | 20.8 | 5 |
| 2A-58 | 280 | 2 | 74.1 | 3 |
| 2A-59 | 115 | 3 | 69.2 | 4 |
| 2A-60 | 8240 | 1 | 3990 | 1 |
| 2A-61 | 2320 | 1 | 2190 | 1 |
| 2A-62 | 4210 | 1 | 1280 | 1 |
| 2A-63 | 9330 | 1 | 3200 | 1 |
| 2A-64 | 229 | 1 | 253 | 1 |
| 2A-65 | 74.9 | 1 | 51.5 | 1 |
| 2A-66 | 30000 | 1 | 14000 | 1 |
| 2A-67 | 799 | 4 | 653 | 3 |
| 2A-68 | 68.4 | 4 | 51.2 | 3 |
| 2A-69 | 122 | 4 | 42.9 | 3 |
| 2A-70 | 9790 | 4 | 3760 | 3 |
| 2A-71 | 1060 | 4 | 387 | 3 |
| 2A-72 | 599 | 4 | 290 | 3 |
| 2A-73 | 516 | 4 | 139 | 3 |
| 2A-74 | 128 | 4 | 47.3 | 3 |
| 2A-75 | 113 | 3 | 37.7 | 6 |
| 2A-76 | 6620 | 1 | 1500 | 3 |
| 2A-77 | 6160 | 1 | 1300 | 3 |
| 2A-78 | 3840 | 1 | 1270 | 3 |
| 3A-1 | 96.1 | 8 | 48.6 | 17 |
| 4A-1 | 399 | 2 | 125 | 3 |
| 5A-1 | 4480 | 1 | 866 | 3 |
| 5A-2 | 175 | 1 | 80.7 | 4 |
| 6A-1 | 1530 | 1 | 373 | 3 |
| 7A-1 | 63.2 | 1 | 39.8 | 4 |
| 8A-1 | 7620 | 1 | 1660 | 3 |
| 9A-1 | 704 | 3 | 264 | 3 |
| 10A-1 | 43.8 | 3 | 22.3 | 5 |
| 11A-1 | 147 | 4 | 31.8 | 4 |
| 11A-2 | 1480 | 2 | 658 | 4 |
| 11A-3 | 74.7 | 3 | 25.4 | 4 |
| 11A-4 | 19600 | 1 | 5800 | 3 |
| 11A-5 | 16400 | 1 | 13200 | 3 |
| 11A-6 | 989 | 1 | 459 | 3 |
| 11A-7 | 36.8 | 3 | 10.4 | 3 |
| 11A-8 | 40.9 | 1 | 26.8 | 3 |
| 11A-9 | 34.4 | 3 | 19.7 | 5 |
| 11A-10 | 6670 | 1 | 789 | 3 |
| 11A-11 | 10600 | 1 | 1450 | 3 |
| 11A-12 | 152 | 1 | 850 | 3 |
| 11A-13 | 37.6 | 1 | 35.7 | 3 |
| 11A-14 | 418 | 1 | 253 | 3 |
| 11A-15 | 112 | 4 | 43.8 | 5 |
| 11A-16 | 621 | 1 | 190 | 3 |
| 11A-17 | 129 | 2 | 48.4 | 3 |
| 11A-18 | 235 | 2 | 56.3 | 4 |
| 11A-19 | 242 | 2 | 71.6 | 3 |
| 11A-20 | 25.5 | 3 | 8.46 | 3 |
| 11A-21 | 112 | 1 | 73.4 | 3 |
| 11A-22 | 1260 | 1 | 539 | 3 |
| 11A-23 | 87.1 | 3 | 20.4 | 5 |
| 11A-24 | 6060 | 1 | 836 | 3 |
| 11A-25 | 331 | 1 | 745 | 3 |
| 11A-26 | 130 | 2 | 41.5 | 4 |
| 11A-27 | 584 | 1 | 309 | 3 |
| 11A-28 | 917 | 1 | 391 | 3 |
| 11A-29 | 151 | 1 | 64.5 | 5 |
| 11A-30 | 224 | 2 | 106 | 4 |
| 11A-31 | 117 | 1 | 83.4 | 3 |
| 11A-32 | 155 | 1 | 96.4 | 3 |
| 11A-33 | 272 | 2 | 93.1 | 4 |
| 11A-34 | 2140 | 1 | 638 | 3 |
| 11A-35 | 3340 | 1 | 2130 | 3 |
| 11A-36 | 194 | 2 | 75.6 | 4 |
| 11A-37 | 1030 | 1 | 463 | 3 |
| 11A-38 | 2170 | 2 | 1030 | 4 |
| 11A-39 | 69 | 2 | 81.3 | 4 |
| 11A-40 | 1140 | 2 | 588 | 4 |
| 11A-41 | 122 | 4 | 30.1 | 5 |
| 11A-42 | 11700 | 1 | 2850 | 3 |
| 11A-43 | 143 | 1 | 45.6 | 3 |
| 11A-44 | 4170 | 1 | 4600 | 3 |
| 11A-45 | 1500 | 1 | 745 | 3 |
| 11A-46 | 391 | 2 | 97.1 | 4 |
| 11A-47 | 850 | 1 | 373 | 3 |
| 11A-48 | 78.9 | 2 | 41.2 | 4 |
| 11A-49 | 13500 | 1 | 4910 | 3 |

-continued

| Example | hACC1 (nM) | n | hACC2 (nM) | n |
|---|---|---|---|---|
| 11A-50 | 581 | 1 | 371 | 3 |
| 11A-51 | 110 | 1 | 108 | 3 |
| 11A-52 | 550 | 1 | 176 | 3 |
| 11A-53 | 68.3 | 3 | 22.8 | 5 |
| 11A-54 | 1500 | 1 | 295 | 3 |
| 11A-55 | 213 | 2 | 60.4 | 4 |
| 11A-56 | 1010 | 1 | 359 | 3 |
| 11A-57 | 9230 | 1 | 2330 | 3 |
| 11A-58 | 131 | 1 | 73.6 | 3 |
| 11A-59 | 86.8 | 1 | 80.1 | 3 |
| 11A-60 | 404 | 1 | 171 | 3 |
| 11A-61 | 2570 | 1 | 1350 | 3 |
| 11A-62 | 338 | 2 | 112 | 4 |
| 11A-63 | 8720 | 1 | 2550 | 3 |
| 11A-64 | 105 | 3 | 24.4 | 4 |
| 11A-65 | 1080 | 1 | 388 | 3 |
| 11A-66 | 4080 | 1 | 1390 | 3 |
| 11A-67 | 203 | 1 | 139 | 3 |
| 11A-68 | 825 | 2 | 285 | 4 |
| 11A-69 | 580 | 2 | 288 | 4 |
| 11A-70 | 1860 | 1 | 1040 | 3 |
| 11A-71 | 1560 | 1 | 285 | 3 |
| 11A-72 | 867 | 1 | 153 | 3 |
| 11A-73 | 37.4 | 1 | 37.4 | 3 |
| 11A-74 | 23.7 | 3 | 16.8 | 4 |
| 12A-1 | 39.5 | 3 | 67.3 | 4 |
| 13A-1 | 264 | 3 | 316 | 3 |

Acute In vivo Assessment of ACC Inhibition in Experimental Animals

The ACC inhibitory activity of the compounds of the present invention can be confirmed in vivo by evaluation of their ability to reduce malonyl-CoA levels in liver and muscle tissue from treated animals.

Measurement of malonyl-CoA production inhibition in experimental animals. In this method, male Sprague-Dawley Rats, maintained on standard chow and water ad libitum (225-275 g), were randomized prior to the study. Animals were either fed, or fasted for 18 hours prior to the beginning of the experiment Two hours into the light cycle the animals were orally dosed with a volume of 5 mL/kg, (0.5% methyl cellulose; vehicle) or with the appropriate compound (prepared in vehicle). Fed vehicle controls were included to determine baseline tissue malonyl-CoA levels while fasted animals were included to determine the effect fasting had on malonyl-CoA levels. One hour alter compound administration the animals were asphyxiated with $CO_2$ and the tissues were removed. Specifically, blood was collected by cardiac puncture and placed into BD Microtainer tubes containing EDTA (BD Biosciences. NJ), mixed, and placed on ice. Plasma was used to determine drug exposure. Liver and quadriceps were removed, immediately freeze-clamped, wrapped in foil and stored in liquid nitrogen.

Tissues were pulverized under liquid $N_2$ to ensure uniformity in sampling. Malonyl-CoA was extracted from the tissue (150-200 mg) with 5 volumes 10% tricarboxylic acid in Lysing Matrix A (MP Biomedicals, PN 6910) in a FastPrep FP120 (Thermo Scientific, speed=5.5; for 45 seconds). The supernatant containing malonyl-CoA was removed from the cell debris after centrifugation at 15000×g for 30 minutes (Eppendorf Centrifuge 5402). Samples were stably frozen at −80 C until analysis is completed.

Analysis of malonyl CoA levels in liver and muscle tissue can be evaluated using the following methodology.

The method utilizes the following materials: Malonyl-CoA tetralithium salt and malonyl-$^{13}C_3$-CoA trilithium salt which were purchased from Isotec (Miamisburg, Ohio, USA), sodium perchlorate (Sigma, cat no. 410241), trichloroacetic acid (ACROS, cat no. 42145), phosphoric acid (J. T. Baker, cat no. 0260-01), ammonium formate (Fluka, cat no. 17843), methanol (HPLC grade, J. T. Baker, cat no. 9093-33), and water (HPLC grade, J. T. Baker, 4218-03) were used to make the necessary mobile phases. Strata-X on-line solid phase extraction columns, 25 μm, 20 mm×2.0 mm I.D (cat no. 00M-S033-B0-CB) were obtained from Phenomenex (Torrance, Calif., USA). SunFire C18 reversed-phase columns, 3.5 μm, 100 mm×3.0 mm I.D. (cat no. 186002543) were purchased from Waters Corporation (Milford, Mass., USA).

This method may be performed utilizing the following equipment Two-dimensional chromatography using an Agilent 1100 binary pump, an Agilent 1100 quaternary pump and two Valco Cheminert 6-port two position valves. Samples were introduced via a LEAP HTC PAL auto sampler with Peltier cooled stack maintained at 10° C. and a 20 μL sampling loop. The needle wash solutions for the autosampler are 10% trichloroacetic acid in water (w/v) for Wash 1 and 90:10 methanol:water for Wash 2. The analytical column (Sunfire) was maintained at 35° C. using a MicroTech Scientific Micro-LC Column Oven. The eluent was analyzed on an ABI Sdex API3000 triple quadrupole mass spectrometer with Turbo Ion Spray.

Two-dimensional chromatography was performed in parallel using distinct gradient elution conditions for on-line solid phase extraction and reversed-phase chromatography. The general design of the method was such that the first dimension was utilized for sample dean-up and capture of the analyte of interest followed by a brief coupling of both dimensions for elution from the first dimension onto the second dimension. The dimensions were subsequently uncoupled allowing for gradient elution of the analyte from the second dimension for quantification while simultaneously preparing the first dimension for the next sample in the sequence. When both dimensions were briefly coupled together, the flow of the mobile phase in the first dimension was reversed for analyte elution on to the second dimension, allowing for optimal peak width, peak shape, and elution time.

The first dimension of the HPLC system utilized the Phenomenex strata-X on-line solid phase extraction column and the mobile phase consisted of 100 mM sodium perchlorate/ 0.1% (v/v) phosphoric acid for solvent A and methanol for solvent B.

The second dimension of the HPLC system utilized the Waters SunFire C18 reversed-phase column and the mobile phase consisted of 100 mM ammonium formate for solvent A and methanol for solvent B. The initial condition of the gradient was maintained for 2 minutes and during this time the analyte was transferred to the analytical column. It was important that the initial condition was at a sufficient strength to elute the analyte from the on-line SPE column while retaining it on the analytical. Afterwards, the gradient rose linearly to 74.5% A in 4.5 minutes before a wash and re-equilibration step.

Mass spectrometry when coupled with HPLC can be a highly selective and sensitive method for quantitatively measuring analytes in complex matrices but is still subject to interferences and suppression. By coupling a two dimensional HPLC to the mass spectrometer, these interferences were significantly reduced. Additionally, by utilizing the Multiple Reaction Monitoring (MRM) feature of the triple quadrupole mass spectrometer, the signal-to-noise ratio was significantly improved.

For this assay, the mass spectrometer was operated in positive ion mode with a TurbolonSpray voltage of 2250V. The nebulizing gas was heated to 450° C. The Declustering Potential (DP), Focusing Potential (FP), and Collision Energy (CE) were set to 60, 340, and 42 V, respectively. Quadrupole 1 (Q1) resolution was set to unit resolution with Quadrupole 3 (Q3) set to low. The CAD gas was set to 8. The MRM transitions monitored were for malonyl CoA: 854.1-347.0 m/z (L. Gao et al. (2007) *J. Chromatogr. B* 853, 303-313); and for malonyl-$^{13}C_3$-CoA: 857.1-350.0 m/z with dwell times of 200 ms. The eluent was diverted to the mass spectrometer near the expected elution time for the analyte, otherwise it was diverted to waste to help preserve the source and improve robustness of the instrumentation. The resulting chromatograms were integrated using Analyst software (Applied Biosystems). Tissue concentrations for malonyl CoA were calculated from a standard curve prepared in a 10% solution of trichloroacetic acid in water.

Samples comprising the standard curve for the quantification of malonyl-CoA in tissue extracts were prepared in 10% (wv) trichloroacetic acid (TCA) and ranged from 0.01 to 1 μmol/μL. Malonyl-$^{13}C_3$-CoA (final concentration of 0.4 μmol/μL) was added to each standard curve component and sample as an internal standard.

Six intra-assay quality controls were prepared; three from a pooled extract prepared from fasted animals and three from a pool made from fed animals. These were run as independent samples spiked with 0, 0.1 or 0.3 pmol/μL $^{12}C$-molly-CoA as well as malonyl-$^{13}C_3$-CoA (0.4 pmol/μL). Each intra-assay quality control contained 85% of aqueous tissue extract with the remaining portion contributed by internal standard (0.4 pmol/μL) and $^{12}C$-malonyl-CoA. Inter assay controls were included in each run; they consist of one fasted and one fed pooled sample of quadriceps and/or one fasted and one fed pooled sample of liver. All such controls are spiked with malonyl-$^{13}C_3$-CoA (0.4 pmol/μL).

What is claimed is:

1. A compound of Formula (I)

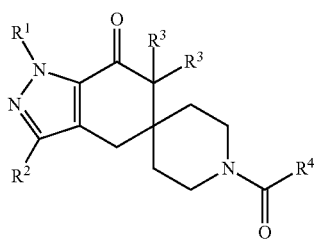

wherein
R¹ is $(C_1-C_6)$alkyl, $(C_3-C_7)$cycloalkyl, tetrahydrofuranyl or oxetanyl; wherein said $(C_1-C_6)$alkyl is optionally substituted with $(C_1-C_3)$alkoxy, phenyl, or tetrahydrofuranyl;

R² is hydrogen, halo, $(C_1-C_3)$alkyl, or cyano;

R³ are each independently hydrogen or $(C_1-C_3)$alkyl;

R⁴ is naphthyl optionally substituted with one to four substituents independently selected from $(C_1-C_3)$alkyl, $(C_1-C_3)$alkoxy, halo, amino, $(C_1-C_3)$alkylamino, di$(C_1-C_3)$alkylamino, hydroxy, cyano, amido, phenyl, 5 to 6 membered heteroaryl or 5 to 6 membered heterocyclyl;

or a pharmaceutically acceptable salt thereof.

2. The compound according to claim 1 wherein R¹ is $(C_1-C_6)$alkyl, $(C_3-C_7)$cycloalkyl, or tetrahydrofuranyl; and R² is hydrogen or methyl.

3. The compound according to claim 1 wherein R¹ is isopropyl or t-butyl; R² is hydrogen; and each R³ is hydrogen.

4. A pharmaceutical composition comprising a therapeutically effective amount of a compound of claim 1, or a pharmaceutically acceptable salt thereof, and a pharmaceutically acceptable excipient, diluent or carrier.

* * * * *

SEQUENCE LISTING

<160> NUMBER OF SEQ ID NOS: 2

<210> SEQ ID NO 1
<211> LENGTH: 2356
<212> TYPE: PRT
<213> ORGANISM: Homo sapiens

<400> SEQUENCE: 1

```
Met Ala His His His His His His Asp Glu Val Asp Asp Glu Pro Ser
1               5                   10                  15

Pro Leu Ala Gln Pro Leu Glu Leu Asn Gln His Ser Arg Phe Ile Ile
            20                  25                  30

Gly Ser Val Ser Glu Asp Asn Ser Glu Asp Glu Ile Ser Asn Leu Val
        35                  40                  45

Lys Leu Asp Leu Leu Glu Lys Glu Gly Ser Leu Ser Pro Ala Ser Val
    50                  55                  60

Gly Ser Asp Thr Leu Ser Asp Leu Gly Ile Ser Ser Leu Gln Asp Gly
65                  70                  75                  80

Leu Ala Leu His Ile Arg Ser Ser Met Ser Gly Leu His Leu Val Lys
                85                  90                  95

Gln Gly Arg Asp Arg Lys Lys Ile Asp Ser Gln Arg Asp Phe Thr Val
            100                 105                 110

Ala Ser Pro Ala Glu Phe Val Thr Arg Phe Gly Gly Asn Lys Val Ile
        115                 120                 125

Glu Lys Val Leu Ile Ala Asn Asn Gly Ile Ala Ala Val Lys Cys Met
    130                 135                 140

Arg Ser Ile Arg Arg Trp Ser Tyr Glu Met Phe Arg Asn Glu Arg Ala
145                 150                 155                 160

Ile Arg Phe Val Val Met Val Thr Pro Glu Asp Leu Lys Ala Asn Ala
                165                 170                 175

Glu Tyr Ile Lys Met Ala Asp His Tyr Val Pro Val Pro Gly Gly Pro
            180                 185                 190

Asn Asn Asn Asn Tyr Ala Asn Val Glu Leu Ile Leu Asp Ile Ala Lys
        195                 200                 205

Arg Ile Pro Val Gln Ala Val Trp Ala Gly Trp Gly His Ala Ser Glu
    210                 215                 220

Asn Pro Lys Leu Pro Glu Leu Leu Leu Lys Asn Gly Ile Ala Phe Met
225                 230                 235                 240
```

```
Gly Pro Pro Ser Gln Ala Met Trp Ala Leu Gly Asp Lys Ile Ala Ser
                245                 250                 255

Ser Ile Val Ala Gln Thr Ala Gly Ile Pro Thr Leu Pro Trp Ser Gly
            260                 265                 270

Ser Gly Leu Arg Val Asp Trp Gln Glu Asn Asp Phe Ser Lys Arg Ile
        275                 280                 285

Leu Asn Val Pro Gln Glu Leu Tyr Glu Lys Gly Tyr Val Lys Asp Val
    290                 295                 300

Asp Asp Gly Leu Gln Ala Glu Glu Val Gly Tyr Pro Val Met Ile
305                 310                 315                 320

Lys Ala Ser Glu Gly Gly Gly Lys Gly Ile Arg Lys Val Asn Asn
                325                 330                 335

Ala Asp Asp Phe Pro Asn Leu Phe Arg Gln Val Gln Ala Glu Val Pro
            340                 345                 350

Gly Ser Pro Ile Phe Val Met Arg Leu Ala Lys Gln Ser Arg His Leu
        355                 360                 365

Glu Val Gln Ile Leu Ala Asp Gln Tyr Gly Asn Ala Ile Ser Leu Phe
    370                 375                 380

Gly Arg Asp Cys Ser Val Gln Arg Arg His Gln Lys Ile Ile Glu Glu
385                 390                 395                 400

Ala Pro Ala Thr Ile Ala Thr Pro Ala Val Phe Glu His Met Glu Gln
                405                 410                 415

Cys Ala Val Lys Leu Ala Lys Met Val Gly Tyr Val Ser Ala Gly Thr
            420                 425                 430

Val Glu Tyr Leu Tyr Ser Gln Asp Gly Ser Phe Tyr Phe Leu Glu Leu
        435                 440                 445

Asn Pro Arg Leu Gln Val Glu His Pro Cys Thr Glu Met Val Ala Asp
    450                 455                 460

Val Asn Leu Pro Ala Ala Gln Leu Gln Ile Ala Met Gly Ile Pro Leu
465                 470                 475                 480

Tyr Arg Ile Lys Asp Ile Arg Met Met Tyr Gly Val Ser Pro Trp Gly
                485                 490                 495

Asp Ser Pro Ile Asp Phe Glu Asp Ser Ala His Val Pro Cys Pro Arg
            500                 505                 510

Gly His Val Ile Ala Ala Arg Ile Thr Ser Glu Asn Pro Asp Glu Gly
        515                 520                 525

Phe Lys Pro Ser Ser Gly Thr Val Gln Glu Leu Asn Phe Arg Ser Asn
    530                 535                 540

Lys Asn Val Trp Gly Tyr Phe Ser Val Ala Ala Gly Gly Leu His
545                 550                 555                 560

Glu Phe Ala Asp Ser Gln Phe Gly His Cys Phe Ser Trp Gly Glu Asn
                565                 570                 575

Arg Glu Glu Ala Ile Ser Asn Met Val Val Ala Leu Lys Glu Leu Ser
            580                 585                 590

Ile Arg Gly Asp Phe Arg Thr Val Glu Tyr Leu Ile Lys Leu Leu
        595                 600                 605

Glu Thr Glu Ser Phe Gln Met Asn Arg Ile Asp Thr Gly Trp Leu Asp
    610                 615                 620

Arg Leu Ile Ala Glu Lys Val Gln Ala Glu Arg Pro Asp Thr Met Leu
625                 630                 635                 640

Gly Val Val Cys Gly Ala Leu His Val Ala Asp Val Ser Leu Arg Asn
                645                 650                 655
```

-continued

```
Ser Val Ser Asn Phe Leu His Ser Leu Glu Arg Gly Gln Val Leu Pro
            660                 665                 670

Ala His Thr Leu Leu Asn Thr Val Asp Val Glu Leu Ile Tyr Glu Gly
        675                 680                 685

Val Lys Tyr Val Leu Lys Val Thr Arg Gln Ser Pro Asn Ser Tyr Val
    690                 695                 700

Val Ile Met Asn Gly Ser Cys Val Glu Val Asp Val His Arg Leu Ser
705                 710                 715                 720

Asp Gly Gly Leu Leu Ser Tyr Asp Gly Ser Ser Tyr Thr Thr Tyr
                725                 730                 735

Met Lys Glu Glu Val Asp Arg Tyr Arg Ile Thr Ile Gly Asn Lys Thr
            740                 745                 750

Cys Val Phe Glu Lys Glu Asn Asp Pro Ser Val Met Arg Ser Pro Ser
        755                 760                 765

Ala Gly Lys Leu Ile Gln Tyr Ile Val Glu Asp Gly Gly His Val Phe
    770                 775                 780

Ala Gly Gln Cys Tyr Ala Glu Ile Glu Val Met Lys Met Val Met Thr
785                 790                 795                 800

Leu Thr Ala Val Glu Ser Gly Cys Ile His Tyr Val Lys Arg Pro Gly
                805                 810                 815

Ala Ala Leu Asp Pro Gly Cys Val Leu Ala Lys Met Gln Leu Asp Asn
            820                 825                 830

Pro Ser Lys Val Gln Gln Ala Glu Leu His Thr Gly Ser Leu Pro Arg
        835                 840                 845

Ile Gln Ser Thr Ala Leu Arg Gly Glu Lys Leu His Arg Val Phe His
    850                 855                 860

Tyr Val Leu Asp Asn Leu Val Asn Val Met Asn Gly Tyr Cys Leu Pro
865                 870                 875                 880

Asp Pro Phe Phe Ser Ser Lys Val Lys Asp Trp Val Glu Arg Leu Met
                885                 890                 895

Lys Thr Leu Arg Asp Pro Ser Leu Pro Leu Leu Glu Leu Gln Asp Ile
            900                 905                 910

Met Thr Ser Val Ser Gly Arg Ile Pro Pro Asn Val Glu Lys Ser Ile
        915                 920                 925

Lys Lys Glu Met Ala Gln Tyr Ala Ser Asn Ile Thr Ser Val Leu Cys
    930                 935                 940

Gln Phe Pro Ser Gln Gln Ile Ala Asn Ile Leu Asp Ser His Ala Ala
945                 950                 955                 960

Thr Leu Asn Arg Lys Ser Glu Arg Glu Val Phe Phe Met Asn Thr Gln
                965                 970                 975

Ser Ile Val Gln Leu Val Gln Arg Tyr Arg Ser Gly Ile Arg Gly His
            980                 985                 990

Met Lys Ala Val Val Met Asp Leu Leu Arg Gln Tyr Leu Arg Val Glu
        995                 1000                1005

Thr Gln Phe Gln Asn Gly His Tyr Asp Lys Cys Val Phe Ala Leu
    1010                1015                1020

Arg Glu Glu Asn Lys Ser Asp Met Asn Thr Val Leu Asn Tyr Ile
    1025                1030                1035

Phe Ser His Ala Gln Val Thr Lys Lys Asn Leu Leu Val Thr Met
    1040                1045                1050

Leu Ile Asp Gln Leu Cys Gly Arg Asp Pro Thr Leu Thr Asp Glu
    1055                1060                1065
```

-continued

```
Leu Leu Asn Ile Leu Thr Glu Leu Thr Gln Leu Ser Lys Thr Thr
    1070                1075                1080

Asn Ala Lys Val Ala Leu Arg Ala Arg Gln Val Leu Ile Ala Ser
    1085                1090                1095

His Leu Pro Ser Tyr Glu Leu Arg His Asn Gln Val Glu Ser Ile
    1100                1105                1110

Phe Leu Ser Ala Ile Asp Met Tyr Gly His Gln Phe Cys Ile Glu
    1115                1120                1125

Asn Leu Gln Lys Leu Ile Leu Ser Glu Thr Ser Ile Phe Asp Val
    1130                1135                1140

Leu Pro Asn Phe Phe Tyr His Ser Asn Gln Val Val Arg Met Ala
    1145                1150                1155

Ala Leu Glu Val Tyr Val Arg Arg Ala Tyr Ile Ala Tyr Glu Leu
    1160                1165                1170

Asn Ser Val Gln His Arg Gln Leu Lys Asp Asn Thr Cys Val Val
    1175                1180                1185

Glu Phe Gln Phe Met Leu Pro Thr Ser His Pro Asn Arg Gly Asn
    1190                1195                1200

Ile Pro Thr Leu Asn Arg Met Ser Phe Ser Ser Asn Leu Asn His
    1205                1210                1215

Tyr Gly Met Thr His Val Ala Ser Val Ser Asp Val Leu Leu Asp
    1220                1225                1230

Asn Ser Phe Thr Pro Pro Cys Gln Arg Met Gly Gly Met Val Ser
    1235                1240                1245

Phe Arg Thr Phe Glu Asp Phe Val Arg Ile Phe Asp Glu Val Met
    1250                1255                1260

Gly Cys Phe Ser Asp Ser Pro Pro Gln Ser Pro Thr Phe Pro Glu
    1265                1270                1275

Ala Gly His Thr Ser Leu Tyr Asp Glu Asp Lys Val Pro Arg Asp
    1280                1285                1290

Glu Pro Ile His Ile Leu Asn Val Ala Ile Lys Thr Asp Cys Asp
    1295                1300                1305

Ile Glu Asp Asp Arg Leu Ala Ala Met Phe Arg Glu Phe Thr Gln
    1310                1315                1320

Gln Asn Lys Ala Thr Leu Val Asp His Gly Ile Arg Arg Leu Thr
    1325                1330                1335

Phe Leu Val Ala Gln Lys Asp Phe Arg Lys Gln Val Asn Tyr Glu
    1340                1345                1350

Val Asp Arg Arg Phe His Arg Glu Phe Pro Lys Phe Phe Thr Phe
    1355                1360                1365

Arg Ala Arg Asp Lys Phe Glu Asp Arg Ile Tyr Arg His Leu
    1370                1375                1380

Glu Pro Ala Leu Ala Phe Gln Leu Glu Leu Asn Arg Met Arg Asn
    1385                1390                1395

Phe Asp Leu Thr Ala Ile Pro Cys Ala Asn His Lys Met His Leu
    1400                1405                1410

Tyr Leu Gly Ala Ala Lys Val Glu Val Gly Thr Glu Val Thr Asp
    1415                1420                1425

Tyr Arg Phe Phe Val Arg Ala Ile Ile Arg His Ser Asp Leu Val
    1430                1435                1440

Thr Lys Glu Ala Ser Phe Glu Tyr Leu Gln Asn Glu Gly Glu Arg
    1445                1450                1455
```

-continued

```
Leu Leu Leu Glu Ala Met Asp Glu Leu Glu Val Ala Phe Asn Asn
1460                1465                1470

Thr Asn Val Arg Thr Asp Cys Asn His Ile Phe Leu Asn Phe Val
1475                1480                1485

Pro Thr Val Ile Met Asp Pro Ser Lys Ile Glu Ser Val Arg
1490                1495                1500

Ser Met Val Met Arg Tyr Gly Ser Arg Leu Trp Lys Leu Arg Val
1505                1510                1515

Leu Gln Ala Glu Leu Lys Ile Asn Ile Arg Leu Thr Pro Thr Gly
1520                1525                1530

Lys Ala Ile Pro Ile Arg Leu Phe Leu Thr Asn Glu Ser Gly Tyr
1535                1540                1545

Tyr Leu Asp Ile Ser Leu Tyr Lys Glu Val Thr Asp Ser Arg Thr
1550                1555                1560

Ala Gln Ile Met Phe Gln Ala Tyr Gly Asp Lys Gln Gly Pro Leu
1565                1570                1575

His Gly Met Leu Ile Asn Thr Pro Tyr Val Thr Lys Asp Leu Leu
1580                1585                1590

Gln Ser Lys Arg Phe Gln Ala Gln Ser Leu Gly Thr Thr Tyr Ile
1595                1600                1605

Tyr Asp Ile Pro Glu Met Phe Arg Gln Ser Leu Ile Lys Leu Trp
1610                1615                1620

Glu Ser Met Ser Thr Gln Ala Phe Leu Pro Ser Pro Pro Leu Pro
1625                1630                1635

Ser Asp Met Leu Thr Tyr Thr Glu Leu Val Leu Asp Asp Gln Gly
1640                1645                1650

Gln Leu Val His Met Asn Arg Leu Pro Gly Gly Asn Glu Ile Gly
1655                1660                1665

Met Val Ala Trp Lys Met Thr Phe Lys Ser Pro Glu Tyr Pro Glu
1670                1675                1680

Gly Arg Asp Ile Ile Val Ile Gly Asn Asp Ile Thr Tyr Arg Ile
1685                1690                1695

Gly Ser Phe Gly Pro Gln Glu Asp Leu Leu Phe Leu Arg Ala Ser
1700                1705                1710

Glu Leu Ala Arg Ala Glu Gly Ile Pro Arg Ile Tyr Val Ser Ala
1715                1720                1725

Asn Ser Gly Ala Arg Ile Gly Leu Ala Glu Glu Ile Arg His Met
1730                1735                1740

Phe His Val Ala Trp Val Asp Pro Glu Asp Pro Tyr Lys Gly Tyr
1745                1750                1755

Arg Tyr Leu Tyr Leu Thr Pro Gln Asp Tyr Lys Arg Val Ser Ala
1760                1765                1770

Leu Asn Ser Val His Cys Glu His Val Glu Asp Glu Gly Glu Ser
1775                1780                1785

Arg Tyr Lys Ile Thr Asp Ile Ile Gly Lys Glu Glu Gly Ile Gly
1790                1795                1800

Pro Glu Asn Leu Arg Gly Ser Gly Met Ile Ala Gly Glu Ser Ser
1805                1810                1815

Leu Ala Tyr Asn Glu Ile Ile Thr Ile Ser Leu Val Thr Cys Arg
1820                1825                1830

Ala Ile Gly Ile Gly Ala Tyr Leu Val Arg Leu Gly Gln Arg Thr
1835                1840                1845
```

```
Ile Gln Val Glu Asn Ser His Leu Ile Leu Thr Gly Ala Gly Ala
1850                1855                1860

Leu Asn Lys Val Leu Gly Arg Glu Val Tyr Thr Ser Asn Asn Gln
1865                1870                1875

Leu Gly Gly Ile Gln Ile Met His Asn Asn Gly Val Thr His Cys
1880                1885                1890

Thr Val Cys Asp Asp Phe Glu Gly Val Phe Thr Val Leu His Trp
1895                1900                1905

Leu Ser Tyr Met Pro Lys Ser Val His Ser Ser Val Pro Leu Leu
1910                1915                1920

Asn Ser Lys Asp Pro Ile Asp Arg Ile Ile Glu Phe Val Pro Thr
1925                1930                1935

Lys Thr Pro Tyr Asp Pro Arg Trp Met Leu Ala Gly Arg Pro His
1940                1945                1950

Pro Thr Gln Lys Gly Gln Trp Leu Ser Gly Phe Phe Asp Tyr Gly
1955                1960                1965

Ser Phe Ser Glu Ile Met Gln Pro Trp Ala Gln Thr Val Val Val
1970                1975                1980

Gly Arg Ala Arg Leu Gly Gly Ile Pro Val Gly Val Val Ala Val
1985                1990                1995

Glu Thr Arg Thr Val Glu Leu Ser Ile Pro Ala Asp Pro Ala Asn
2000                2005                2010

Leu Asp Ser Glu Ala Lys Ile Ile Gln Gln Ala Gly Gln Val Trp
2015                2020                2025

Phe Pro Asp Ser Ala Phe Lys Thr Tyr Gln Ala Ile Lys Asp Phe
2030                2035                2040

Asn Arg Glu Gly Leu Pro Leu Met Val Phe Ala Asn Trp Arg Gly
2045                2050                2055

Phe Ser Gly Gly Met Lys Asp Met Tyr Asp Gln Val Leu Lys Phe
2060                2065                2070

Gly Ala Tyr Ile Val Asp Gly Leu Arg Glu Cys Cys Gln Pro Val
2075                2080                2085

Leu Val Tyr Ile Pro Pro Gln Ala Glu Leu Arg Gly Gly Ser Trp
2090                2095                2100

Val Val Ile Asp Ser Ser Ile Asn Pro Arg His Met Glu Met Tyr
2105                2110                2115

Ala Asp Arg Glu Ser Arg Gly Ser Val Leu Glu Pro Glu Gly Thr
2120                2125                2130

Val Glu Ile Lys Phe Arg Arg Lys Asp Leu Val Lys Thr Met Arg
2135                2140                2145

Arg Val Asp Pro Val Tyr Ile His Leu Ala Glu Arg Leu Gly Thr
2150                2155                2160

Pro Glu Leu Ser Thr Ala Glu Arg Lys Glu Leu Glu Asn Lys Leu
2165                2170                2175

Lys Glu Arg Glu Glu Phe Leu Ile Pro Ile Tyr His Gln Val Ala
2180                2185                2190

Val Gln Phe Ala Asp Leu His Asp Thr Pro Gly Arg Met Gln Glu
2195                2200                2205

Lys Gly Val Ile Ser Asp Ile Leu Asp Trp Lys Thr Ser Arg Thr
2210                2215                2220

Phe Phe Tyr Trp Arg Leu Arg Arg Leu Leu Leu Glu Asp Leu Val
2225                2230                2235
```

```
Lys Lys Lys Ile His Asn Ala Asn Pro Glu Leu Thr Asp Gly Gln
    2240                2245                2250

Ile Gln Ala Met Leu Arg Arg Trp Phe Val Glu Val Glu Gly Thr
    2255                2260                2265

Val Lys Ala Tyr Val Trp Asp Asn Asn Lys Asp Leu Ala Glu Trp
    2270                2275                2280

Leu Glu Lys Gln Leu Thr Glu Glu Asp Gly Val His Ser Val Ile
    2285                2290                2295

Glu Glu Asn Ile Lys Cys Ile Ser Arg Asp Tyr Val Leu Lys Gln
    2300                2305                2310

Ile Arg Ser Leu Val Gln Ala Asn Pro Glu Val Ala Met Asp Ser
    2315                2320                2325

Ile Ile His Met Thr Gln His Ile Ser Pro Thr Gln Arg Ala Glu
    2330                2335                2340

Val Ile Arg Ile Leu Ser Thr Met Asp Ser Pro Ser Thr
    2345                2350                2355

<210> SEQ ID NO 2
<211> LENGTH: 2458
<212> TYPE: PRT
<213> ORGANISM: Homo sapiens

<400> SEQUENCE: 2

Met Val Leu Leu Leu Cys Leu Ser Cys Leu Ile Phe Ser Cys Leu Thr
1               5                   10                  15

Phe Ser Trp Leu Lys Ile Trp Gly Lys Met Thr Asp Ser Lys Pro Ile
                20                  25                  30

Thr Lys Ser Lys Ser Glu Ala Asn Leu Ile Pro Ser Gln Glu Pro Phe
            35                  40                  45

Pro Ala Ser Asp Asn Ser Gly Glu Thr Pro Gln Arg Asn Gly Glu Gly
        50                  55                  60

His Thr Leu Pro Lys Thr Pro Ser Gln Ala Glu Pro Ala Ser His Lys
65                  70                  75                  80

Gly Pro Lys Asp Ala Gly Arg Arg Asn Ser Leu Pro Pro Ser His
                85                  90                  95

Gln Lys Pro Pro Arg Asn Pro Leu Ser Ser Asp Ala Ala Pro Ser
            100                 105                 110

Pro Glu Leu Gln Ala Asn Gly Thr Gly Thr Gly Leu Glu Ala Thr
        115                 120                 125

Asp Thr Asn Gly Leu Ser Ser Ser Ala Arg Pro Gln Gly Gln Gln Ala
130                 135                 140

Gly Ser Pro Ser Lys Glu Asp Lys Lys Gln Ala Asn Ile Lys Arg Gln
145                 150                 155                 160

Leu Met Thr Asn Phe Ile Leu Gly Ser Phe Asp Tyr Ser Ser Asp
                165                 170                 175

Glu Asp Ser Val Ala Gly Ser Ser Arg Glu Ser Thr Arg Lys Gly Ser
            180                 185                 190

Arg Ala Ser Leu Gly Ala Leu Ser Leu Glu Ala Tyr Leu Thr Thr Gly
        195                 200                 205

Glu Ala Glu Thr Arg Val Pro Thr Met Arg Pro Ser Met Ser Gly Leu
    210                 215                 220

His Leu Val Lys Arg Gly Arg Glu His Lys Leu Asp Leu His Arg
225                 230                 235                 240

Asp Phe Thr Val Ala Ser Pro Ala Glu Phe Val Thr Arg Phe Gly Gly
                245                 250                 255
```

```
Asp Arg Val Ile Glu Lys Val Leu Ile Ala Asn Asn Gly Ile Ala Ala
            260                 265                 270

Val Lys Cys Met Arg Ser Ile Arg Arg Trp Ala Tyr Glu Met Phe Arg
        275                 280                 285

Asn Glu Arg Ala Ile Arg Phe Val Val Met Val Thr Pro Glu Asp Leu
    290                 295                 300

Lys Ala Asn Ala Glu Tyr Ile Lys Met Ala Asp His Tyr Val Pro Val
305                 310                 315                 320

Pro Gly Gly Pro Asn Asn Asn Tyr Ala Asn Val Glu Leu Ile Val
                325                 330                 335

Asp Ile Ala Lys Arg Ile Pro Val Gln Ala Val Trp Ala Gly Trp Gly
            340                 345                 350

His Ala Ser Glu Asn Pro Lys Leu Pro Glu Leu Leu Cys Lys Asn Gly
        355                 360                 365

Val Ala Phe Leu Gly Pro Pro Ser Glu Ala Met Trp Ala Leu Gly Asp
    370                 375                 380

Lys Ile Ala Ser Thr Val Ala Gln Thr Leu Gln Val Pro Thr Leu
385                 390                 395                 400

Pro Trp Ser Gly Ser Gly Leu Thr Val Glu Trp Thr Glu Asp Asp Leu
            405                 410                 415

Gln Gln Gly Lys Arg Ile Ser Val Pro Glu Asp Val Tyr Asp Lys Gly
        420                 425                 430

Cys Val Lys Asp Val Asp Glu Gly Leu Glu Ala Ala Glu Arg Ile Gly
    435                 440                 445

Phe Pro Leu Met Ile Lys Ala Ser Glu Gly Gly Gly Lys Gly Ile
450                 455                 460

Arg Lys Ala Glu Ser Ala Glu Asp Phe Pro Ile Leu Phe Arg Gln Val
465                 470                 475                 480

Gln Ser Glu Ile Pro Gly Ser Pro Ile Phe Leu Met Lys Leu Ala Gln
            485                 490                 495

His Ala Arg His Leu Glu Val Gln Ile Leu Ala Asp Gln Tyr Gly Asn
        500                 505                 510

Ala Val Ser Leu Phe Gly Arg Asp Cys Ser Ile Gln Arg Arg His Gln
    515                 520                 525

Lys Ile Val Glu Glu Ala Pro Ala Thr Ile Ala Pro Leu Ala Ile Phe
530                 535                 540

Glu Phe Met Glu Gln Cys Ala Ile Arg Leu Ala Lys Thr Val Gly Tyr
545                 550                 555                 560

Val Ser Ala Gly Thr Val Glu Tyr Leu Tyr Ser Gln Asp Gly Ser Phe
            565                 570                 575

His Phe Leu Glu Leu Asn Pro Arg Leu Gln Val Glu His Pro Cys Thr
        580                 585                 590

Glu Met Ile Ala Asp Val Asn Leu Pro Ala Ala Gln Leu Gln Ile Ala
    595                 600                 605

Met Gly Val Pro Leu His Arg Leu Lys Asp Ile Arg Leu Leu Tyr Gly
610                 615                 620

Glu Ser Pro Trp Gly Val Thr Pro Ile Ser Phe Glu Thr Pro Ser Asn
625                 630                 635                 640

Pro Pro Leu Ala Arg Gly His Val Ile Ala Ala Arg Ile Thr Ser Glu
            645                 650                 655

Asn Pro Asp Glu Gly Phe Lys Pro Ser Ser Gly Thr Val Gln Glu Leu
        660                 665                 670
```

```
Asn Phe Arg Ser Ser Lys Asn Val Trp Gly Tyr Phe Ser Val Ala Ala
            675                 680                 685

Thr Gly Gly Leu His Glu Phe Ala Asp Ser Gln Phe Gly His Cys Phe
690                 695                 700

Ser Trp Gly Glu Asn Arg Glu Glu Ala Ile Ser Asn Met Val Val Ala
705                 710                 715                 720

Leu Lys Glu Leu Ser Ile Arg Gly Asp Phe Arg Thr Val Glu Tyr
                725                 730                 735

Leu Ile Asn Leu Leu Glu Thr Glu Ser Phe Gln Asn Asn Asp Ile Asp
            740                 745                 750

Thr Gly Trp Leu Asp Tyr Leu Ile Ala Glu Lys Val Gln Ala Glu Lys
            755                 760                 765

Pro Asp Ile Met Leu Gly Val Val Cys Gly Ala Leu Asn Val Ala Asp
770                 775                 780

Ala Met Phe Arg Thr Cys Met Thr Asp Phe Leu His Ser Leu Glu Arg
785                 790                 795                 800

Gly Gln Val Leu Pro Ala Asp Ser Leu Leu Asn Leu Val Asp Val Glu
                805                 810                 815

Leu Ile Tyr Gly Gly Val Lys Tyr Ile Leu Lys Val Ala Arg Gln Ser
            820                 825                 830

Leu Thr Met Phe Val Leu Ile Met Asn Gly Cys His Ile Glu Ile Asp
            835                 840                 845

Ala His Arg Leu Asn Asp Gly Gly Leu Leu Leu Ser Tyr Asn Gly Asn
            850                 855                 860

Ser Tyr Thr Thr Tyr Met Lys Glu Glu Val Asp Ser Tyr Arg Ile Thr
865                 870                 875                 880

Ile Gly Asn Lys Thr Cys Val Phe Glu Lys Glu Asn Asp Pro Thr Val
                885                 890                 895

Leu Arg Ser Pro Ser Ala Gly Lys Leu Thr Gln Tyr Thr Val Glu Asp
                900                 905                 910

Gly Gly His Val Glu Ala Gly Ser Ser Tyr Ala Glu Met Glu Val Met
            915                 920                 925

Lys Met Ile Met Thr Leu Asn Val Gln Glu Arg Gly Arg Val Lys Tyr
930                 935                 940

Ile Lys Arg Pro Gly Ala Val Leu Glu Ala Gly Cys Val Val Ala Arg
945                 950                 955                 960

Leu Glu Leu Asp Asp Pro Ser Lys Val His Pro Ala Glu Pro Phe Thr
                965                 970                 975

Gly Glu Leu Pro Ala Gln Gln Thr Leu Pro Ile Leu Gly Glu Lys Leu
            980                 985                 990

His Gln Val Phe His Ser Val Leu Glu Asn Leu Thr Asn Val Met Ser
            995                 1000                1005

Gly Phe Cys Leu Pro Glu Pro Val Phe Ser Ile Lys Leu Lys Glu
    1010                1015                1020

Trp Val Gln Lys Leu Met Met Thr Leu Arg His Pro Ser Leu Pro
    1025                1030                1035

Leu Leu Glu Leu Gln Glu Ile Met Thr Ser Val Ala Gly Arg Ile
    1040                1045                1050

Pro Ala Pro Val Glu Lys Ser Val Arg Arg Val Met Ala Gln Tyr
    1055                1060                1065

Ala Ser Asn Ile Thr Ser Val Leu Cys Gln Phe Pro Ser Gln Gln
    1070                1075                1080
```

```
Ile Ala Thr Ile Leu Asp Cys His Ala Ala Thr Leu Gln Arg Lys
1085                1090                1095

Ala Asp Arg Glu Val Phe Phe Ile Asn Thr Gln Ser Ile Val Gln
1100                1105                1110

Leu Val Gln Arg Tyr Arg Ser Gly Ile Arg Gly Tyr Met Lys Thr
1115                1120                1125

Val Val Leu Asp Leu Leu Arg Arg Tyr Leu Arg Val Glu His His
1130                1135                1140

Phe Gln Gln Ala His Tyr Asp Lys Cys Val Ile Asn Leu Arg Glu
1145                1150                1155

Gln Phe Lys Pro Asp Met Ser Gln Val Leu Asp Cys Ile Phe Ser
1160                1165                1170

His Ala Gln Val Ala Lys Lys Asn Gln Leu Val Ile Met Leu Ile
1175                1180                1185

Asp Glu Leu Cys Gly Pro Asp Pro Ser Leu Ser Asp Glu Leu Ile
1190                1195                1200

Ser Ile Leu Asn Glu Leu Thr Gln Leu Ser Lys Ser Glu His Cys
1205                1210                1215

Lys Val Ala Leu Arg Ala Arg Gln Ile Leu Ile Ala Ser His Leu
1220                1225                1230

Pro Ser Tyr Glu Leu Arg His Asn Gln Val Glu Ser Ile Phe Leu
1235                1240                1245

Ser Ala Ile Asp Met Tyr Gly His Gln Phe Cys Pro Glu Asn Leu
1250                1255                1260

Lys Lys Leu Ile Leu Ser Glu Thr Thr Ile Phe Asp Val Leu Pro
1265                1270                1275

Thr Phe Phe Tyr His Ala Asn Lys Val Val Cys Met Ala Ser Leu
1280                1285                1290

Glu Val Tyr Val Arg Arg Gly Tyr Ile Ala Tyr Glu Leu Asn Ser
1295                1300                1305

Leu Gln His Arg Gln Leu Pro Asp Gly Thr Cys Val Val Glu Phe
1310                1315                1320

Gln Phe Met Leu Pro Ser Ser His Pro Asn Arg Met Thr Val Pro
1325                1330                1335

Ile Ser Ile Thr Asn Pro Asp Leu Leu Arg His Ser Thr Glu Leu
1340                1345                1350

Phe Met Asp Ser Gly Phe Ser Pro Leu Cys Gln Arg Met Gly Ala
1355                1360                1365

Met Val Ala Phe Arg Arg Phe Glu Asp Phe Thr Arg Asn Phe Asp
1370                1375                1380

Glu Val Ile Ser Cys Phe Ala Asn Val Pro Lys Asp Thr Pro Leu
1385                1390                1395

Phe Ser Glu Ala Arg Thr Ser Leu Tyr Ser Glu Asp Asp Cys Lys
1400                1405                1410

Ser Leu Arg Glu Glu Pro Ile His Ile Leu Asn Val Ser Ile Gln
1415                1420                1425

Cys Ala Asp His Leu Glu Asp Glu Ala Leu Val Pro Ile Leu Arg
1430                1435                1440

Thr Phe Val Gln Ser Lys Lys Asn Ile Leu Val Asp Tyr Gly Leu
1445                1450                1455

Arg Arg Ile Thr Phe Leu Ile Ala Gln Glu Lys Glu Phe Pro Lys
1460                1465                1470
```

-continued

Phe Phe Thr Phe Arg Ala Arg Asp Glu Phe Ala Glu Asp Arg Ile
1475                1480                    1485

Tyr Arg His Leu Glu Pro Ala Leu Ala Phe Gln Leu Glu Leu Asn
    1490                1495                    1500

Arg Met Arg Asn Phe Asp Leu Thr Ala Val Pro Cys Ala Asn His
    1505                1510                    1515

Lys Met His Leu Tyr Leu Gly Ala Ala Lys Val Lys Glu Gly Val
    1520                1525                    1530

Glu Val Thr Asp His Arg Phe Phe Ile Arg Ala Ile Ile Arg His
    1535                1540                    1545

Ser Asp Leu Ile Thr Lys Glu Ala Ser Phe Glu Tyr Leu Gln Asn
    1550                1555                    1560

Glu Gly Glu Arg Leu Leu Leu Glu Ala Met Asp Glu Leu Glu Val
    1565                1570                    1575

Ala Phe Asn Asn Thr Ser Val Arg Thr Asp Cys Asn His Ile Phe
    1580                1585                    1590

Leu Asn Phe Val Pro Thr Val Ile Met Asp Pro Phe Lys Ile Glu
    1595                1600                    1605

Glu Ser Val Arg Tyr Met Val Met Arg Tyr Gly Ser Arg Leu Trp
    1610                1615                    1620

Lys Leu Arg Val Leu Gln Ala Glu Val Lys Ile Asn Ile Arg Gln
    1625                1630                    1635

Thr Thr Thr Gly Ser Ala Val Pro Ile Arg Leu Phe Ile Thr Asn
    1640                1645                    1650

Glu Ser Gly Tyr Tyr Leu Asp Ile Ser Leu Tyr Lys Glu Val Thr
    1655                1660                    1665

Asp Ser Arg Ser Gly Asn Ile Met Phe His Ser Phe Gly Asn Lys
    1670                1675                    1680

Gln Gly Pro Gln His Gly Met Leu Ile Asn Thr Pro Tyr Val Thr
    1685                1690                    1695

Lys Asp Leu Leu Gln Ala Lys Arg Phe Gln Ala Gln Thr Leu Gly
    1700                1705                    1710

Thr Thr Tyr Ile Tyr Asp Phe Pro Glu Met Phe Arg Gln Ala Leu
    1715                1720                    1725

Phe Lys Leu Trp Gly Ser Pro Asp Lys Tyr Pro Lys Asp Ile Leu
    1730                1735                    1740

Thr Tyr Thr Glu Leu Val Leu Asp Ser Gln Gly Gln Leu Val Glu
    1745                1750                    1755

Met Asn Arg Leu Pro Gly Gly Asn Glu Val Gly Met Val Ala Phe
    1760                1765                    1770

Lys Met Arg Phe Lys Thr Gln Glu Tyr Pro Glu Gly Arg Asp Val
    1775                1780                    1785

Ile Val Ile Gly Asn Asp Ile Thr Phe Arg Ile Gly Ser Phe Gly
    1790                1795                    1800

Pro Gly Glu Asp Leu Leu Tyr Leu Arg Ala Ser Glu Met Ala Arg
    1805                1810                    1815

Ala Glu Gly Ile Pro Lys Ile Tyr Val Ala Ala Asn Ser Gly Ala
    1820                1825                    1830

Arg Ile Gly Met Ala Glu Glu Ile Lys His Met Phe His Val Ala
    1835                1840                    1845

Trp Val Asp Pro Glu Asp Pro His Lys Gly Phe Lys Tyr Leu Tyr
    1850                1855                    1860

-continued

```
Leu Thr Pro Gln Asp Tyr Thr Arg Ile Ser Ser Leu Asn Ser Val
    1865                1870                1875

His Cys Lys His Ile Glu Glu Gly Gly Glu Ser Arg Tyr Met Ile
    1880                1885                1890

Thr Asp Ile Ile Gly Lys Asp Asp Gly Leu Gly Val Glu Asn Leu
    1895                1900                1905

Arg Gly Ser Gly Met Ile Ala Gly Glu Ser Ser Leu Ala Tyr Glu
    1910                1915                1920

Glu Ile Val Thr Ile Ser Leu Val Thr Cys Arg Ala Ile Gly Ile
    1925                1930                1935

Gly Ala Tyr Leu Val Arg Leu Gly Gln Arg Val Ile Gln Val Glu
    1940                1945                1950

Asn Ser His Ile Ile Leu Thr Gly Ala Ser Ala Leu Asn Lys Val
    1955                1960                1965

Leu Gly Arg Glu Val Tyr Thr Ser Asn Asn Gln Leu Gly Gly Val
    1970                1975                1980

Gln Ile Met His Tyr Asn Gly Val Ser His Ile Thr Val Pro Asp
    1985                1990                1995

Asp Phe Glu Gly Val Tyr Thr Ile Leu Glu Trp Leu Ser Tyr Met
    2000                2005                2010

Pro Lys Asp Asn His Ser Pro Val Pro Ile Ile Thr Pro Thr Asp
    2015                2020                2025

Pro Ile Asp Arg Glu Ile Glu Phe Leu Pro Ser Arg Ala Pro Tyr
    2030                2035                2040

Asp Pro Arg Trp Met Leu Ala Gly Arg Pro His Pro Thr Leu Lys
    2045                2050                2055

Gly Thr Trp Gln Ser Gly Phe Phe Asp His Gly Ser Phe Lys Glu
    2060                2065                2070

Ile Met Ala Pro Trp Ala Gln Thr Val Val Thr Gly Arg Ala Arg
    2075                2080                2085

Leu Gly Gly Ile Pro Val Gly Val Ile Ala Val Glu Thr Arg Thr
    2090                2095                2100

Val Glu Val Ala Val Pro Ala Asp Pro Ala Asn Leu Asp Ser Glu
    2105                2110                2115

Ala Lys Ile Ile Gln Gln Ala Gly Gln Val Trp Phe Pro Asp Ser
    2120                2125                2130

Ala Tyr Lys Thr Ala Gln Ala Ile Lys Asp Phe Asn Arg Glu Lys
    2135                2140                2145

Leu Pro Leu Met Ile Phe Ala Asn Trp Arg Gly Phe Ser Gly Gly
    2150                2155                2160

Met Lys Asp Met Tyr Asp Gln Val Leu Lys Phe Gly Ala Tyr Ile
    2165                2170                2175

Val Asp Gly Leu Arg Gln Tyr Lys Gln Pro Ile Leu Ile Tyr Ile
    2180                2185                2190

Pro Pro Tyr Ala Glu Leu Arg Gly Gly Ser Trp Val Val Ile Asp
    2195                2200                2205

Ala Thr Ile Asn Pro Leu Cys Ile Glu Met Tyr Ala Asp Lys Glu
    2210                2215                2220

Ser Arg Gly Gly Val Leu Glu Pro Glu Gly Thr Val Glu Ile Lys
    2225                2230                2235

Phe Arg Lys Lys Asp Leu Ile Lys Ser Met Arg Arg Ile Asp Pro
    2240                2245                2250
```

| | | | | | | | | | | | |
|---|---|---|---|---|---|---|---|---|---|---|---|
| Ala | Tyr 2255 | Lys | Lys | Leu | Met 2260 | Glu | Gln | Leu | Gly | Glu 2265 | Pro | Asp | Leu | Ser |
| Asp | Lys 2270 | Asp | Arg | Lys | Asp 2275 | Leu | Glu | Gly | Arg | Leu 2280 | Lys | Ala | Arg | Glu |
| Asp | Leu 2285 | Leu | Leu | Pro | Ile 2290 | Tyr | His | Gln | Val | Ala 2295 | Val | Gln | Phe | Ala |
| Asp | Phe 2300 | His | Asp | Thr | Pro 2305 | Gly | Arg | Met | Leu | Glu 2310 | Lys | Gly | Val | Ile |
| Ser | Asp 2315 | Ile | Leu | Glu | Trp 2320 | Lys | Thr | Ala | Arg | Thr 2325 | Phe | Leu | Tyr | Trp |
| Arg | Leu 2330 | Arg | Arg | Leu | Leu 2335 | Leu | Glu | Asp | Gln | Val 2340 | Lys | Gln | Glu | Ile |
| Leu | Gln 2345 | Ala | Ser | Gly | Glu 2350 | Leu | Ser | His | Val | His 2355 | Ile | Gln | Ser | Met |
| Leu | Arg 2360 | Arg | Trp | Phe | Val 2365 | Glu | Thr | Glu | Gly | Ala 2370 | Val | Lys | Ala | Tyr |
| Leu | Trp 2375 | Asp | Asn | Asn | Gln 2380 | Val | Val | Val | Gln | Trp 2385 | Leu | Glu | Gln | His |
| Trp | Gln 2390 | Ala | Gly | Asp | Gly 2395 | Pro | Arg | Ser | Thr | Ile 2400 | Arg | Glu | Asn | Ile |
| Thr | Tyr 2405 | Leu | Lys | His | Asp 2410 | Ser | Val | Leu | Lys | Thr 2415 | Ile | Arg | Gly | Leu |
| Val | Glu 2420 | Glu | Asn | Pro | Glu 2425 | Val | Ala | Val | Asp | Cys 2430 | Val | Ile | Tyr | Leu |
| Ser | Gln 2435 | His | Ile | Ser | Pro 2440 | Ala | Glu | Arg | Ala | Gln 2445 | Val | Val | His | Leu |
| Leu | Ser 2450 | Thr | Met | Asp | Ser 2455 | Pro | Ala | Ser | Thr | | | | | |